US009017990B2

(12) United States Patent
Lam et al.

(10) Patent No.: US 9,017,990 B2
(45) Date of Patent: Apr. 28, 2015

(54) METHODS FOR ENZYMATIC DECOLORIZATION OF CHLOROPHYLL

(75) Inventors: David Lam, San Diego, CA (US); David Weiner, Del Mar, CA (US); Timothy Hitchman, San Diego, CA (US); Nelson Barton, San Diego, CA (US); Mark Burk, San Diego, CA (US)

(73) Assignee: DSM IP Assets B.V., Heerlen (NL)

( * ) Notice: Subject to any disclaimer, the term of this patent is extended or adjusted under 35 U.S.C. 154(b) by 1022 days.

(21) Appl. No.: 13/103,276

(22) Filed: May 9, 2011

(65) Prior Publication Data

US 2011/0306117 A1    Dec. 15, 2011

Related U.S. Application Data

(62) Division of application No. 11/570,169, filed as application No. PCT/US2005/032351 on Sep. 9, 2005, now abandoned.

(60) Provisional application No. 60/609,125, filed on Sep. 10, 2004.

(51) Int. Cl.
*C12P 7/64* (2006.01)
*C12S 3/00* (2006.01)
*C12S 3/18* (2006.01)
*C12N 9/18* (2006.01)

(52) U.S. Cl.
CPC ........................................ *C12N 9/18* (2013.01)

(58) Field of Classification Search
None
See application file for complete search history.

(56) References Cited

U.S. PATENT DOCUMENTS

| | | | |
|---|---|---|---|
| 4,698,185 A | 10/1987 | Dijkstra | |
| 4,707,364 A | 11/1987 | Barach | |
| 4,719,178 A | 1/1988 | Macrae | |
| 4,752,483 A | 6/1988 | Hagberg | |
| 4,861,716 A | 8/1989 | Macrae | |
| 4,873,109 A | 10/1989 | Tanaka | |
| 4,946,778 A | 8/1990 | Ladner | |
| 5,061,498 A | 10/1991 | Matsuzaki | |
| 5,264,367 A | 11/1993 | Aalrust | |
| 5,288,619 A | 2/1994 | Brown | |
| 5,304,477 A | 4/1994 | Nagoh | |
| 5,315,021 A | 5/1994 | Beharry | |
| 5,395,629 A | 3/1995 | Bertoli | |
| 5,414,100 A | 5/1995 | Ayorinde | |
| 5,470,741 A | 11/1995 | Oester | |
| 5,508,048 A | 4/1996 | Padley | |
| 5,558,781 A | 9/1996 | Buchold | |
| 5,654,181 A | 8/1997 | Oester | |
| 6,001,640 A | 12/1999 | Loeffler | |
| 6,022,577 A | 2/2000 | Chrysam | |
| 6,103,505 A | 8/2000 | Clausen | |
| 6,127,137 A | 10/2000 | Hasida | |
| 6,162,623 A | 12/2000 | Grote | |
| 6,355,396 B1 | 3/2002 | Nakamura | |
| 6,376,689 B1 | 4/2002 | Muralidhara | |
| 6,537,776 B1 | 3/2003 | Short | |
| 6,660,491 B2 | 12/2003 | Norinobu | |
| 2002/0001809 A1 | 1/2002 | Short | |
| 2002/0080350 A1 | 6/2002 | Lafferty | |
| 2003/0190651 A1 | 10/2003 | Kossida | |
| 2005/0108789 A1 | 5/2005 | Gramatikova | |
| 2007/0202566 A1 | 8/2007 | Bornscheuer | |

FOREIGN PATENT DOCUMENTS

| | | |
|---|---|---|
| CA | 1102795 | 6/1981 |
| EP | 0070269 | 1/1983 |
| EP | 0196210 | 10/1986 |
| EP | 0427309 | 5/1991 |
| EP | 0093602 | 3/1995 |
| EP | 0513709 | 3/1995 |
| EP | 0268456 | 5/1998 |
| EP | 0882797 | 12/1998 |
| JP | 57156482 | 9/1982 |
| JP | 63-418988 | 6/1988 |
| JP | 05132283 | 5/1993 |
| JP | 06306386 | 11/1994 |
| WO | WO 83/03844 | 11/1983 |
| WO | WO 92/13130 | 8/1992 |
| WO | WO 93/24619 | 12/1993 |
| WO | WO 95/05475 | 2/1995 |
| WO | WO 96/40844 | 12/1996 |
| WO | WO 97/01629 | 1/1997 |
| WO | WO 99/14338 | 3/1999 |

(Continued)

OTHER PUBLICATIONS

Napal et al. (J. Biol. Chem. 2003; vol. 278, pp. 34084-34089).*
USPTO—Dec. 9, 2010—Office Action—U.S. Appl. No. 11/570,169.
Birschbach—Bulletin of the IDF (1992)—269—36-39.
Harboe—Bulletin of the IDF (1994)—294—11-16.
Kanfer—Lipids—(1975)—10—391-394.
Kotting—Lipases and phospholipases in organic synthesis. In: P. Woolley and S.B. Petersen, Editors, Lipases, Their Structure, Biochemistry and Application, Cambridge University Press, Cambridge (1994), pp. 289-314.

(Continued)

Primary Examiner — Russell Kallis
(74) Attorney, Agent, or Firm — Miles & Stockbridge PC

(57) ABSTRACT

The invention provides the invention provides compositions and methods for the enzymatic treatment ("bleaching" or "de-colorizing") of chlorophyll-comprising compositions, e.g., algae preparations, chlorophyll-containing or chlorophyll-contaminated feeds, foods or oils, for example, vegetable oils, including oils processed from oilseeds, such as canola (rapeseed) oil or soybean oil, or oil fruits, such as palm oil. In one aspect, the invention provides methods using a chlorophyllase enzyme for the enzymatic hydrolysis of chlorophyll in an algae, an animal (e.g., a fish) or plant preparation, a food or an oil. In one aspect, the chlorophyllase is immobilized onto a silica. The invention also provides compositions of manufacture and detergents.

16 Claims, 16 Drawing Sheets

(56) References Cited

FOREIGN PATENT DOCUMENTS

| | | |
|---|---|---|
| WO | WO 99/66805 | 12/1999 |
| WO | WO 01/75076 | 10/2001 |
| WO | WO 01/96551 | 12/2001 |
| WO | WO 02/06505 | 1/2002 |
| WO | WO 02/20735 | 3/2002 |
| WO | WO 02/26998 | 4/2002 |
| WO | WO 02/29022 | 4/2002 |
| WO | WO 02/29032 | 4/2002 |
| WO | WO 02/31203 | 4/2002 |
| WO | WO 02/44336 | 6/2002 |
| WO | WO 02/057411 | 7/2002 |
| WO | WO 02/081719 | 10/2002 |
| WO | WO 02/094949 | 11/2002 |
| WO | WO 03/089620 | 10/2003 |
| WO | WO 2005/032496 | 4/2005 |
| WO | WO 2005/086900 | 9/2005 |
| WO | WO 2006/009676 | 1/2006 |
| WO | WO 2006/096834 | 9/2006 |
| WO | WO 2008/036863 | 3/2008 |
| WO | WO 2009/088980 | 7/2009 |

OTHER PUBLICATIONS

Search Report—PCT/US2005/032351—IPRP—Mar. 5, 2009.
Zwaal—Phospholipase C from Bicillus cereus—Methods in Enzymology (1974)—32—154-161.
Ahn—Chem. Commun. (2004)—364-365.
Arisawa—Applied and Environmental Microbiology (2002)—68—2716-2725.
Briand—Eur. J. Biochem.—(1995)—228—169-175.
Database—UNIPROT Accession No. 029131—(1998)—Klenk.
Gupta—Applied Microbiology Biotechnology (2002)—59—15-32.
Gutierrez—Trends in Biotechnology (2001)—19—340-348.
Haring—Journal of Organic Chemistry (1999)—64—832-835.
Hoondal—Applied Microbiology Biotechnology (2002)—59—409-418.
Jaeger—Tibtech (1998)—16—396-403.
Jimenez—Biotech. Prog. (2002)—18—635-640.
Kadowaki—J. Biol. Chem. (2002)—275—25577-25584.
Klenk—Nature (1997)—390—364-370.
Kurvinen—Lipids (2001)—36—1377-1382.
Loeffler—Science (2001)—294—2170-2172.
Rogalska—Chirality (1993)—5—24-30.
Sadek—Jour. of Applied Bacteriology (1957)—20—137-144.
Search report—EP06748332.1 Extended EP Search Report—Mar. 8, 2010.
Search Report—PCT/US2005/032351—ISR & WO—Jun. 3, 2008.
Seo—Biotechnology Letters (2004)—1-5.
Tyrrell—J. Neurosci. (2001)—21—9629-9637.
Wongsakul—Eur. J. Lipid Science Technol. (2003)—105—68-73.
Yamamura—Biochemical and Biophysical Research Communications (2002)—294—1138-1143.
Genbank Accession No. AAD35127 (1999) Thermotoga maritima MSB8—Nelson.
JPO—Mar. 23, 2010—Office Action—2006-509241.
Columbian Patent Office—Apr. 19, 2010—Office Action—05101225 (translation of office action and comments provided by foreign associate in letter dated Mar. 18, 2010).
Chagaev—"Role of Fibre Collapse in Mechanical Pulping" (Abstract)—International Mechanical Pulping Conference Proceedings (1999).
Cisneros—"Fiber Surface Characteristics of Hardwood Refiner Pulps" (Abstract)—Pulping Conference Proceedings (1992).
EPO—06748332.1—94(3) Communication—(Jul. 4, 2011).
Haller—"Cartapip(R) Treatment of Wood Chips to Reduce Pitch and Improve Processing" (Abstract)—Pulping Conference Proceedings (1992).
McFeeters—Plant Physiology (1971) 47—609-618.

Nazhad—"Influence of Formation on Tensile Strength of Paper Made From Mechanical Pulps" (Abstract)—Papermakers Conference Proceedings (2000).
Coutinho—Food Research International (2009) 42—536-550.
EPO—Feb. 25, 2010—Article 94(3) Communication—EP05762779.6—Feb. 25, 2011.
JPO—Office Action—JP2007-516623—Mar. 7, 2011.
Tsuchiya—PNAS (1999) 95—15362-15367.
Search Report—PCT/US2010/051920—International Search Report—Jul. 4, 2011.
Dijkstra—Journal of the American Oil Chemists' Society (1989)—66—1002-1009.
Suzuki—Journal of the American Chemists' Society (1993) 70—837-841.
PCT/USIB2010/052581—ISR—Dec. 27, 2010.
Pere—"Use of Purified Enzymes in Mechanical Pulping" (Abstract)—Pulping Conference Proceedings (1996).
Schelbert—Plant Cell (2009) 21—767-785.
Seffernick—J. Bacteriol. (2001)—8—2405-2410.
Stratton—"Characterization of Fiber-Fiber Bond Strength from Paper Mechanical Properties" (Abstract)—International Paper Physics Conference Proceedings (1991).
UNIPROT Accession No. A8J2S9—Chlorophyllase I (Dec. 4, 2007).
USPTO—Mar. 1, 2011—Office Action U.S. Appl. No. 11/575,066.
USPTO—Jan. 31, 2011—Final Office Action—U.S. Appl. No. 10/547,956.
USPTO—Jul. 21, 2011—Office Action—U.S. Appl. No. 11/817,865.
Witkowski—Biochemistry (1999)—38—11643-11650.
CIPO—Aug. 5, 2011—Requisition—CA 2,515,583.
EPO—EP Article 94(3) Communication—07853585.3—Feb. 22, 2011.
NPL—Search Report—PCT/US2004/007095—ISR & WO—Jul. 31, 2008.
CIPO—CA Office Action—CA 2,481,411—Apr. 4, 2011.
Dijkstra—"Enzymatic Degumming", European Journal of Lipid Science and Technologyy (2010)—112—1178-1189.
EP10180847.5—Extended EP Search Report—Jan. 27, 2011.
Senda—Plant Cell Physiology (1996)—37—347-353.
Branden—Introduction to Protein Structure, Garland Publishing Inc., New York, p. 247 (1991).
PCT/US2010/51903—ISR & WO—Feb. 28, 2011.
AUIP—Oct. 11, 2010—First Examination Report—2005264938.
EPO—Feb. 25, 2010—Article 94(3) Communication—EP05762779.6.
Buenrostro—Biotech Letters (1986)—8—505-506.
Kasai—J Agric Food Chem (2003)—51—6217-6222.
McGlone—J of Food Science (1986)—51—695-697.
Montedoro—Acta Vitamin Enzymol. (1976)—30—13-27.
Ouhida—J Agric Food Chem (2002)—50—1933-1938.
Rosenthal—Enzyme and Microb. Tech. (2001)—28—499-509.
Sosulski—Proc.Can.Inst.Food.Sci Technol. (1990)—3—656-662.
Barany—PCR Methods and Applications (1991)—1—5-16.
Bockisch—Fats and Oils Handbook (1998)—5—345-445.
Fahy—PCR Methods and Applications (1991)—1—25-33.
Gao—Biotechnol Prog. (2004)—20—443-448.
Gluzman—Cell (1981)—23—175-182.
Gurtu—Biochem Biopys Res Commun (1996)—229—295-298.
Jacob-Wilk—The Plant Journal (1999)—20—653-661.
Kohler—Nature (1975)—256—495-497.
Kozbor—Immunology Today (1983)—4—72-79.
Marchler-Bauer—Nucleic Acids Res (2003)—31—383-387.
Sanders—Dev. Biol. Stand. (1987)—66—55-63.
Search Report—PCT/US2005/020866—IPRP—Mar. 19, 2009.
Search Report—PCT/US2005/020866—ISR & WO—May 9, 2008.
Venuti—Pharm. Res. (1989)—6—867-873.
Walker—Nucleic Acid Research (1992)—20—1691-1696.
Wood—Methods of Enzymology (1988)—160—87-112.
Yi—J of Molecular Catalysis B: Enzymatic (2002)—19—319-325.
Bitar—Journal of the American Oil Chemists' Society (2004)—81—927-932.
Database—GENESEQ Accession No. AEH46911, Environmental isolate DNA encoding a hydrolase—Jul. 27, 2006.

(56) References Cited

OTHER PUBLICATIONS

Database—GENESEQ Accession No. AEH46912, Environmental isolate hydrolase—Jul. 27, 2006.
Khamessan—Journal of Food Biochemistry (1994)—20—311-328.
Search report—EP05762779—Supplemental EP Search Report—Sep. 16, 2009.
Database—Genbank Accession No. AY195600 (2003)—Pomerantsev.
Database—Genbank Accession No. M24149 (1989)—Gilmore.
Database—Genbank Accession No. X12854 (1988)—Johansen.
Database—GENBANK Accession No. X64140 (1992)—Gavrilenko.
Database—GENBANK Accession No. X64141 (1992)—Gavrilenko.
Database—GENBANK Accession No. Y16268 (1998)—Lovgren.
Database—GENESEQ Accession No. AED28321—(2005) Gramatikova.
Database—GENESEQ Accession No. AED28443 (2005)—Gramatikova.
Database—GNENSEQ Accession No. AEH47258 (2006)—Bornscheuer.
Database—NCBI Accession No. YP001643484—Phospholipase C—Sep. 24, 2004.
Dennis—Journal of Biological Chemistry (1994)—269—13057-13060.
Horstman—Archives of Biochemistry and Biophysics (1999)—361—149-155.
Rebecchi—Physiological Reviews (2000)—4—1291-1335.
Roberts—FASEB Journal (1996)—10—1159-1172.
Search report—AUIP—Sep. 23, 2009—Examiner's First Report—2005221136.
Search report—EP05727242—Supp. EP Search Report—Sep. 28, 2009.
Search report—EP07853585—Supplementary EP Search Report—Dec. 3, 2009.
Tan—Biochemistry (1998)—37—4275-4279.
Titball—Microbiological Reviews (1993)—57—347-366.
Takamiya—Trends in Plant Science (2000)—5—426-431.

\* cited by examiner

1 A

1 B

1 C

METHODS FOR ENZYMATIC DECOLORIZATION OF CHLOROPHYLL

CROSS REFERENCE TO RELATED APPLICATIONS

This application is a divisional of U.S. patent application Ser. No. 11/570,169, filed Nov. 2, 2007, currently pending; which is a National Stage Filing of International Application No.: PCT/US2005/032351, filed Sep. 9, 2005; which claims priority to U.S. Patent Application No. 60/609,125, filed Sep. 10, 2004, now expired; all of the above mentioned patents are hereby incorporated in their entirety and for all purposes.

REFERENCE TO SEQUENCE LISTING SUBMITTED VIA EFS-WEB

This application is being filed electronically via the USPTO EFS-WEB server, as authorized and set forth in MPEP §502.05 and this electronic filing includes an electronically submitted sequence listing; the entire content of this sequence listing is hereby incorporated by reference into the specification of this application. The sequence listing is identified on the electronically filed ASCII (.txt) text file as follows:

| File Name | Date of Creation | Size |
| --- | --- | --- |
| D12503ND1_SequenceListing | Aug. 19, 2011 | 51.1 KB (52,344 bytes) |

TECHNICAL FIELD

This invention relates to the fields of industrial processing of foods, feeds or vegetable oils, plant and animal products, and enzymology. In particular, the invention provides compositions and methods for the enzymatic treatment ("bleaching" or "de-colorizing") of chlorophyll-containing or chlorophyll-contaminated compositions, e.g., algal, animal or plant preparations, foods, feeds or oils, for example, vegetable oils, including oils processed from oilseeds, such as canola (rapeseed) oil or soybean oil, or oil fruits, such as palm oil. In one aspect, the invention provides methods using enzymes from chlorophyll catabolism (e.g., a chlorophyllase) for the enzymatic modification of a chlorophyll, e.g., in an algal, animal or plant preparation, or a food, a feed or an oil.

BACKGROUND

Vegetable oils coming from oilseeds such as canola or soybean or oilfruits such as palm contain chlorophyll. Chlorophyll is removed during many stages of the oil production process, including seed crushing, oil extraction, degumming, caustic treatment and bleaching steps. In the last of these, the bleaching process residual chlorophyll is removed to achieve acceptable levels. This chlorophyll is typically removed from the oil in a bleaching process step involving heating the oil and running it through an adsorbent to remove chlorophyll and other color-bearing compounds that impact the appearance and/or stability of the finished oil. This technology is also used to treat other chlorophyll-containing oils or plant or algal preparations, such as polyunsaturated fatty acid (PUFA) (e.g., eicosapentaenoic acid (EPA) and docosahexaenoic acid (DHA)) containing oils.

High level of chlorophyll pigments impart undesirable color and induce oxidation of oil during storage leading to a deterioration of the oil. In the edible oil processing industry, a bleaching step is employed to lower chlorophyll levels to as low as 0.1 ppm to guarantee oil quality in terms of color and organolepticity. Typical desired finished chlorophyll levels are between 0.02 to 0.05 ppm. This bleaching step increases processing cost and reduces oil yield due to entrainment in the bleaching clay.

In plants, chlorophyllase (chlase) is the first enzyme involved in chlorophyll degradation; it catalyzes the hydrolysis of an ester bond in chlorophyll to yield chlorophyllide and phytol.

SUMMARY

The invention provides compositions and methods for enzymatic treatment ("bleaching" or "de-colorizing") of chlorophyll-containing or chlorophyll-contaminated compositions such as plant, animals (e.g., fish, meat preparations) or algal preparations, foods, feeds or oils, such as polyunsaturated fatty acid (PUFA)-containing or docosahexaenoic acid (DHA)-containing oils, or compositions comprising mixtures thereof. In one aspect, the "enzymatic bleaching" of the compositions and methods of the invention comprises use of a chlorophyll modifying enzyme, e.g., a polypeptide having chlorophyllase activity, including chlases and chlorophyll chlorophyllido-hydrolyases, and related polypeptides, or any chlorophyll catabolic enzyme. Thus, as used herein, the term "enzymatic bleaching" includes any modification of a chlorophyll molecule or equivalent, including partial or complete decolorization. In one aspect, the compositions and methods of the invention can reduce yield loss from entrainment and fat splitting attributed to catalysis by clay/bleach conditions.

In alternative aspects of the methods and processes of the invention, a chlorophyllase, which can be a novel chlorophyllase of the invention, or a known enzyme, including chlases and chlorophyll chlorophyllido-hydrolyases and related polypeptides, or a combination thereof, or any chlorophyll catabolic enzyme, is added anytime or anywhere in the method or process, e.g., as discussed herein. For example, in one aspect, the chlorophyllase (which can be a novel chlorophyllase of the invention, or a known enzyme, or a combination thereof) and/or any chlorophyll catabolic enzyme can be added into a composition, such as a crude oil, with or without another enzyme, e.g., a phospholipase (e.g., phospholipase C) at a mixing step or in a degumming step, in a caustic tank step, in a static mixer, in a day tank or in a retention mixer. Alternatively, in one aspect of a method or process of the invention the chlorophyllase (of the invention, or known) and/or any chlorophyll catabolic enzyme can be added into any combination of these steps, or in all of these steps.

In one aspect, the invention provides methods or processes for enzymatic modification of chlorophyll to facilitate its removal from a composition, e.g., through an aqueous separation process, as illustrated in page 1, Appendix A, or hydrophobic separation process, or affinity separation process, and the like.

In one aspect the invention provides methods and processes comprising enzymatic modification (e.g., catabolism) of chlorophyll, or equivalent compounds, in a composition (e.g., a food, feed, plant, animal, algae, etc.) further comprising removal of components of that composition (e.g., compounds not desirable in a finished product), such as residual chlorophyll (e.g., chlorophyll or equivalent compounds not modified by a chlorophyllase), a pesticide, a polycyclic aromatic hydrocarbon, etc. Undesirable components, e.g., residual chlorophyll, pesticides, polycyclic aromatic hydrocarbons and the like, can be removed with either significantly smaller amounts of bleaching clay or other adsorbent, such as silica or equivalent compounds.

In one aspect, these components of the composition are removed using a bleaching clay, e.g., in a plurality of steps using bleaching clay, where in one aspect components of the composition are removed with either significantly smaller amounts of bleaching clay and/or at least one other adsorbent (e.g., a silica). In one aspect, finished chlorophyll levels are between about 0.02 ppm to 0.05 ppm. In this exemplary process, the bleaching step can increase processing costs and reduce oil yields due to entrainment in the bleaching clay. The compositions and processes of the invention can reduce yield loss from entrainment and fat splitting attributed to catalysis by clay/bleach conditions.

In an exemplary illustrated method (reaction) of the invention, a chlorophyllase catalyzes the hydrolysis of chlorophyll to generate chlorophyllide, which in one aspect is aqueous extracted, and phytol, which remains in the oil phase. In another exemplary method, pheophorbide can be removed in manner similar to chlorophyllide. In one aspect, by practicing the compositions and methods of the invention, an aqueous separation process can partially or completely eliminate the need for adsorbants. However, in another aspect, the methods comprise partial or complete extraction of the aqueous soluble chlorophyllide or pheophorbide using a silica-based extraction process (e.g., adsorbent-free or reduced adsorbent silica refining). In one aspect, the chlorophyllase is immobilized onto a silica (which then adsorbs the chlorophyllide), e.g., a silica gel. In one aspect, the silica comprises a TriSyl Silica or a SORBSIL R™ silica.

The invention provides methods, including industrial processes, for enzymatic treatment of pheophytin-containing or pheophytin-contaminated compositions comprising the following steps: (a) providing a pheophytin-containing or pheophytin-contaminated composition; (b) providing a polypeptide having a chlorophyllase or pheophytinase activity (which can be a novel chlorophyllase of the invention, or a known enzyme, or a combination thereof); and (c) reacting the composition of step (a) with the polypeptide of step (b) under conditions wherein the polypeptide can catalyze a pheophytin-modifying reaction. The magnesium-less derivative of chlorophyll is called pheophytin. Pheophytin is colored and often present in oil, especially if acid treatment has been used. In some applications, it is desirable to remove the pheophytin. The product of chlorophyllase treatment of pheophytin is pheophorbide, which can be removed in a similar manner to chlorophyllide.

In one aspect, the compositions and methods of the invention are practiced as or with industrial processes, e.g., oil bleaching or caustic neutralization or degumming processes. In one aspect, use of the compositions and methods of the invention facilitate reducing the amount of or eliminating the need for adsorbants in current bleaching processing, which typically involve heating the oil or other chlorophyll-containing composition and running it through an adsorbent to remove chlorophyll and other color-bearing compounds that impact the appearance and/or stability of the finished oil. Thus, in practicing this aspect of the invention, by partially or completely eliminate the need for adsorbants, processing costs can be decreased, e.g., adsorbents (e.g., clay) costs, disposal costs, water costs, energy costs, steam costs can be decreased. Other benefits in practicing various aspects of the invention include yield improvements, e.g., reduced entrained oils in adsorbent substrates, increased end product value, including retention of valuable micronutrients such as beta carotene, process efficiencies, including reduced processing steps, capital savings and an environmental benefit, e.g., reducing or eliminating land-filling of bleaching adsorbents.

In one aspect, in practicing the compositions and methods of the invention, the chlorophyll-modifying polypeptides (which can be a novel chlorophyllase of the invention, or a known enzyme, or a combination thereof) can be employed at any point in a degumming (e.g., enzymatic degumming) process. For example, the chlorophyll-modifying polypeptides can be added before or after any step in a process, or before or after any combination of steps, or before or after all of the steps, in a process, e.g., prior to, during or following mechanical and/or chemical extraction, and/or degumming and/or caustic neutralization and/or bleaching and the like.

In alternative aspects of any of the methods of the invention, at least one step is performed in a reaction vessel, e.g., an oil degumming apparatus. In alternative aspects of any of the methods of the invention, at least one step is performed in a cell extract. In alternative aspects of any of the methods of the invention, at least one step is performed in a whole cell. The cell can be of any source, e.g., a plant cell, a bacterial cell, a fungal cell, an animal cell (e.g., a mammalian cell, a fish cell) or a yeast cell.

The invention provides methods for enzymatic treatment of chlorophyll-containing or chlorophyll-contaminated compositions comprising the following steps: (a) providing a chlorophyll-containing or chlorophyll-contaminated composition (which can be a novel chlorophyllase of the invention, or a known enzyme, or a combination thereof); (b) providing a polypeptide having a chlorophyllase activity; and (c) reacting the composition of step (a) with the polypeptide of step (b) under conditions wherein the polypeptide can catalyze a chlorophyll-modifying reaction.

The invention provides industrial processes for enzymatic treatment ("bleaching") of chlorophyll-containing or chlorophyll-contaminated compositions comprising the following steps: (a) providing a chlorophyll-containing or chlorophyll-contaminated composition (which can be a novel chlorophyllase of the invention, or a known enzyme, or a combination thereof); (b) providing a polypeptide having chlorophyllase activity; and (c) reacting the composition of step (a) with the polypeptide of step (b) under conditions wherein the polypeptide can catalyze a chlorophyll-modifying reaction.

The invention provides degumming processes comprising a step for enzymatic bleaching of chlorophyll-containing or chlorophyll-contaminated compositions comprising the following steps: (a) providing a chlorophyll-containing or chlorophyll-contaminated composition (which can be a novel chlorophyllase of the invention, or a known enzyme, or a combination thereof); (b) providing a polypeptide having chlorophyllase activity; and (c) reacting the composition of step (a) with the polypeptide of step (b) under conditions wherein the polypeptide can catalyze a chlorophyll-modifying reaction.

There is a second ester on chlorophylls and pheophytins—a methyl ester. The methods of the invention can further comprise hydrolysis of this methyl ester by an esterase. This can increase the tendency of the reaction derivative (now a diacid) to partition into an aqueous layer.

In an exemplary method, a phospholipase, e.g., a phospholipase C, or another hydrolase (e.g., a cellulase, a hemicellulase, an esterase, a protease and/or a phosphatase) is used, e.g., to improve oil extraction and oil degumming.

In alternative aspects, the methods and processes of the invention can further comprise hydrolysis of methyl ester on a chlorophyll or a pheophytin by an esterase (which can be a novel enzyme of the invention, or a known enzyme, or a combination thereof). In alternative aspects, the methods of the invention can further comprise removal of the modified chlorophyll in an aqueous extraction. The methods can further comprise modifying pH (e.g., increasing pH) to promote aqueous separation of chlorophyllide. The enzymes used in the methods, e.g., a chlorophyllase, can be added during this increased pH, or "caustic" phase in the separation process. The methods can further comprise a caustic neutralization step. The methods can further comprise an adsorbent-free or reduced adsorbent silica refining step to remove a chlorophilide generated by the enzymatic degradation of the chlorophyll. The methods can further comprise use of a hydrolase, e.g., a phospholipase C.

In one aspect of the methods and processes, the polypeptide is an esterase (e.g., an enzyme of the invention), e.g., a chlorophyllase, or has chlorophyllase-like activity, or has chlorophyll catabolic activity. In one aspect of the methods, the polypeptide is immobilized. The polypeptide can be immobilized on an inorganic support or organic support. The inorganic support can comprise alumina, celite, Dowex-1-chloride, glass beads or silica gel or equivalent. The polypeptide can be immobilized on an alginate hydrogel or alginate bead or equivalent. In one aspect of the methods, the polypeptide further comprises a liposome, a hydrogel or a gel.

In one aspect of the methods, the polypeptide is at least one step is performed in a reaction vessel, e.g., a vessel comprising a gravitational gum separation device or a holding tank or the like. In one aspect of the methods, at least one step is performed in a cell extract, or a whole cell. The cell can be a plant cell, a bacterial cell, a fungal cell, a yeast cell, a mammalian cell, an insect cell and the like.

In one aspect of the methods, the chlorophyll-containing or chlorophyll-contaminated composition comprises a plant material, plant oil or plant extract. The plant material, plant oil or plant extract can comprise a vegetable oil or a seed oil. The vegetable oil can comprise a palm oil or a canola oil. Alternatively, the plant material, plant oil or plant extract can comprise an algal preparation. In one aspect of the methods, the chlorophyll-containing or chlorophyll-contaminated compositions comprise a non-wood or wood product. In one aspect of the methods, the chlorophyll-containing or chlorophyll-contaminated compositions comprise a fabric or cloth. In one aspect of the methods, the chlorophyll-containing or chlorophyll-contaminated compositions comprise a pharmaceutical formulation, a food, an oil, a feed, or a dietary supplement.

The compositions and methods of the invention can be used to treat crude or refined oils, e.g., oils derived from plant (e.g., vegetable), algae, animal or fish, or synthetic, sources. The compositions and methods of the invention can be used to treat crude or refined oils at higher oil concentrations, or, in one aspect, used to treat unrefined and non-diluted crude oils.

In one aspect the methods further comprise removal of a chlorophilide generated by enzymatic degradation of a chlorophyll by adsorbing onto a silica gel or equivalent. The chlorophyll-containing or chlorophyll-contaminated compositions can comprise a textile, cloth, thread or fabric or related composition, a wood or paper product or by-product, such as a wood pulp, a paper pulp, a Kraft pulp, or, a non-wood paper product or by-product, such as a rice paper.

The invention provides products of manufacture comprising a degumming system for the enzymatic treatment of chlorophyll-containing or chlorophyll-contaminated compositions comprising: (a) a vegetable oil refining apparatus; and (b) a polypeptide having chlorophyllase activity (e.g., an enzyme of the invention), wherein the activity of the polypeptide comprises catalysis of a chlorophyll-modifying reaction, and the vegetable oil refining apparatus can react a chlorophyll-containing or chlorophyll-contaminated composition with the polypeptide to under conditions wherein the polypeptide can catalyze a chlorophyll-modifying reaction. In one aspect of the product of manufacture, the vegetable oil refining apparatus comprises an oil leaving expellor, a holding tank or a gravitational gum separation device. The chlorophyll-modifying reactions can comprise generation of chlorophyllide and phytol.

The invention provides detergents comprising an enzymatic treatment of chlorophyll-containing or chlorophyll-contaminated fabrics comprising: (a) a detergent composition; and (b) a polypeptide having chlorophyllase activity (e.g., an enzyme of the invention), wherein the activity comprises catalysis of a chlorophyll-modifying reaction. In one aspect, the chlorophyll-modifying reaction comprises generation of chlorophyllide and phytol.

The invention provides methods for enzymatically treating a chlorophyll-containing or chlorophyll-contaminated fabrics comprising: (a) providing a detergent composition comprising a polypeptide having chlorophyllase activity (e.g., an enzyme of the invention), wherein the activity comprises catalysis of a chlorophyll-modifying reaction; and, (b) contacting the detergent composition with the chlorophyll-containing or chlorophyll-contaminated fabric under conditions wherein the polypeptide can catalyze a chlorophyll-modifying reaction. In one aspect, the chlorophyll-modifying reaction comprises generation of chlorophyllide and phytol.

The invention provides isolated, synthetic or recombinant nucleic acids comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention, e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19, over a region of at least about 10, 15, 20, 25, 30, 35, 40, 45, 50, 55, 60, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more residues, sequences substantially identical thereto, and the sequences complementary thereto, and encodes at least one polypeptide having an enzymatic activity as described herein, e.g., an esterase enzyme activity.

In alternative aspects, the sequence identities are determined by analysis with a sequence comparison algorithm or by a visual inspection. In one aspect, the sequence comparison algorithm is a BLAST algorithm, e.g., a BLAST version 2.2.2 algorithm where a filtering setting is set to blastall -p blastp -d "nr pataa" -F F, and all other options are set to default.

Exemplary nucleic acids of the invention also include isolated, synthetic or recombinant nucleic acids encoding a polypeptide of the invention, e.g., a polypeptide having a sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20, and subsequences thereof and variants thereof.

In alternative aspects, the polypeptide has an esterase enzyme activity, including chlorophyllase (a chlase) activity, or, enzyme activity comprising enzymatic modification of a chlorophyll molecule, e.g., wherein the enzymatic modification comprises catabolism of the chlorophyll molecule. In one aspect, the esterase activity comprises a chlorophyll chlorophyllido-hydrolyase activity.

In one aspect, the isolated, synthetic or recombinant nucleic acid of the invention encodes a polypeptide having an enzyme activity that is thermostable. The polypeptide can retain enzyme activity under conditions comprising a temperature range of between about 37° C. to about 95° C.; between about 55° C. to about 85° C., between about 70° C. to about 95° C., or, between about 90° C. to about 95° C.

In another aspect, an isolated, synthetic or recombinant nucleic acid of the invention encodes a polypeptide having enzyme that is thermotolerant. The polypeptide can retain enzyme activity after exposure to a temperature in the range from greater than 37° C. to about 95° C. or anywhere in the range from greater than 55° C. to about 85° C. The polypeptide can retain enzyme activity after exposure to a temperature in the range between about 1° C. to about 5° C., between about 5° C. to about 15° C., between about 15° C. to about 25° C., between about 25° C. to about 37° C., between about 37° C. to about 95° C., between about 55° C. to about 85° C., between about 70° C. to about 75° C., or between about 90° C. to about 95° C., or more. In one aspect, the polypeptide retains enzyme activity after exposure to a temperature in the range from greater than 90° C. to about 95° C. at pH 4.5.

The invention provides isolated, synthetic or recombinant nucleic acids comprising a sequence that hybridizes under stringent conditions to a nucleic acid comprising a sequence of the invention, e.g., a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19, or fragments or subsequences thereof (or complements thereof). In one aspect, the nucleic acid of the invention encodes a polypeptide having an esterase enzyme activity, including chlorophyllase (a chlase) activity, or, enzyme activity comprising enzymatic modification of a chlorophyll molecule, e.g., wherein the enzymatic modification comprises catabolism of the chlorophyll molecule. In one aspect, the esterase activity comprises a chlorophyll chlorophyllido-hydrolyase activity. The nucleic acid can be at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200 or more residues in length or the full length of the gene or transcript. In one aspect, the stringent conditions include a wash step comprising a wash in 0.2×SSC at a temperature of about 65° C. for about 15 minutes.

The invention provides a nucleic acid probe for identifying a nucleic acid encoding a polypeptide having an enzyme activity as described herein (e.g., esterase enzyme activity, including chlorophyllase (a chlase) activity), wherein the probe comprises at least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000 or more, consecutive bases of a sequence comprising a sequence of the invention, or fragments or subsequences thereof, wherein the probe identifies the nucleic acid by binding or hybridization. The probe can comprise an oligonucleotide comprising at least about 10 to 50, about 20 to 60, about 30 to 70, about 40 to 80, or about 60 to 100 consecutive bases of a sequence comprising a sequence of the invention, or fragments or subsequences thereof.

The invention provides a nucleic acid probe for identifying a nucleic acid encoding a polypeptide having at least one enzyme activity as described herein (e.g., esterase enzyme activity, including chlorophyllase (a chlase) activity), wherein the probe comprises a nucleic acid comprising a sequence at least about 10, 15, 20, 30, 40, 50, 60, 70, 80, 90, 100, 150, 200, 250, 300, 350, 400, 450, 500, 550, 600, 650, 700, 750, 800, 850, 900, 950, 1000 or more residues having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a nucleic acid of the invention, wherein the sequence identities are determined by analysis with a sequence comparison algorithm or by visual inspection.

The probe can comprise an oligonucleotide comprising at least about 10 to 50, about 20 to 60, about 30 to 70, about 40 to 80, or about 60 to 100 consecutive bases of a nucleic acid sequence of the invention, or a subsequence thereof.

The invention provides an amplification primer pair for amplifying a nucleic acid encoding a polypeptide having at least one enzyme activity as described herein (e.g., esterase enzyme activity, including chlorophyllase (a chlase) activity), wherein the primer pair is capable of amplifying a nucleic acid comprising a sequence of the invention, or fragments or subsequences thereof. One or each member of the amplification primer sequence pair can comprise an oligonucleotide comprising at least about 10 to 50 consecutive bases of the sequence, or about 10, 11, 12, 13, 14, 15, 16, 17, 18, 19, 20, 21, 22, 23, 24, 25, 26, 27, 28, 29, 30 or more consecutive bases of the sequence.

The invention provides amplification primer pairs, wherein the primer pair comprises a first member having a sequence as set forth by about the first (the 5') 12, 13, 14, 15, 16, 17, 18, 19, 20, 21, 22, 23, 24, 25, 26, 27, 28, 29, 30 or more residues of a nucleic acid of the invention, and a second member having a sequence as set forth by about the first (the 5') 12, 13, 14, 15, 16, 17, 18, 19, 20, 21, 22, 23, 24, 25, 26, 27, 28, 29, 30 or more residues of the complementary strand of the first member.

The invention provides nucleic acids encoding proteins (e.g., enzymes), including the polypeptides of the invention, generated by amplification, e.g., polymerase chain reaction (PCR), using an amplification primer pair of the invention. The invention provides nucleic acids encoding polypeptides having at least one enzyme activity as described herein (e.g., esterase enzyme activity, including chlorophyllase (a chlase) activity) using an amplification primer pair of the invention. The invention provides methods of making and/or identifying enzymes by amplification, e.g., polymerase chain reaction (PCR), using an amplification primer pair of the invention. In one aspect, the amplification primer pair amplifies a nucleic acid from a library, e.g., a gene library, such as an environmental library.

The invention provides methods of amplifying a nucleic acid encoding a polypeptide having enzyme activity comprising amplification of a template nucleic acid with an amplification primer sequence pair capable of amplifying a nucleic acid sequence of the invention, or fragments or subsequences thereof.

The invention provides expression cassettes comprising a nucleic acid of the invention or a subsequence thereof. In one aspect, the expression cassette can comprise the nucleic acid that is operably linked to a promoter. The promoter can be a viral, bacterial, mammalian or plant promoter. In one aspect, the plant promoter can be a potato, rice, corn, wheat, tobacco or barley promoter. The promoter can be a constitutive promoter. The constitutive promoter can comprise CaMV35S. In another aspect, the promoter can be an inducible promoter. In one aspect, the promoter can be a tissue-specific promoter or an environmentally regulated or a developmentally regulated promoter. Thus, the promoter can be, e.g., a seed-specific, a leaf-specific, a root-specific, a stem-specific or an abscission-induced promoter. In one aspect, the expression cassette can further comprise a plant or plant virus expression vector.

The invention provides cloning vehicles comprising an expression cassette (e.g., a vector) of the invention or a nucleic acid of the invention. The cloning vehicle can be a viral vector, a plasmid, a phage, a phagemid, a cosmid, a fosmid, a bacteriophage or an artificial chromosome. The viral vector can comprise an adenovirus vector, a retroviral vector or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC).

The invention provides transformed cell comprising a nucleic acid of the invention or an expression cassette (e.g., a vector) of the invention, or a cloning vehicle of the invention. In one aspect, the transformed cell can be a bacterial cell, a mammalian cell, a fungal cell, a yeast cell, an insect cell or a plant cell. In one aspect, the plant cell can be a cereal, a potato, wheat, rice, corn, tobacco or barley cell.

The invention provides transgenic non-human animals comprising a nucleic acid of the invention or an expression cassette (e.g., a vector) of the invention. In one aspect, the animal is a mouse.

The invention provides transgenic plants comprising a nucleic acid of the invention or an expression cassette (e.g., a vector) of the invention. The transgenic plant can be a cereal plant, a corn plant, a potato plant, a tomato plant, a wheat plant, an oilseed plant, a rapeseed plant, a soybean plant, a rice plant, a barley plant or a tobacco plant.

The invention provides transgenic seeds comprising a nucleic acid of the invention or an expression cassette (e.g., a vector) of the invention. The transgenic seed can be a cereal plant, a corn seed, a wheat kernel, an oilseed, a rapeseed, a soybean seed, a palm kernel, a sunflower seed, a sesame seed, a peanut or a tobacco plant seed.

The invention provides an antisense oligonucleotide comprising a nucleic acid sequence complementary to or capable of hybridizing under stringent conditions to a nucleic acid of the invention. The invention provides methods of inhibiting the translation of a enzyme message (of an enzyme of the invention) in a cell comprising administering to the cell or expressing in the cell an antisense oligonucleotide comprising a nucleic acid sequence complementary to or capable of hybridizing under stringent conditions to a nucleic acid of the invention. In one aspect, the antisense oligonucleotide is between about 10 to 50, about 20 to 60, about 30 to 70, about 40 to 80, or about 60 to 100 bases in length.

The invention provides methods of inhibiting the translation of an enzyme message in a cell comprising administering to the cell or expressing in the cell an antisense oligonucleotide comprising a nucleic acid sequence complementary to or capable of hybridizing under stringent conditions to a nucleic acid of the invention. The invention provides double-stranded inhibitory RNA (RNAi) molecules comprising a subsequence of a sequence of the invention. In one aspect, the RNAi is about 15, 16, 17, 18, 19, 20, 21, 22, 23, 24, 25 or more duplex nucleotides in length. The invention provides methods of inhibiting the expression of a polypeptide (e.g., an enzyme of the invention) in a cell comprising administering to the cell or expressing in the cell a double-stranded inhibitory RNA (iRNA), wherein the RNA comprises a subsequence of a sequence of the invention.

The invention provides an isolated, synthetic or recombinant polypeptide comprising an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptide or peptide of the invention over a region of at least about 20, 25, 30, 35, 40, 45, 50, 55, 60, 65, 70, 75, 100, 125, 150, 175, 200, 225, 250, 275, 300, 325, 350 or more residues, or over the full length of the polypeptide. In one aspect, the sequence identities are determined by analysis with a sequence comparison algorithm or by a visual inspection. Exemplary polypeptide or peptide sequences of the invention include SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20, and subsequences thereof and variants thereof. Exemplary polypeptides also include fragments of at least about 10, 15, 20, 25, 30, 35, 40, 45, 50, 75, 80, 85, 90, 95, 100, 150, 200, 250, 300, 350, 400, 450, 500, 550, 600 or more residues in length, or over the full length of an enzyme. Exemplary polypeptide or peptide sequences of the invention include sequence encoded by a nucleic acid of the invention. Exemplary polypeptide or peptide sequences of the invention include polypeptides or peptides specifically bound by an antibody of the invention. The peptide can be, e.g., an immunogenic fragment, a motif (e.g., a binding site), a signal sequence, a prepro sequence, a catalytic domains (CDs) or an active site.

In one aspect, a polypeptide of the invention has an esterase activity, such as a chlorophyllase (a chlase) activity, or, has an enzyme activity comprising enzymatic modification of a chlorophyll molecule, e.g., wherein the enzymatic modification comprises catabolism of the chlorophyll molecule. In one aspect, the esterase activity comprises a chlorophyll chlorophyllido-hydrolyase activity.

Another aspect of the invention provides an isolated, synthetic or recombinant polypeptide or peptide including at least 10, 15, 20, 25, 30, 35, 40, 45, 50, 55, 60, 65, 70, 75, 80, 85, 90, 95 or 100 or more consecutive bases of a polypeptide or peptide sequence of the invention, sequences substantially identical thereto, and the sequences complementary thereto. The peptide can be, e.g., an immunogenic fragment, a motif (e.g., a binding site), a signal sequence, a prepro sequence or a catalytic domains (CDs) or active site.

The invention provides biosynthetic systems comprising nucleic acids and/or plasmids of the invention in a cell, e.g., a yeast cell, a plant cell, a fungal cell, or a microbial (e.g., bacterial) cell. In one aspect, the biosynthetic systems of the invention comprise coding sequences for all the enzymes necessary, or a subset thereof, for catabolism of a chlorophyll molecule. In one aspect, the coding sequences can be in a plasmid, a recombinant vector or virus and the like.

In one aspect, the enzyme activity of a polypeptide of the invention is thermostable. The polypeptide of the invention can retain activity under conditions comprising a temperature range of between about 1° C. to about 5° C., between about 5° C. to about 15° C., between about 15° C. to about 25° C., between about 25° C. to about 37° C., between about 37° C. to about 95° C., between about 55° C. to about 85° C., between about 70° C. to about 75° C., or between about 90° C. to about 95° C., or more. In another aspect, the enzyme activity of a polypeptide of the invention is thermotolerant. The polypeptide can retain activity after exposure to a temperature in the range from greater than 37° C. to about 95° C., or in the range from greater than 55° C. to about 85° C. In one aspect, the polypeptide can retain activity after exposure to a temperature in the range from greater than 90° C. to about 95° C. at pH 4.5.

In one aspect, the isolated, synthetic or recombinant polypeptide can comprise the polypeptide of the invention that lacks a signal sequence. In one aspect, the isolated, synthetic or recombinant polypeptide can comprise the polypeptide of the invention comprising a heterologous signal sequence.

In one aspect, the invention provides chimeric proteins comprising a first domain comprising a signal sequence of the invention and at least a second domain. The protein can be a fusion protein. The second domain can comprise an enzyme. The chimeric enzyme can comprise all or a subsequence of at least one polypeptide having an activity as described herein (e.g., esterase enzyme activity, including chlorophyllase (a chlase) activity).

The invention provides chimeric polypeptides comprising at least a first domain comprising signal peptide (SP), a prepro sequence and/or a catalytic domain (CD) of the invention and at least a second domain comprising a heterologous polypeptide or peptide, wherein the heterologous polypeptide or peptide is not naturally associated with the signal peptide (SP), prepro sequence and/or catalytic domain (CD). In one aspect, the heterologous polypeptide or peptide is not a polypeptide having activity comprising esterase enzyme activity or chlorophyll catabolism activity. The heterologous polypeptide or peptide can be amino terminal to, carboxy terminal to or on both ends of the signal peptide (SP), prepro sequence and/or catalytic domain (CD).

The invention provides isolated, synthetic or recombinant nucleic acids encoding a chimeric polypeptide, wherein the chimeric polypeptide comprises at least a first domain comprising signal peptide (SP), a prepro domain and/or a catalytic domain (CD) of the invention and at least a second domain comprising a heterologous polypeptide or peptide, wherein the heterologous polypeptide or peptide is not naturally associated with the signal peptide (SP), prepro domain and/or catalytic domain (CD).

The invention provides isolated, synthetic or recombinant signal sequences (e.g., signal peptides) consisting of or comprising a sequence as set forth in residues 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 40, 1 to 41, 1 to 42, 1 to 43 or 1 to 44, of a polypeptide of the invention, e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20. The invention provides isolated, synthetic or recombinant signal sequences (e.g., signal peptides) consisting of or comprising a sequence as set forth in Table 1, below.

In one aspect, an enzyme of the invention has a specific activity at about 37° C. in the range from about 1 to about 1200 units per milligram of protein, or, about 100 to about 1000 units per milligram of protein. In another aspect, an enzyme of the invention has a specific activity from about 100 to about 1000 units per milligram of protein, or, from about 500 to about 750 units per milligram of protein. Alternatively, an enzyme of the invention has a specific activity at 37° C. in the range from about 1 to about 750 units per milligram of protein, or, from about 500 to about 1200 units per milligram of protein. In one aspect, an enzyme of the invention has a specific activity at 37° C. in the range from about 1 to about 500 units per milligram of protein, or, from about 750 to about 1000 units per milligram of protein. In another aspect, an enzyme of the invention has a specific activity at 37° C. in the range from about 1 to about 250 units per milligram of protein. Alternatively, an enzyme of the invention has comprises a specific activity at 37° C. in the range from about 1 to about 100 units per milligram of protein. In another aspect, the thermotolerance comprises retention of at least half of the specific activity of the enzyme at 37° C. after being heated to the elevated temperature. Alternatively, the thermotolerance can comprise retention of specific activity at 37° C. in the range from about 1 to about 1200 units per milligram of protein, or, from about 500 to about 1000 units per milligram of protein, after being heated to the elevated temperature. In another aspect, the thermotolerance can comprise retention of specific activity at 37° C. in the range from about 1 to about 500 units per milligram of protein after being heated to the elevated temperature.

The invention provides an isolated, synthetic or recombinant polypeptide of the invention, wherein the polypeptide comprises at least one glycosylation site. In one aspect, glycosylation can be an N-linked glycosylation. In one aspect, the polypeptide can be glycosylated after being expressed in a P. pastoris or a S. pombe.

In one aspect, a polypeptide of the invention can retain enzyme activity under conditions comprising about pH 6.5, pH 6, pH 5.5, pH 5, pH 4.5 or pH 4 or more acidic. In another aspect, a polypeptide of the invention retains activity under conditions comprising about pH 7, pH 7.5 pH 8.0, pH 8.5, pH 9, pH 9.5, pH 10, pH 10.5 or pH 11 or more basic. In one aspect, a polypeptide of the invention retains activity under conditions comprising about pH 6.5, pH 6, pH 5.5, pH 5, pH 4.5 or pH 4 or more acidic. In another aspect, a polypeptide of the invention retains activity under conditions comprising about pH 7, pH 7.5 pH 8.0, pH 8.5, pH 9, pH 9.5, pH 10, pH 10.5 or pH 11 or more basic.

The invention provides protein preparations comprising a polypeptide of the invention, wherein the protein preparation comprises a liquid, a solid or a gel.

The invention provides heterodimers comprising a polypeptide of the invention and a second protein or domain. In one aspect, the second member of the heterodimer is not a polypeptide of the invention but rather is a different enzyme or another protein. In one aspect, the second domain can be a polypeptide and the heterodimer can be a fusion protein. In one aspect, the second domain can be an epitope or a tag. In one aspect, the invention provides homodimers comprising a polypeptide of the invention.

The invention provides immobilized polypeptides of the invention, a polypeptide encoded by a nucleic acid of the invention, or a polypeptide comprising a polypeptide of the invention and a second domain. In one aspect, the polypeptide can be immobilized on a cell, a metal, a resin, a polymer, a ceramic, a glass, a microelectrode, a graphitic particle, a bead, a gel, a plate, an array or a capillary tube.

The invention provides arrays comprising an immobilized nucleic acid of the invention. The invention provides arrays comprising an antibody of the invention.

The invention provides isolated, synthetic or recombinant antibodies that specifically bind to a polypeptide of the invention or to a polypeptide encoded by a nucleic acid of the invention. The antibody can be a monoclonal or a polyclonal antibody. The invention provides hybridomas comprising an antibody of the invention, e.g., an antibody that specifically binds to a polypeptide of the invention or to a polypeptide encoded by a nucleic acid of the invention.

The invention provides method of isolating or identifying a polypeptide involved in chlorophyll catabolism or having an esterase (e.g., chlorophyllase) activity, wherein the method comprises the steps of: (a) providing an antibody of the invention; (b) providing a sample comprising polypeptides; and (c) contacting the sample of step (b) with the antibody of step (a) under conditions wherein the antibody can specifically bind to the polypeptide, thereby isolating or identifying the polypeptide.

The invention provides methods of making an antibody that specifically binds to a polypeptide of the invention (e.g., an enzyme or another antibody of the invention) comprising administering to a non-human animal a nucleic acid of the invention or a polypeptide of the invention or subsequences thereof in an amount sufficient to generate a humoral immune response, thereby generating an antibody response. The invention provides methods of making a humoral or cellular immune response comprising administering to a non-human animal a nucleic acid of the invention or a polypeptide of the invention or subsequences thereof in an amount sufficient to generate an immune response.

The invention provides methods of producing a recombinant polypeptide comprising the steps of: (a) providing a nucleic acid of the invention operably linked to a promoter; and (b) expressing the nucleic acid of step (a) under conditions that allow expression of the polypeptide, thereby producing a recombinant polypeptide. In one aspect, the method can further comprise transforming a host cell with the nucleic acid of step (a) followed by expressing the nucleic acid of step (a), thereby producing a recombinant polypeptide in a transformed cell.

The invention provides methods for identifying a polypeptide involved in chlorophyll catabolism or having an esterase (e.g., chlorophyllase) activity, comprising the following steps: (a) providing a polypeptide of the invention; or a polypeptide encoded by a nucleic acid of the invention; (b) providing an appropriate substrate (e.g., substrate of the polypeptide; and (c) contacting the polypeptide or a fragment or variant thereof of step (a) with the substrate of step (b) and detecting a decrease in the amount of substrate or an increase in the amount of a reaction product, wherein a decrease in the amount of the substrate or an increase in the amount of the reaction product detects a polypeptide involved in chlorophyll catabolism or having an esterase (e.g., chlorophyllase) activity.

The invention provides methods for identifying a substrate of a polypeptide involved in a chlorophyll catabolism or having an esterase (e.g., chlorophyllase) activity, wherein the method comprises the following steps: (a) providing a polypeptide of the invention; or a polypeptide encoded by a nucleic acid of the invention; (b) providing a test substrate; and (c) contacting the polypeptide of step (a) with the test substrate of step (b) and detecting a decrease in the amount of substrate or an increase in the amount of reaction product, wherein a decrease in the amount of the substrate or an increase in the amount of a reaction product identifies the test substrate a substrate of a polypeptide involved in chlorophyll catabolism or having an esterase (e.g., chlorophyllase) activity.

The invention provides methods of determining whether a test compound specifically binds to a polypeptide comprising the following steps: (a) expressing a nucleic acid or a vector comprising the nucleic acid under conditions permissive for translation of the nucleic acid to a polypeptide, wherein the nucleic acid comprises a nucleic acid of the invention, or, providing a polypeptide of the invention; (b) providing a test compound; (c) contacting the polypeptide with the test compound; and (d) determining whether the test compound of step (b) specifically binds to the polypeptide.

The invention provides methods for identifying a modulator of a polypeptide involved in chlorophyll catabolism or having an esterase (e.g., chlorophyllase) activity, comprising the following steps: (a) providing a polypeptide of the invention or a polypeptide encoded by a nucleic acid of the invention; (b) providing a test compound; (c) contacting the polypeptide of step (a) with the test compound of step (b) and measuring an activity of the polypeptide wherein a change in activity measured in the presence of the test compound compared to the activity in the absence of the test compound provides a determination that the test compound modulates polypeptide activity. In one aspect, polypeptide activity can be measured by providing an appropriate substrate (e.g., substrate of the polypeptide involved in a chlorophyll catabolism or having an esterase (e.g., chlorophyllase) activity) and detecting a decrease in the amount of the substrate or an increase in the amount of a reaction product, or, an increase in the amount of the substrate or a decrease in the amount of a reaction product. A decrease in the amount of the substrate or an increase in the amount of the reaction product with the test compound as compared to the amount of substrate or reaction product without the test compound identifies the test compound as an activator of activity. An increase in the amount of the substrate or a decrease in the amount of the reaction product with the test compound as compared to the amount of substrate or reaction product without the test compound identifies the test compound as an inhibitor of activity.

The invention provides computer systems comprising a processor and a data storage device wherein said data storage device has stored thereon a polypeptide sequence or a nucleic acid sequence of the invention (e.g., a polypeptide encoded by a nucleic acid of the invention). In one aspect, the computer system can further comprise a sequence comparison algorithm and a data storage device having at least one reference sequence stored thereon. In another aspect, the sequence comparison algorithm comprises a computer program that indicates polymorphisms. In one aspect, the computer system can further comprise an identifier that identifies one or more features in said sequence. The invention provides computer readable media having stored thereon a polypeptide sequence or a nucleic acid sequence of the invention. The invention provides methods for identifying a feature in a sequence comprising the steps of: (a) reading the sequence using a computer program which identifies one or more features in a sequence, wherein the sequence comprises a polypeptide sequence or a nucleic acid sequence of the invention; and (b) identifying one or more features in the sequence with the computer program. The invention provides methods for comparing a first sequence to a second sequence comprising the steps of: (a) reading the first sequence and the second sequence through use of a computer program which compares sequences, wherein the first sequence comprises a polypeptide sequence or a nucleic acid sequence of the invention; and (b) determining differences between the first sequence and the second sequence with the computer program. The step of determining differences between the first sequence and the second sequence can further comprise the step of identifying polymorphisms. In one aspect, the method can further comprise an identifier that identifies one or more features in a sequence. In another aspect, the method can comprise reading the first sequence using a computer program and identifying one or more features in the sequence.

The invention provides methods for isolating or recovering a nucleic acid encoding a polypeptide having enzymatic activity involved in chlorophyll catabolism or having an esterase (e.g., chlorophyllase) activity from an environmental sample comprising the steps of: (a) providing an amplification primer sequence pair for amplifying a nucleic acid encoding a polypeptide involved in chlorophyll catabolism or having an esterase (e.g., chlorophyllase) activity, wherein the primer pair is capable of amplifying a nucleic acid of the invention; (b) isolating a nucleic acid from the environmental sample or treating the environmental sample such that nucleic acid in the sample is accessible for hybridization to the amplification primer pair; and, (c) combining the nucleic acid of step (b) with the amplification primer pair of step (a) and amplifying nucleic acid from the environmental sample, thereby isolating or recovering a nucleic acid encoding a polypeptide involved in chlorophyll catabolism or having an esterase (e.g., chlorophyllase) activity from an environmental sample. In one aspect, one or each member of the amplification primer pair can comprise an oligonucleotide comprising at least about 10 to 50 or more consecutive bases of a sequence of the invention. In one aspect, the amplification primer pair is an amplification pair of the invention.

The invention provides methods for isolating or recovering a nucleic acid encoding a polypeptide involved in chlorophyll catabolism or having an esterase (e.g., chlorophyllase) activity from an environmental sample comprising the steps of: (a) providing a polynucleotide probe comprising a nucleic acid of the invention or a subsequence thereof; (b) isolating a nucleic acid from the environmental sample or treating the environmental sample such that nucleic acid in the sample is accessible for hybridization to a polynucleotide probe of step (a); (c) combining the isolated, synthetic nucleic acid or the treated environmental sample of step (b) with the polynucleotide probe of step (a); and (d) isolating a nucleic acid that specifically hybridizes with the polynucleotide probe of step (a), thereby isolating or recovering a nucleic acid encoding a polypeptide involved in chlorophyll catabolism or having an esterase (e.g., chlorophyllase) activity from an environmental sample. The environmental sample can comprise a water sample, a liquid sample, a soil sample, an air sample or a biological sample. In one aspect, the biological sample can be derived from a bacterial cell, a protozoan cell, an insect cell, a yeast cell, a plant cell, a fungal cell or a mammalian cell.

The invention provides methods of generating a variant of a nucleic acid encoding a polypeptide involved in chlorophyll catabolism or having an esterase (e.g., chlorophyllase) activity comprising the steps of: (a) providing a template nucleic acid comprising a nucleic acid of the invention; and (b) modifying, deleting or adding one or more nucleotides in the template sequence, or a combination thereof, to generate a variant of the template nucleic acid. In one aspect, the method can further comprise expressing the variant nucleic acid to generate a variant polypeptide involved in chlorophyll catabolism or having an esterase (e.g., chlorophyllase) activity. The modifications, additions or deletions can be introduced by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis (GSSM), synthetic ligation reassembly (SLR) or a combination thereof. In another aspect, the modifications, additions or deletions are introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

In one aspect, the method can be iteratively repeated until a polypeptide involved in chlorophyll catabolism or having an esterase (e.g., chlorophyllase) activity having an altered or different activity or an altered or different stability from that of a polypeptide encoded by the template nucleic acid is produced. In one aspect, the variant polypeptide is thermotolerant, and retains some activity after being exposed to an elevated temperature. In another aspect, the variant polypeptide has increased glycosylation as compared to the polypeptide encoded by a template nucleic acid. Alternatively, the variant polypeptide has activity under a high (or higher) temperature, wherein the enzyme encoded by the template nucleic acid is not active under the high temperature. In one aspect, the method can be iteratively repeated until an enzyme coding sequence having an altered codon usage from that of the template nucleic acid is produced. In another aspect, the method can be iteratively repeated until an enzyme-encoding gene having higher or lower level of message expression or stability from that of the template nucleic acid is produced.

The invention provides methods for modifying codons in a nucleic acid encoding a polypeptide involved in chlorophyll catabolism or having an esterase (e.g., chlorophyllase) activity to increase its expression in a host cell, the method comprising the following steps: (a) providing a nucleic acid of the invention encoding a polypeptide involved in chlorophyll catabolism or having an esterase (e.g., chlorophyllase) activity; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying codons in a nucleic acid encoding a polypeptide involved in chlorophyll catabolism or having an esterase (e.g., chlorophyllase) activity; the method comprising the following steps: (a) providing a nucleic acid of the invention; and, (b) identifying a codon in the nucleic acid of step (a) and replacing it with a different codon encoding the same amino acid as the replaced codon, thereby modifying codons in a nucleic acid encoding the polypeptide.

The invention provides methods for modifying codons in a nucleic acid encoding a polypeptide having enzymatic activity involved in chlorophyll catabolism or having an esterase (e.g., chlorophyllase) activity to increase its expression in a host cell, the method comprising the following steps: (a) providing a nucleic acid of the invention encoding a polypeptide having enzymatic activity involved in chlorophyll catabolism or having an esterase (e.g., chlorophyllase) activity; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying a codon in a nucleic acid encoding a polypeptide having enzymatic activity involved in chlorophyll catabolism or having an esterase (e.g., chlorophyllase) activity to decrease its expression in a host cell, the method comprising the following steps: (a) providing a nucleic acid of the invention; and (b) identifying at least one preferred codon in the nucleic acid of step (a) and replacing it with a non-preferred or less preferred codon encoding the same amino acid as the replaced codon, wherein a preferred codon is a codon over-represented in coding sequences in genes in a host cell and a non-preferred or less preferred codon is a codon under-represented in coding sequences in genes in the host cell, thereby modifying the nucleic acid to decrease its expression in a host cell. In one aspect, the host cell can be a bacterial cell, a fungal cell, an insect cell, a yeast cell, a plant cell or a mammalian cell.

The invention provides methods for producing a library of nucleic acids encoding a plurality of modified polypeptide active sites (catalytic domains (CDs)) or substrate binding sites of polypeptides having enzymatic activity involved in chlorophyll catabolism or having an esterase (e.g., chlorophyllase) activity, wherein the modified active sites or substrate binding sites are derived from a first nucleic acid comprising a sequence encoding a first active site or a first substrate binding site the method comprising the following steps: (a) providing a first nucleic acid encoding a first active site or first substrate binding site, wherein the first nucleic acid sequence comprises a sequence that hybridizes under stringent conditions to a nucleic acid of the invention, and the nucleic acid encodes an active site or a substrate binding site; (b) providing a set of mutagenic oligonucleotides that encode naturally-occurring amino acid variants at a plurality of targeted codons in the first nucleic acid; and, (c) using the set of mutagenic oligonucleotides to generate a set of active site-encoding or substrate binding site-encoding variant nucleic acids encoding a range of amino acid variations at each amino acid codon that was mutagenized, thereby producing a library of nucleic acids encoding a plurality of modified active sites or substrate binding sites of polypeptides having enzymatic activity involved in chlorophyll catabolism or having an esterase (e.g., chlorophyllase) activity. In one aspect, the method comprises mutagenizing the first nucleic acid of step (a) by a method comprising an optimized directed evolution system, Gene Site-Saturation Mutagenesis (GSSM), synthetic ligation reassembly (SLR), error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, synthetic ligation reassembly (SLR) and a combination thereof. In another aspect, the method comprises mutagenizing the first nucleic acid of step (a) or variants by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

The invention provides methods for making a small molecule comprising the following steps: (a) providing a plurality of biosynthetic enzymes capable of synthesizing or modifying a small molecule, wherein one of the enzymes comprises a polypeptide of the invention or is encoded by a nucleic acid of the invention; (b) providing a substrate for at least one of the enzymes of step (a); and (c) reacting the substrate of step (b) with the enzymes under conditions that facilitate a plurality of biocatalytic reactions to generate a small molecule by a series of biocatalytic reactions. The invention provides methods for modifying a small molecule comprising the following steps: (a) providing an enzyme, wherein the enzyme comprises a polypeptide of the invention, or, a polypeptide encoded by a nucleic acid of the invention, or a subsequence thereof; (b) providing a small molecule; and (c) reacting the enzyme of step (a) with the small molecule of step (b) under conditions that facilitate an enzymatic reaction catalyzed by the polypeptide of the invention, or, a polypeptide encoded by a nucleic acid of the invention, thereby modifying a small molecule. In one aspect, the method can comprise a plurality of small molecule substrates for the enzyme of step (a), thereby generating a library of modified small molecules produced by at least one enzymatic reaction catalyzed by an enzyme of the invention. In one aspect, the method can comprise a plurality of additional enzymes under conditions that facilitate a plurality of biocatalytic reactions by the enzymes to form a library of modified small molecules produced by the plurality of enzymatic reactions. In another aspect, the method can further comprise the step of testing the library to determine if a particular modified small molecule that exhibits a desired activity is present within the library. The step of testing the library can further comprise the steps of systematically eliminating all but one of the biocatalytic reactions used to produce a portion of the plurality of the modified small molecules within the library by testing the portion of the modified small molecule for the presence or absence of the particular modified small molecule with a desired activity, and identifying at least one specific biocatalytic reaction that produces the particular modified small molecule of desired activity.

The invention provides methods for determining a functional fragment of a polypeptide of the invention, or, a polypeptide encoded by a nucleic acid of the invention, comprising the steps of: (a) providing a polypeptide of the invention, or a polypeptide encoded by a nucleic acid of the invention, or a subsequence thereof; and (b) deleting a plurality of amino acid residues from the sequence of step (a) and testing the remaining subsequence for enzyme or binding activity, thereby determining a functional fragment of the enzyme. In one aspect, activity is measured by providing a substrate and detecting a decrease in the amount of the substrate or an increase in the amount of a reaction product.

The invention provides methods for whole cell engineering of new or modified phenotypes by using real-time metabolic flux analysis, the method comprising the following steps: (a) making a modified cell by modifying the genetic composition of a cell, wherein the genetic composition is modified by addition to the cell of a nucleic acid of the invention; (b) culturing the modified cell to generate a plurality of modified cells; (c) measuring at least one metabolic parameter of the cell by monitoring the cell culture of step (b) in real time; and, (d) analyzing the data of step (c) to determine if the measured parameter differs from a comparable measurement in an unmodified cell under similar conditions, thereby identifying an engineered phenotype in the cell using real-time metabolic flux analysis. In one aspect, the genetic composition of the cell can be modified by a method comprising deletion of a sequence or modification of a sequence in the cell, or, knocking out the expression of a gene. In one aspect, the method can further comprise selecting a cell comprising a newly engineered phenotype. In another aspect, the method can comprise culturing the selected cell, thereby generating a new cell strain comprising a newly engineered phenotype.

The invention provides methods of increasing thermotolerance or thermostability of a polypeptide of the invention, or, a polypeptide encoded by a nucleic acid of the invention, the method comprising glycosylating a polypeptide comprising at least thirty contiguous amino acids of a polypeptide of the invention; or a polypeptide encoded by a nucleic acid sequence of the invention, thereby increasing the thermotolerance or thermostability of the polypeptide. In one aspect, the specific activity can be thermostable or thermotolerant at a temperature in the range from greater than about 37° C. to about 95° C.

The invention provides methods for overexpressing a recombinant polypeptide in a cell comprising expressing a vector comprising a nucleic acid comprising a nucleic acid of the invention or a nucleic acid sequence of the invention, wherein the sequence identities are determined by analysis with a sequence comparison algorithm or by visual inspection, wherein overexpression is effected by use of a high activity promoter, a dicistronic vector or by gene amplification of the vector.

The invention provides methods of making a transgenic plant comprising the following steps: (a) introducing a heterologous nucleic acid sequence into the cell, wherein the heterologous nucleic sequence comprises a nucleic acid sequence of the invention, thereby producing a transformed plant cell; and (b) producing a transgenic plant from the transformed cell. In one aspect, the step (a) can further comprise introducing the heterologous nucleic acid sequence by electroporation or microinjection of plant cell protoplasts. In another aspect, the step (a) can further comprise introducing the heterologous nucleic acid sequence directly to plant tissue by DNA particle bombardment. Alternatively, the step (a) can further comprise introducing the heterologous nucleic acid sequence into the plant cell DNA using an *Agrobacterium tumefaciens* host. In one aspect, the plant cell can be a potato, corn, rice, wheat, tobacco, or barley cell.

The invention provides methods of expressing a heterologous nucleic acid sequence in a plant cell comprising the following steps: (a) transforming the plant cell with a heterologous nucleic acid sequence operably linked to a promoter, wherein the heterologous nucleic sequence comprises a nucleic acid of the invention; (b) growing the plant under conditions wherein the heterologous nucleic acids sequence is expressed in the plant cell. The invention provides methods of expressing a heterologous nucleic acid sequence in a plant cell comprising the following steps: (a) transforming the plant cell with a heterologous nucleic acid sequence operably linked to a promoter, wherein the heterologous nucleic sequence comprises a sequence of the invention; (b) growing the plant under conditions wherein the heterologous nucleic acids sequence is expressed in the plant cell. In another aspect, an enzyme of the invention can be prepared by expression of a polynucleotide of the invention in an organism such as a bacterium, a yeast, a plant, an insect, a fungus or an animal. Exemplary organisms for expressing polypeptides of the invention can be *S. pombe, S. cerevisiae, Pichia* sp., e.g., *P. pastoris, E. coli, Streptomyces* sp., *Bacillus* sp. and *Lactobacillus* sp.

Another aspect of the invention is a method of making a polypeptide of the invention. The method includes introducing a nucleic acid encoding the polypeptide into a host cell, wherein the nucleic acid is operably linked to a promoter and culturing the host cell under conditions that allow expression of the nucleic acid. Another aspect of the invention is a method of making a polypeptide or peptide of the invention. The method includes introducing a nucleic acid encoding the polypeptide into a host cell, wherein the nucleic acid is operably linked to a promoter and culturing the host cell under conditions that allow expression of the nucleic acid, thereby producing the polypeptide.

Another aspect of the invention is a method of generating a variant including obtaining a nucleic acid having a sequence of the invention, sequences substantially identical thereto, sequences complementary to a sequence of the invention, and fragments thereof, and changing one or more nucleotides in the sequence to another nucleotide, deleting one or more nucleotides in the sequence, or adding one or more nucleotides to the sequence.

The invention provides biosynthetic systems for the catabolism of chlorophyll comprising at least one enzyme of the invention. The invention provides biosynthetic systems for the catabolism of chlorophyll comprising at least one nucleic acid encoding an enzyme involved in the catabolism of chlorophyll, wherein the nucleic acid comprises a sequence of the invention. In one aspect, the system comprises a plurality of enzyme-encoding nucleic acids, wherein the enzymes are involved in the catabolism of chlorophyll. In one aspect, the plurality of enzyme-encoding nucleic acids comprises all of the enzymes in a chlorophyll catabolism pathway. In one aspect, the plurality of enzyme-encoding nucleic acids are contained in at least one plasmid, expression cassette or expression vector.

In one aspect, the biosynthetic system of the invention is contained in (comprises) a cell. The cell can be a bacterial cell, a mammalian cell, a fungal cell, a yeast cell, an insect cell or a plant cell. The yeast cell can be a *Pichia* sp. or a *Saccharomyces* sp., such as a *Pichia pastoris, Saccharomyces cerevisiae* or *Schizosaccharomyces pombe*.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein, including Appendix A, are hereby expressly incorporated by reference for all purposes.

DESCRIPTION OF DRAWINGS

Like reference symbols in the various drawings indicate like elements.

DETAILED DESCRIPTION

Figure 1:
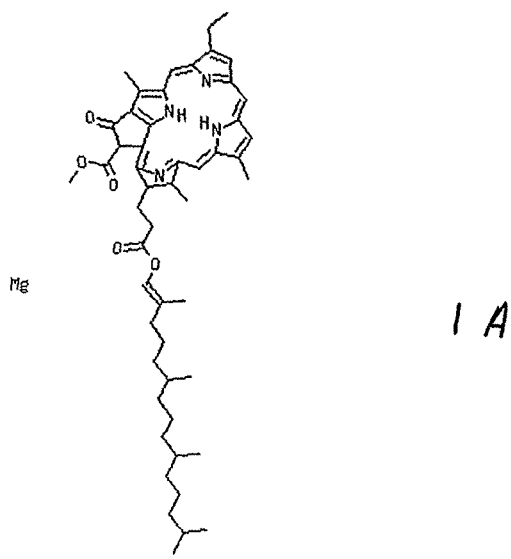
FIG. 1 is a schematic representation of chlorophyll (FIG. 1A), phytol (FIG. 1B) and chlorophyllide (FIG. 1C).
Figure 1:
Figure 1:
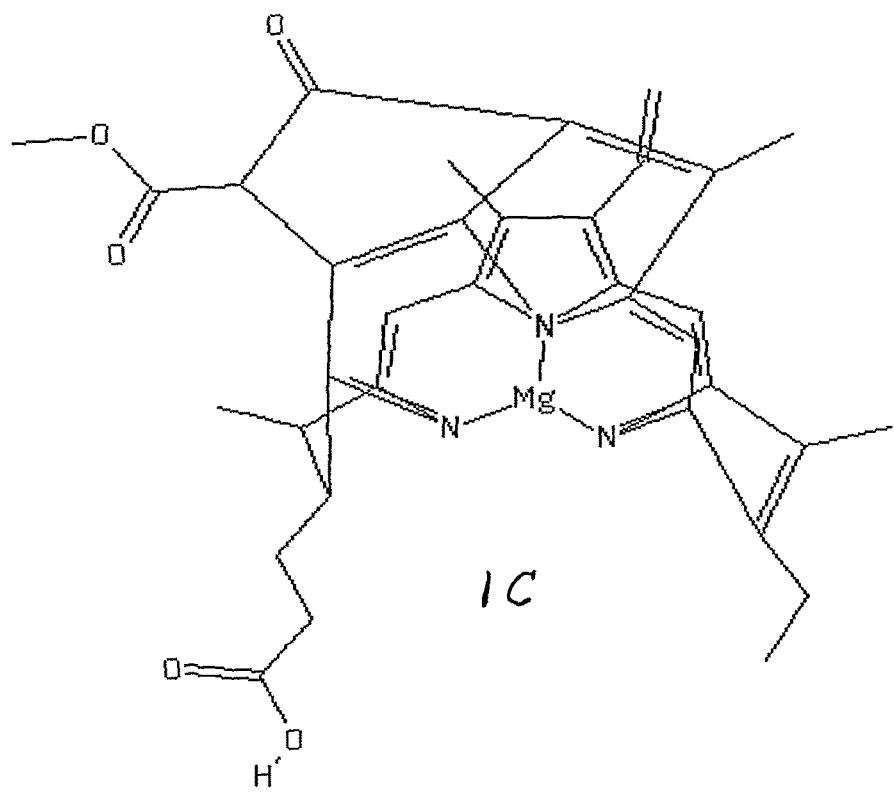

The present invention provides novel compositions and processes for the enzymatic treatment ("bleaching" or "decolorizing") of chlorophyll-containing or chlorophyll-contaminated compositions, e.g., plant, animal or algal preparations, foods, feeds or oils. In one aspect, the treatment (or, "enzymatic bleaching" or "de-colorizing") of chlorophyll used in the compositions and methods of the invention comprises use of a chlorophyllase enzyme, or other enzyme involved in chlorophyll catabolism, to modify chlorophyll, e.g., to facilitate removal of the color-bearing porphyrin ring by, e.g., aqueous extraction. Chlorophyllase catalyzes the hydrolysis of chlorophyll to generate chlorophyllide, which can be aqueous extracted, and phytol, which remains in the oil phase.

For example, in one aspect, the invention provides compositions and processes for the enzymatic processing (e.g., hydrolysis) of chlorophyll in a feed, food or oil, e.g., a vegetable oils, including oils processed from oilseeds, such as canola (rapeseed) oil or soybean oil, or oil fruits, such as palm oil. In one aspect, the invention provides enzymatic bleaching methods using a chlorophyllase enzyme for the enzymatic hydrolysis of a chlorophyll or any color-bearing porphyrin ring in an animal or a plant oil, e.g., vegetable oils.

The invention includes methods for enzymatically treating (e.g., "bleaching") chlorophyll-containing foods or oils via in vitro or in vivo techniques, e.g., whole cells protocols, such as fermentation or other biocatalytic processes.

Generating and Manipulating Nucleic Acids

The invention provides isolated, recombinant and synthetic nucleic acids (e.g., an exemplary nucleic acid of the invention, including SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19), and sequences having a sequence identity to an exemplary nucleic acid; nucleic acids encoding polypeptides of the invention, e.g., the exemplary amino acid sequences as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20). The invention also provides expression cassettes such as expression vectors, comprising nucleic acids of the invention, which include polynucleotides which encode the polypeptides of the invention. The invention also includes methods for discovering new polypeptide sequences using the nucleic acids of the invention. The invention also includes methods for inhibiting the expression of genes, transcripts and polypeptides using the nucleic acids of the invention. Also provided are methods for modifying the nucleic acids of the invention by, e.g., synthetic ligation reassembly, optimized directed evolution system and/or saturation mutagenesis.

The nucleic acids of the invention can be made, isolated and/or manipulated by, e.g., cloning and expression of cDNA libraries, amplification of message or genomic DNA by PCR, and the like.

In practicing the methods of the invention, homologous genes can be modified by manipulating a template nucleic acid, as described herein. The invention can be practiced in conjunction with any method or protocol or device known in the art, which are well described in the scientific and patent literature.

One aspect of the invention is an isolated nucleic acid comprising one of the sequences of the invention, or a fragment comprising at least 10, 15, 20, 25, 30, 35, 40, 50, 75, 100, 150, 200, 300, 400, or 500 consecutive bases of a nucleic acid of the invention. The isolated, nucleic acids may comprise DNA, including cDNA, genomic DNA and synthetic DNA. The DNA may be double-stranded or single-stranded and if single stranded may be the coding strand or non-coding (anti-sense) strand. Alternatively, the isolated nucleic acids may comprise RNA.

The isolated nucleic acids of the invention may be used to prepare one of the polypeptides of the invention, or fragments comprising at least 5, 10, 15, 20, 25, 30, 35, 40, 50, 75, 100, or 150 consecutive amino acids of one of the polypeptides of the invention.

Accordingly, another aspect of the invention is an isolated nucleic acid which encodes one of the polypeptides of the invention, or fragments comprising at least 5, 10, 15, 20, 25, 30, 35, 40, 50, 75, 100, or 150 consecutive amino acids of one of the polypeptides of the invention. The coding sequences of these nucleic acids may be identical to one of the coding sequences of one of the nucleic acids of the invention or may be different coding sequences which encode one of the of the invention having at least 5, 10, 15, 20, 25, 30, 35, 40, 50, 75, 100, or 150 consecutive amino acids of one of the polypeptides of the invention, as a result of the redundancy or degeneracy of the genetic code. The genetic code is well known to those of skill in the art and can be obtained, for example, on page 214 of B. Lewin, *Genes VI*, Oxford University Press, 1997.

The isolated nucleic acid which encodes one of the polypeptides of the invention, but is not limited to: only the coding sequence of a nucleic acid of the invention and additional coding sequences, such as leader sequences or proprotein sequences and non-coding sequences, such as introns or non-coding sequences 5' and/or 3' of the coding sequence. Thus, as used herein, the term "polynucleotide encoding a polypeptide" encompasses a polynucleotide which includes only the coding sequence for the polypeptide as well as a polynucleotide which includes additional coding and/or non-coding sequence.

Alternatively, the nucleic acid sequences of the invention, may be mutagenized using conventional techniques, such as site directed mutagenesis, or other techniques familiar to those skilled in the art, to introduce silent changes into the polynucleotides o of the invention. As used herein, "silent changes" include, for example, changes which do not alter the amino acid sequence encoded by the polynucleotide. Such changes may be desirable in order to increase the level of the polypeptide produced by host cells containing a vector encoding the polypeptide by introducing codons or codon pairs which occur frequently in the host organism.

The invention also relates to polynucleotides which have nucleotide changes which result in amino acid substitutions, additions, deletions, fusions and truncations in the polypeptides of the invention. Such nucleotide changes may be introduced using techniques such as site directed mutagenesis, random chemical mutagenesis, exonuclease III deletion and other recombinant DNA techniques. Alternatively, such nucleotide changes may be naturally occurring allelic variants which are isolated by identifying nucleic acids which specifically hybridize to probes comprising at least 10, 15, 20, 25, 30, 35, 40, 50, 75, 100, 150, 200, 300, 400, or 500 consecutive bases of one of the sequences of the invention (or the sequences complementary thereto) under conditions of high, moderate, or low stringency as provided herein.

As used herein, the term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition and still be isolated in that such vector or composition is not part of its natural environment. As used herein, the term "purified" does not require absolute purity; rather, it is intended as a relative definition. Individual nucleic acids obtained from a library have been conventionally purified to electrophoretic homogeneity. The sequences obtained from these clones could not be obtained directly either from the library or from total human DNA. The purified nucleic acids of the invention have been purified from the remainder of the genomic DNA in the organism by at least $10^4$-$10^6$ fold. However, the term "purified" also includes nucleic acids which have been purified from the remainder of the genomic DNA or from other sequences in a library or other environment by at least one order of magnitude, typically two or three orders and more typically four or five orders of magnitude.

As used herein, the term "recombinant" means that the nucleic acid is adjacent to a "backbone" nucleic acid to which it is not adjacent in its natural environment. Additionally, to be "enriched" the nucleic acids will represent 5% or more of the number of nucleic acid inserts in a population of nucleic acid backbone molecules. Backbone molecules according to the invention include nucleic acids such as expression vectors, self-replicating nucleic acids, viruses, integrating nucleic acids and other vectors or nucleic acids used to maintain or manipulate a nucleic acid insert of interest. Typically, the enriched nucleic acids represent 15% or more of the number of nucleic acid inserts in the population of recombinant backbone molecules. More typically, the enriched nucleic acids represent 50% or more of the number of nucleic acid inserts in the population of recombinant backbone molecules. In a one aspect, the enriched nucleic acids represent 90% or more of the number of nucleic acid inserts in the population of recombinant backbone molecules.

"Recombinant" polypeptides or proteins refer to polypeptides or proteins produced by recombinant DNA techniques; i.e., produced from cells transformed by an exogenous DNA construct encoding the desired polypeptide or protein. "Synthetic" polypeptides or protein are those prepared by chemical synthesis. Solid-phase chemical peptide synthesis methods can also be used to synthesize the polypeptide or fragments of the invention. Such method have been known in the art since the early 1960's (Merrifield, R. B., *J. Am. Chem. Soc.*, 85:2149-2154, 1963) (See also Stewart, J. M. and Young, J. D., *Solid Phase Peptide Synthesis, 2nd Ed.*, Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, *Proc. Natl. Acad. Sci., USA*, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

A promoter sequence is "operably linked to" a coding sequence when RNA polymerase which initiates transcription at the promoter will transcribe the coding sequence into mRNA.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described herein are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion, gel electrophoresis may be performed to isolate the desired fragment.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature and are well known in the art. In particular, stringency can be increased by reducing the concentration of salt, increasing the concentration of formamide, or raising the hybridization temperature. In alternative aspects, nucleic acids of the invention are defined by their ability to hybridize under various stringency conditions (e.g., high, medium, and low), as set forth herein.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS and 200 n/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "variant" refers to polynucleotides or polypeptides of the invention modified at one or more base pairs, codons, introns, exons, or amino acid residues (respectively) yet still retain the biological activity of an enzyme of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM and any combination thereof.

The term "Saturation Mutagenesis" or "Gene Site Saturation Mutagenesis" or "GSSM" includes a method that uses degenerate oligonucleotide primers to introduce point mutations into a polynucleotide, as described in detail, below.

The term "optimized directed evolution system" or "optimized directed evolution" includes a method for reassembling fragments of related nucleic acid sequences, e.g., related genes, and explained in detail, below.

The term "synthetic ligation reassembly" or "SLR" includes a method of ligating oligonucleotide fragments in a non-stochastic fashion, and explained in detail, below.

The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense (complementary) strand, to peptide nucleic acid (PNA), or to any DNA-like or RNA-like material, natural or synthetic in origin. The phrases "nucleic acid" or "nucleic acid sequence" includes oligonucleotide, nucleotide, polynucleotide, or to a fragment of any of these, to DNA or RNA (e.g., mRNA, rRNA, tRNA, iRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., e.g., double stranded iRNAs, e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156. "Oligonucleotide" includes either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide can ligate to a fragment that has not been dephosphorylated.

A "coding sequence of" or a "nucleotide sequence encoding" a particular polypeptide or protein, is a nucleic acid sequence which is transcribed and translated into a polypeptide or protein when placed under the control of appropriate regulatory sequences.

The term "gene" means the segment of DNA involved in producing a polypeptide chain; it includes regions preceding and following the coding region (leader and trailer) as well as, where applicable, intervening sequences (introns) between individual coding segments (exons). "Operably linked" as used herein refers to a functional relationship between two or more nucleic acid (e.g., DNA) segments. In one aspect, it refers to the functional relationship of transcriptional regulatory sequence to a transcribed sequence. For example, a promoter is operably linked to a coding sequence, such as a nucleic acid of the invention, if it stimulates or modulates the transcription of the coding sequence in an appropriate host cell or other expression system. In one aspect, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" as used herein refers to a nucleotide sequence which is capable of affecting expression of a structural gene (i.e., a protein coding sequence, such as an enzyme of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers. Thus, expression cassettes also include plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

As used herein, the term "promoter" includes all sequences capable of driving transcription of a coding sequence in a cell, e.g., a plant cell. Thus, promoters used in the constructs of the invention include cis-acting transcriptional control elements and regulatory sequences that are involved in regulating or modulating the timing and/or rate of transcription of a gene.

For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription. "Constitutive" promoters are those that drive expression continuously under most environmental conditions and states of development or cell differentiation. "Inducible" or "regulatable" promoters direct expression of the nucleic acid of the invention under the influence of environmental conditions or developmental conditions. Examples of environmental conditions that may affect transcription by inducible promoters include anaerobic conditions, elevated temperature, drought, or the presence of light.

"Tissue-specific" promoters are transcriptional control elements that are only active in particular cells or tissues or organs, e.g., in plants or animals. Tissue-specific regulation may be achieved by certain intrinsic factors which ensure that genes encoding proteins specific to a given tissue are expressed. Such factors are known to exist in mammals and plants so as to allow for specific tissues to develop.

General Techniques

The present invention provides novel compositions and processes for enzymatically treating (e.g., "bleaching") chlorophyll-containing compositions such as plants, algae, foods or oils. The skilled artisan will recognize that compounds used in the methods of the invention (e.g., catalytic, starting or intermediate compounds) can be synthesized using a variety of procedures and methodologies, which are well described in the scientific and patent literature., e.g., Organic Syntheses Collective Volumes, Gilman et al. (Eds) John Wiley & Sons, Inc., NY; Venuti (1989) *Pharm Res.* 6:867-873. The invention can be practiced in conjunction with any method or protocol known in the art, which are well described in the scientific and patent literature.

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides (e.g., enzymes of the invention) generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

The present invention provides novel compositions and processes for enzymatically treating (e.g., "bleaching") chlorophyll-containing compositions such as plants, algae, foods or oils. The skilled artisan will recognize that compounds used in the methods of the invention (e.g., catalytic, starting or intermediate compounds) can be synthesized using a variety of procedures and methodologies, which are well described in the scientific and patent literature., e.g., Organic Syntheses Collective Volumes, Gilman et al. (Eds) John Wiley & Sons, Inc., NY; Venuti (1989) *Pharm Res.* 6:867-873. The invention can be practiced in conjunction with any method or protocol known in the art, which are well described in the scientific and patent literature.

In one aspect, a nucleic acid encoding a polypeptide of the invention is assembled in appropriate phase with a leader sequence capable of directing secretion of the translated polypeptide or fragment thereof.

The invention provides fusion proteins and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

Transcriptional and Translational Control Sequences

The invention provides nucleic acid (e.g., DNA) sequences of the invention operatively linked to expression (e.g., transcriptional or translational) control sequence(s), e.g., promoters or enhancers, to direct or modulate RNA synthesis/expression. The expression control sequence can be in an expression vector. Exemplary bacterial promoters include lacI, lacZ, T3, T7, gpt, lambda PR, PL and trp. Exemplary eukaryotic promoters include CMV immediate early, HSV thymidine kinase, early and late SV40, LTRs from retrovirus, and mouse metallothionein I.

Promoters suitable for expressing a polypeptide in bacteria include the *E. coli* lac or trp promoters, the lad promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used. Promoters suitable for expressing the polypeptide or fragment thereof in bacteria include the *E. coli* lac or trp promoters, the lacI promoter, the lacZ promoter, the T3 promoter, the T7 promoter, the gpt promoter, the lambda $P_R$ promoter, the lambda $P_L$ promoter, promoters from operons encoding glycolytic enzymes such as 3-phosphoglycerate kinase (PGK) and the acid phosphatase promoter. Fungal promoters include the ∀ factor promoter. Eukaryotic promoters include the CMV immediate early promoter, the HSV thymidine kinase promoter, heat shock promoters, the early and late SV40 promoter, LTRs from retroviruses and the mouse metallothionein-I promoter. Other promoters known to control expression of genes in prokaryotic or eukaryotic cells or their viruses may also be used.

Tissue-Specific Plant Promoters

The invention provides expression cassettes that can be expressed in a tissue-specific manner, e.g., that can express an enzyme of the invention in a tissue-specific manner. The invention also provides plants or seeds that express an enzyme of the invention in a tissue-specific manner. The tissue-specificity can be seed specific, stem specific, leaf specific, root specific, fruit specific and the like.

In one aspect, a constitutive promoter such as the CaMV 35S promoter can be used for expression in specific parts of the plant or seed or throughout the plant. For example, for overexpression, a plant promoter fragment can be employed which will direct expression of a nucleic acid in some or all tissues of a plant, e.g., a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Such genes include, e.g., ACT11 from *Arabidopsis* (Huang (1996) *Plant Mol. Biol.* 33:125-139); Cat3 from *Arabidopsis* (GenBank No. U43147, Zhong (1996) *Mol. Gen. Genet.* 251:196-203); the gene encoding stearoyl-acyl carrier protein desaturase from *Brassica napus* (Genbank No. X74782, Solocombe (1994) *Plant Physiol.* 104: 1167-1176); GPc1 from maize (GenBank No. X15596; Martinez (1989) *J. Mol. Biol* 208:551-565); the Gpc2 from maize (GenBank No. U45855, Manjunath (1997) *Plant Mol. Biol.* 33:97-112); plant promoters described in U.S. Pat. Nos. 4,962,028; 5,633,440.

The invention uses tissue-specific or constitutive promoters derived from viruses which can include, e.g., the tobamovirus subgenomic promoter (Kumagai (1995) Proc. Natl. Acad. Sci. USA 92:1679-1683; the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) Plant Mol. Biol. 31:1129-1139).

Alternatively, the plant promoter may direct expression of enzyme-expressing nucleic acid in a specific tissue, organ or cell type (i.e. tissue-specific promoters) or may be otherwise under more precise environmental or developmental control or under the control of an inducible promoter. Examples of environmental conditions that may affect transcription include anaerobic conditions, elevated temperature, the presence of light, or sprayed with chemicals/hormones. For example, the invention incorporates the drought-inducible promoter of maize (Busk (1997) supra); the cold, drought, and high salt inducible promoter from potato (Kirch (1997) Plant Mol. Biol. 33:897 909).

Tissue-specific promoters can promote transcription only within a certain time frame of developmental stage within that tissue. See, e.g., Blazquez (1998) Plant Cell 10:791-800, characterizing the *Arabidopsis* LEAFY gene promoter. See also Cardon (1997) *Plant J* 12:367-77, describing the transcription factor SPL3, which recognizes a conserved sequence motif in the promoter region of the *A. thaliana* floral meristem identity gene AP1; and Mandel (1995) Plant Molecular Biology, Vol. 29, pp 995-1004, describing the meristem promoter eIF4. Tissue specific promoters which are active throughout the life cycle of a particular tissue can be used. In one aspect, the nucleic acids of the invention are operably linked to a promoter active primarily only in cotton fiber cells. In one aspect, the nucleic acids of the invention are operably linked to a promoter active primarily during the stages of cotton fiber cell elongation, e.g., as described by Rinehart (1996) supra. The nucleic acids can be operably linked to the Fb12A gene promoter to be preferentially expressed in cotton fiber cells (Ibid). See also, John (1997) Proc. Natl. Acad. Sci. USA 89:5769-5773; John, et al., U.S. Pat. Nos. 5,608,148 and 5,602,321, describing cotton fiber-specific promoters and methods for the construction of transgenic cotton plants. Root-specific promoters may also be used to express the nucleic acids of the invention. Examples of root-specific promoters include the promoter from the alcohol dehydrogenase gene (DeLisle (1990) Int. Rev. Cytol. 123:39-60). Other promoters that can be used to express the nucleic acids of the invention include, e.g., ovule-specific, embryo-specific, endosperm-specific, integument-specific, seed coat-specific promoters, or some combination thereof; a leaf-specific promoter (see, e.g., Busk (1997) Plant J. 11:1285 1295, describing a leaf-specific promoter in maize); the ORF13 promoter from *Agrobacterium rhizogenes* (which exhibits high activity in roots, see, e.g., Hansen (1997) supra); a maize pollen specific promoter (see, e.g., Guerrero (1990) Mol. Gen. Genet. 224:161 168); a tomato promoter active during fruit ripening, senescence and abscission of leaves and, to a lesser extent, of flowers can be used (see, e.g., Blume (1997) Plant J. 12:731 746); a pistil-specific promoter from the potato SK2 gene (see, e.g., Ficker (1997) Plant Mol. Biol. 35:425 431); the Blec4 gene from pea, which is active in epidermal tissue of vegetative and floral shoot apices of transgenic alfalfa making it a useful tool to target the expression of foreign genes to the epidermal layer of actively growing shoots or fibers; the ovule-specific BEL1 gene (see, e.g., Reiser (1995) Cell 83:735-742, GenBank No. U39944); and/or, the promoter in Klee, U.S. Pat. No. 5,589,583, describing a plant promoter region is capable of conferring high levels of transcription in meristematic tissue and/or rapidly dividing cells.

Alternatively, plant promoters which are inducible upon exposure to plant hormones, such as auxins, are used to express the nucleic acids of the invention. For example, the invention can use the auxin-response elements E1 promoter fragment (AuxREs) in the soybean (*Glycine max* L.) (Liu (1997) Plant Physiol. 115:397-407); the auxin-responsive *Arabidopsis* GST6 promoter (also responsive to salicylic acid and hydrogen peroxide) (Chen (1996) Plant J. 10: 955-966); the auxin-inducible parC promoter from tobacco (Sakai (1996) 37:906-913); a plant biotin response element (Streit (1997) Mol. Plant Microbe Interact. 10:933-937); and, the promoter responsive to the stress hormone abscisic acid (Sheen (1996) Science 274:1900-1902).

The nucleic acids of the invention can also be operably linked to plant promoters which are inducible upon exposure to chemicals reagents which can be applied to the plant, such as herbicides or antibiotics. For example, the maize In2-2 promoter, activated by benzenesulfonamide herbicide safeners, can be used (De Veylder (1997) Plant Cell Physiol. 38:568-577); application of different herbicide safeners induces distinct gene expression patterns, including expression in the root, hydathodes, and the shoot apical meristem. Coding sequence can be under the control of, e.g., a tetracycline-inducible promoter, e.g., as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324). Using chemically- (e.g., hormone- or pesticide-) induced promoters, i.e., promoter responsive to a chemical which can be applied to the transgenic plant in the field, expression of a polypeptide of the invention can be induced at a particular stage of development of the plant. Thus, the invention also provides for transgenic plants containing an inducible gene encoding for polypeptides of the invention whose host range is limited to target plant species, such as corn, rice, barley, wheat, potato or other crops, inducible at any stage of development of the crop.

One of skill will recognize that a tissue-specific plant promoter may drive expression of operably linked sequences in tissues other than the target tissue. Thus, a tissue-specific promoter is one that drives expression preferentially in the target tissue or cell type, but may also lead to some expression in other tissues as well.

The nucleic acids of the invention can also be operably linked to plant promoters which are inducible upon exposure to chemicals reagents. These reagents include, e.g., herbicides, synthetic auxins, or antibiotics which can be applied, e.g., sprayed, onto transgenic plants. Inducible expression of the enzyme-producing nucleic acids of the invention will allow the grower to select plants with the optimal enzyme expression and/or activity. The development of plant parts can thus controlled. In this way the invention provides the means to facilitate the harvesting of plants and plant parts. For example, in various embodiments, the maize In2-2 promoter, activated by benzenesulfonamide herbicide safeners, is used (De Veylder (1997) Plant Cell Physiol. 38:568-577); application of different herbicide safeners induces distinct gene expression patterns, including expression in the root, hydathodes, and the shoot apical meristem. Coding sequences of the invention are also under the control of a tetracycline-inducible promoter, e.g., as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324).

In some aspects, proper polypeptide expression may require polyadenylation region at the 3'-end of the coding region. The polyadenylation region can be derived from the natural gene, from a variety of other plant (or animal or other) genes, or from genes in the Agrobacterial T-DNA.

The term "plant" includes whole plants, plant parts (e.g., leaves, stems, flowers, roots, etc.), plant protoplasts, seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous states. As used herein, the term "transgenic plant" includes plants or plant cells into which a heterologous nucleic acid sequence has been inserted, e.g., the nucleic acids and various recombinant constructs (e.g., expression cassettes) of the invention.

Expression Vectors and Cloning Vehicles

The invention provides expression vectors and cloning vehicles comprising nucleic acids of the invention, e.g., sequences encoding the enzymes of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *Bacillus, Aspergillus* and yeast). Vectors of the invention can include chromosomal, non-chromosomal and synthetic DNA sequences. Large numbers of suitable vectors are known to those of skill in the art, and are commercially available. Exemplary vectors are include: bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

"Plasmids" can be commercially available, publicly available on an unrestricted basis, or can be constructed from available plasmids in accord with published procedures. Equivalent plasmids to those described herein are known in the art and will be apparent to the ordinarily skilled artisan.

The expression vector can comprise a promoter, a ribosome binding site for translation initiation and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

In one aspect, the expression vectors contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli*, and the *S. cerevisiae* TRP1 gene. Promoter regions can be selected from any desired gene using chloramphenicol transferase (CAT) vectors or other vectors with selectable markers.

Vectors for expressing the polypeptide or fragment thereof in eukaryotic cells can also contain enhancers to increase expression levels. Enhancers are cis-acting elements of DNA, usually from about 10 to about 300 bp in length that act on a promoter to increase its transcription. Examples include the SV40 enhancer on the late side of the replication origin by 100 to 270, the cytomegalovirus early promoter enhancer, the polyoma enhancer on the late side of the replication origin, and the adenovirus enhancers.

A nucleic acid sequence can be inserted into a vector by a variety of procedures. In general, the sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art.

The vector can be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook.

Particular bacterial vectors which can be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, DR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

The nucleic acids of the invention can be expressed in expression cassettes, vectors or viruses and transiently or stably expressed in plant cells and seeds. One exemplary transient expression system uses episomal expression systems, e.g., cauliflower mosaic virus (CaMV) viral RNA generated in the nucleus by transcription of an episomal minichromosome containing supercoiled DNA, see, e.g., Covey (1990) Proc. Natl. Acad. Sci. USA 87:1633-1637. Alternatively, coding sequences, i.e., all or sub-fragments of sequences of the invention can be inserted into a plant host cell genome becoming an integral part of the host chromosomal DNA. Sense or antisense transcripts can be expressed in this manner. A vector comprising the sequences (e.g., promoters or coding regions) from nucleic acids of the invention can comprise a marker gene that confers a selectable phenotype on a plant cell or a seed. For example, the marker may encode biocide resistance, particularly antibiotic resistance, such as resistance to kanamycin, G418, bleomycin, hygromycin, or herbicide resistance, such as resistance to chlorosulfuron or Basta.

Expression vectors capable of expressing nucleic acids and proteins in plants are well known in the art, and can include, e.g., vectors from *Agrobacterium* spp., potato virus X (see, e.g., Angell (1997) EMBO J. 16:3675-3684), tobacco mosaic virus (see, e.g., Casper (1996) Gene 173:69-73), tomato bushy stunt virus (see, e.g., Hillman (1989) Virology 169:42-50), tobacco etch virus (see, e.g., Dolja (1997) Virology 234: 243-252), bean golden mosaic virus (see, e.g., Morinaga (1993) Microbiol Immunol. 37:471-476), cauliflower mosaic virus (see, e.g., Cecchini (1997) Mol. Plant Microbe Interact. 10:1094-1101), maize Ac/Ds transposable element (see, e.g., Rubin (1997) Mol. Cell. Biol. 17:6294-6302; Kunze (1996) Curr. Top. Microbiol. Immunol. 204:161-194), and the maize suppressor-mutator (Spm) transposable element (see, e.g., Schlappi (1996) Plant Mol. Biol. 32:717-725); and derivatives thereof.

In one aspect, the expression vector can have two replication systems to allow it to be maintained in two organisms, for example in mammalian or insect cells for expression and in a prokaryotic host for cloning and amplification. Furthermore, for integrating expression vectors, the expression vector can contain at least one sequence homologous to the host cell genome. It can contain two homologous sequences which flank the expression construct. The integrating vector can be directed to a specific locus in the host cell by selecting the appropriate homologous sequence for inclusion in the vector. Constructs for integrating vectors are well known in the art.

Expression vectors of the invention may also include a selectable marker gene to allow for the selection of bacterial strains that have been transformed, e.g., genes which render the bacteria resistant to drugs such as ampicillin, chloramphenicol, erythromycin, kanamycin, neomycin and tetracycline. Selectable markers can also include biosynthetic genes, such as those in the histidine, tryptophan and leucine biosynthetic pathways.

The DNA sequence in the expression vector is operatively linked to an appropriate expression control sequence(s) (promoter) to direct RNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using chloramphenicol transferase (CAT) vectors or other vectors with selectable markers. In addition, the expression vectors in one aspect contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Mammalian expression vectors may also comprise an origin of replication, any necessary ribosome binding sites, a polyadenylation site, splice donor and acceptor sites, transcriptional termination sequences and 5' flanking nontranscribed sequences. In some aspects, DNA sequences derived from the SV40 splice and polyadenylation sites may be used to provide the required nontranscribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin by 100 to 270, the cytomegalovirus early promoter enhancer, the polyoma enhancer on the late side of the replication origin and the adenovirus enhancers.

In addition, the expression vectors typically contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli* and the *S. cerevisiae* TRP1 gene.

In some aspects, the nucleic acid encoding one of the polypeptides of the invention, or fragments comprising at least about 5, 10, 15, 20, 25, 30, 35, 40, 50, 75, 100, or 150 consecutive amino acids thereof is assembled in appropriate phase with a leader sequence capable of directing secretion of the translated polypeptide or fragment thereof. Optionally, the nucleic acid can encode a fusion polypeptide in which one of the polypeptides of the invention, or fragments comprising at least 5, 10, 15, 20, 25, 30, 35, 40, 50, 75, 100, or 150 consecutive amino acids thereof is fused to heterologous peptides or polypeptides, such as N-terminal identification peptides which impart desired characteristics, such as increased stability or simplified purification.

The appropriate DNA sequence may be inserted into the vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are disclosed in Ausubel et al. Current Protocols in Molecular Biology, John Wiley 503 Sons, Inc. 1997 and Sambrook et al., *Molecular Cloning: A Laboratory Manual 2nd Ed.*, Cold Spring Harbor Laboratory Press (1989. Such procedures and others are deemed to be within the scope of those skilled in the art.

The vector may be, for example, in the form of a plasmid, a viral particle, or a phage. Other vectors include chromosomal, nonchromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus and pseudorabies. A variety of cloning and expression vectors for use with prokaryotic and eukaryotic hosts are described by Sambrook, et al., *Molecular Cloning: A Laboratory Manual, 2nd Ed.*, Cold Spring Harbor, N.Y., (1989).

Host Cells and Transformed Cells

The invention also provides a transformed cell comprising a nucleic acid sequence of the invention, e.g., a sequence encoding an enzyme of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Lactococcus lactis, Streptomyces, Bacillus subtilis, Bacillus cereus, Salmonella typhimurium* or any species within the genera *Bacillus, Streptomyces* and *Staphylococcus*. Exemplary insect cells include *Drosophila* S2 and *Spodoptera* Sf9. Exemplary yeast cells include *Pichia pastoris, Saccharomyces cerevisiae* or *Schizosaccharomyces pombe*. Exemplary animal cells include CHO, COS or Bowes melanoma or any mouse or human cell line. The selection of an appropriate host is within the abilities of those skilled in the art. Techniques for transforming a wide variety of higher plant species are well known and described in the technical and scientific literature. See, e.g., Weising (1988) Ann. Rev. Genet. 22:421-477; U.S. Pat. No. 5,750,870.

The vector can be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

In one aspect, the nucleic acids or vectors of the invention are introduced into the cells for screening, thus, the nucleic acids enter the cells in a manner suitable for subsequent expression of the nucleic acid. The method of introduction is largely dictated by the targeted cell type. Exemplary methods include $CaPO_4$ precipitation, liposome fusion, lipofection (e.g., LIPOFECTIN™), electroporation, viral infection, etc. The candidate nucleic acids may stably integrate into the genome of the host cell (for example, with retroviral introduction) or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets can be used.

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in E. coli.

Host cells containing the polynucleotides of interest, e.g., nucleic acids of the invention, can be cultured in conventional nutrient media modified as appropriate for activating promoters, selecting transformants or amplifying genes. The culture conditions, such as temperature, pH and the like, are those previously used with the host cell selected for expression and will be apparent to the ordinarily skilled artisan. The clones which are identified as having the specified enzyme activity may then be sequenced to identify the polynucleotide sequence encoding an enzyme having the enhanced activity.

The invention provides a method for overexpressing a recombinant enzyme in a cell comprising expressing a vector comprising a nucleic acid of the invention, e.g., a nucleic acid comprising a nucleic acid sequence with at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to an exemplary sequence of the invention over a region of at least about 50, 75, 100, 150, 200, 250, 300, 350, 400, 450, 500, 550, 600, 650, 700, 750, 800, 850, 900, 950, 1000, 1050, 1100, 1150 or more residues, or the full length of a gene or a transcript, wherein the sequence identities are determined by analysis with a sequence comparison algorithm or by visual inspection, or, a nucleic acid that hybridizes under stringent conditions to a nucleic acid sequence of the invention. The overexpression can be effected by any means, e.g., use of a high activity promoter, a dicistronic vector or by gene amplification of the vector.

The nucleic acids of the invention can be expressed, or overexpressed, in any in vitro or in vivo expression system. Any cell culture systems can be employed to express, or over-express, recombinant protein, including bacterial, insect, yeast, fungal or mammalian cultures. Over-expression can be effected by appropriate choice of promoters, enhancers, vectors (e.g., use of replicon vectors, dicistronic vectors (see, e.g., Gurtu (1996) Biochem. Biophys. Res. Commun. 229:295-8), media, culture systems and the like. In one aspect, gene amplification using selection markers, e.g., glutamine synthetase (see, e.g., Sanders (1987) Dev. Biol. Stand. 66:55-63), in cell systems are used to overexpress the polypeptides of the invention.

The host cell may be any of the host cells familiar to those skilled in the art, including prokaryotic cells, eukaryotic cells, mammalian cells, insect cells, or plant cells. As representative examples of appropriate hosts, there may be mentioned: bacterial cells, such as E. coli, Streptomyces, Bacillus subtilis, Salmonella typhimurium and various species within the genera Streptomyces and Staphylococcus, fungal cells, such as yeast, insect cells such as Drosophila S2 and Spodoptera Sf9, animal cells such as CHO, COS or Bowes melanoma and adenoviruses. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells are typically harvested by centrifugation, disrupted by physical or chemical means and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described by Gluzman, Cell, 23:175, 1981) and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Alternatively, the polypeptides of the invention, or fragments comprising at least 5, 10, 15, 20, 25, 30, 35, 40, 50, 75, 100, or 150 or more consecutive amino acids thereof can be synthetically produced by conventional peptide synthesizers. In other aspects, fragments or portions of the polypeptides may be employed for producing the corresponding full-length polypeptide by peptide synthesis; therefore, the fragments may be employed as intermediates for producing the full-length polypeptides.

Cell-free translation systems can also be employed to produce one of the polypeptides of the invention, or fragments comprising at least 5, 10, 15, 20, 25, 30, 35, 40, 50, 75, 100, or 150 consecutive amino acids thereof using mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

Amplification of Nucleic Acids

In practicing the invention, nucleic acids of the invention and nucleic acids encoding enzymes of the invention, or modified nucleic acids of the invention, can be reproduced by amplification. Amplification can also be used to clone or modify the nucleic acids of the invention. Thus, the invention provides amplification primer sequence pairs for amplifying nucleic acids of the invention. One of skill in the art can design amplification primer sequence pairs for any part of or the full length of these sequences.

In one aspect, the invention provides a nucleic acid amplified by a primer pair of the invention, e.g., a primer pair as set forth by about the first (the 5') 12, 13, 14, 15, 16, 17, 18, 19, 20, 21, 22, 23, 24, or 25 residues of a nucleic acid of the invention, and about the first (the 5') 15, 16, 17, 18, 19, 20, 21, 22, 23, 24, or 25 residues of the complementary strand.

The invention provides an amplification primer sequence pair for amplifying a nucleic acid encoding a polypeptide having an enzyme activity, wherein the primer pair is capable of amplifying a nucleic acid comprising a sequence of the invention, or fragments or subsequences thereof. One or each member of the amplification primer sequence pair can comprise an oligonucleotide comprising at least about 10 to 50 consecutive bases of the sequence, or about 12, 13, 14, 15, 16, 17, 18, 19, 20, 21, 22, 23, 24, or 25 consecutive bases of the sequence. The invention provides amplification primer pairs, wherein the primer pair comprises a first member having a sequence as set forth by about the first (the 5') 12, 13, 14, 15, 16, 17, 18, 19, 20, 21, 22, 23, 24, or 25 residues of a nucleic acid of the invention, and a second member having a sequence as set forth by about the first (the 5') 12, 13, 14, 15, 16, 17, 18, 19, 20, 21, 22, 23, 24, or 25 residues of the complementary strand of the first member. The invention provides enzyme-encoding nucleic acids generated by amplification, e.g., polymerase chain reaction (PCR), using an amplification primer pair of the invention. The invention provides methods of making enzyme-encoding nucleic acids by amplification, e.g., polymerase chain reaction (PCR), using an amplification primer pair of the invention. In one aspect, the amplification primer pair amplifies a nucleic acid from a library, e.g., a gene library, such as an environmental library.

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect of the invention, message isolated from a cell or a cDNA library are amplified.

The skilled artisan can select and design suitable oligonucleotide amplification primers. Amplification methods are also well known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques (e.g., NASBA, Cangene, Mississauga, Ontario); see also Berger (1987) Methods Enzymol. 152:307-316; Sambrook; Ausubel; U.S. Pat. Nos. 4,683,195 and 4,683,202; Sooknanan (1995) Biotechnology 13:563-564.

Determining the Degree of Sequence Identity

The invention provides nucleic acids comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention (e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19) over a region of at least about 10, 20, 30, 40, 50, 60, 70, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more, residues. The invention provides polypeptides comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptide of the invention. The extent of sequence identity (homology) may be determined using any computer program and associated parameters, including those described herein, such as BLAST 2.2.2. or FASTA version 3.0t78, with the default parameters.

Nucleic acid sequences of the invention can comprise at least 10, 15, 20, 25, 30, 35, 40, 50, 75, 100, 150, 200, 300, 400, or 500 consecutive nucleotides of an exemplary sequence of the invention and sequences substantially identical thereto. Homologous sequences and fragments of nucleic acid sequences of the invention can refer to a sequence having at least 99%, 98%, 97%, 96%, 95%, 90%, 85%, 80%, 75%, 70%, 65%, 60%, 55%, or 50% homology to these sequences. Homology may be determined using any of the computer programs and parameters described herein, including FASTA version 3.0t78 with the default parameters. Homologous sequences also include RNA sequences in which uridines replace the thymines in the nucleic acid sequences of the invention. The homologous sequences may be obtained using any of the procedures described herein or may result from the correction of a sequencing error. It will be appreciated that the nucleic acid sequences of the invention can be represented in the traditional single character format (See the inside back cover of Stryer, Lubert. Biochemistry, 3rd Ed., W. H Freeman & Co., New York.) or in any other format which records the identity of the nucleotides in a sequence.

Various sequence comparison programs identified elsewhere in this patent specification are particularly contemplated for use in this aspect of the invention. Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA and CLUSTALW (Pearson and Lipman, Proc. Natl. Acad. Sci. USA 85(8):2444-2448, 1988; Altschul et al., J. Mol. Biol. 215(3):403-410, 1990; Thompson et al., Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993).

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol 48:443, 1970, by the search for similarity method of person & Lipman, Proc. Nat'l. Acad. Sci. USA 85:2444, 1988, by computerized implementations of these algorithms (GAP, BEST-FIT, FASTA and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (J. Roach, http://weber.u.Washington.edu/~roach/human_genome_progress 2.html) (Gibbs, 1995). At least twenty-one other genomes have already been sequenced, including, for example, M. genitalium (Fraser et al., 1995), M. jannaschii (Bult et al., 1996), H. influenzae (Fleischmann et al., 1995), E. coli (Blattner et al., 1997) and yeast (S. cerevisiae) (Mewes et al., 1997) and D. melanogaster (Adams et al., 2000). Significant progress has also been made in sequencing the genomes of model organism, such as mouse, C. elegans and Arabadopsis sp. Several databases containing genomic information annotated with some functional information are maintained by different organization and are accessible via the internet One example of a useful algorithm is BLAST and BLAST 2.0 algorithms, which are described in Altschul et al., Nuc. Acids Res. 25:3389-3402, 1977 and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3 and expectations (E) of 10 and the BLOSUM62 scoring matrix (see Henikoff & Henikoff, Proc. Natl. Acad. Sci. USA 89:10915, 1989) alignments (B) of 50, expectation (E) of 10, M=5, N=−4 and a comparison of both strands.

The BLAST algorithm also performs a statistical analysis of the similarity between two sequences (see, e.g., Karlin & Altschul, Proc. Natl. Acad. Sci. USA 90:5873, 1993). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more in one aspect less than about 0.01 and most in one aspect less than about 0.001.

In one aspect, protein and nucleic acid sequence homologies are evaluated using the Basic Local Alignment Search Tool ("BLAST") In particular, five specific BLAST programs are used to perform the following task:
 (1) BLASTP and BLAST3 compare an amino acid query sequence against a protein sequence database;
 (2) BLASTN compares a nucleotide query sequence against a nucleotide sequence database;
 (3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is in one aspect obtained from a protein or nucleic acid sequence database. High-scoring segment pairs are in one aspect identified (i.e., aligned) by means of a scoring matrix, many of which are known in the art. In one aspect, the scoring matrix used is the BLOSUM62 matrix (Gonnet et al., Science 256:1443-1445, 1992; Henikoff and Henikoff, Proteins 17:49-61, 1993). Less in one aspect, the PAM or PAM250 matrices may also be used (see, e.g., Schwartz and Dayhoff, eds., 1978, *Matrices for Detecting Distance Relationships: Atlas of Protein Sequence and Structure*, Washington: National Biomedical Research Foundation). BLAST programs are accessible through the U.S. National Library of Medicine.

The parameters used with the above algorithms may be adapted depending on the sequence length and degree of homology studied. In some aspects, the parameters may be the default parameters used by the algorithms in the absence of instructions from the user.

In one aspect, the phrase "substantially identical" in the context of two nucleic acids or polypeptides, refers to two or more sequences that have, e.g., at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more nucleotide or amino acid residue (sequence) identity, when compared and aligned for maximum correspondence, as measured using one of the known sequence comparison algorithms or by visual inspection. In alternative aspects, the substantial identity exists over a region of at least about 50, 75, 100, 150, 200, 250, 300, 350, 400, 450, 500, 550, 600, 650, 700, 750, 800, 850, 900, 950, 1000, 1050, 1100, 1150 or more residues, or the full length of a gene or a transcript. In some aspects, the sequences are substantially identical over the entire length of a coding region.

Computer Systems and Computer Program Products

To determine and identify sequence identities, structural homologies, motifs and the like in silico, a nucleic acid or polypeptide sequence of the invention can be stored, recorded, and manipulated on any medium which can be read and accessed by a computer.

Accordingly, the invention provides computers, computer systems, computer readable mediums, computer programs products and the like recorded or stored thereon the nucleic acid and polypeptide sequences of the invention. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention.

The polypeptides of the invention include the polypeptide sequences of the invention, e.g., the exemplary sequences of the invention, and sequences substantially identical thereto, and fragments of any of the preceding sequences. Substantially identical, or homologous, polypeptide sequences refer to a polypeptide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary sequence of the invention.

Homology may be determined using any of the computer programs and parameters described herein, including FASTA version 3.0t78 with the default parameters or with any modified parameters. The homologous sequences may be obtained using any of the procedures described herein or may result from the correction of a sequencing error. The polypeptide fragments comprise at least about 10, 15, 20, 25, 30, 35, 40, 45, 50, 75, 100, 150, 200, 250, 300, 350, 400, 450, 500 or more consecutive amino acids of the polypeptides of the invention. It will be appreciated that the polypeptide codes as set forth in amino acid sequences of the invention, can be represented in the traditional single character format or three letter format (See the inside back cover of Stryer, Lubert. *Biochemistry*, 3rd Ed., W. H Freeman & Co., New York.) or in any other format which relates the identity of the polypeptides in a sequence.

A nucleic acid or polypeptide sequence of the invention can be stored, recorded and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid sequences of the invention, one or more of the polypeptide sequences of the invention. Another aspect of the invention is a computer readable medium having recorded thereon at least 2, 5, 10, 15, or 20 or more nucleic acid sequences of the invention.

Another aspect of the invention is a computer readable medium having recorded thereon one or more of the nucleic acid sequences of the invention. Another aspect of the invention is a computer readable medium having recorded thereon one or more of the polypeptide sequences of the invention. Another aspect of the invention is a computer readable medium having recorded thereon at least 2, 5, 10, 15, or 20 or more of the sequences as set forth above.

As used herein, the terms "computer," "computer program" and "processor" are used in their broadest general contexts and incorporate all such devices, as described in detail, below. A "coding sequence of" or a "sequence encodes" a particular polypeptide or protein, is a nucleic acid sequence which is transcribed and translated into a polypeptide or protein when placed under the control of appropriate regulatory sequences.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Aspects of the invention include systems (e.g., internet based systems), particularly computer systems which store and manipulate the sequence information described herein. One example of a computer system 100 is illustrated in block diagram form in FIG. 7. As used herein, "a computer system" refers to the hardware components, software components and data storage components used to analyze a nucleotide sequence of a nucleic acid sequence of the invention, or a polypeptide sequence of the invention. The computer system 100 typically includes a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines.

Typically the computer system 100 is a general purpose system that comprises the processor 105 and one or more internal data storage components 110 for storing data and one or more data retrieving devices for retrieving the data stored on the data storage components. A skilled artisan can readily appreciate that any one of the currently available computer systems are suitable.

In one particular aspect, the computer system 100 includes a processor 105 connected to a bus which is connected to a main memory 115 (in one aspect implemented as RAM) and one or more internal data storage devices 110, such as a hard drive and/or other computer readable media having data recorded thereon. In some aspects, the computer system 100 further includes one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet) etc. In some aspects, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125*a-c* in a network or wide area network to provide centralized access to the computer system 100.

Software for accessing and processing the nucleotide sequences of a nucleic acid sequence of the invention, or a polypeptide sequence of the invention, (such as search tools, compare tools and modeling tools etc.) may reside in main memory 115 during execution.

In some aspects, the computer system 100 may further comprise a sequence comparison algorithm for comparing a nucleic acid sequence of the invention, or a polypeptide sequence of the invention, stored on a computer readable medium to a reference nucleotide or polypeptide sequence(s) stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of a nucleic acid sequence of the invention, or a polypeptide sequence of the invention, stored on a computer readable medium to reference sequences stored on a computer readable medium to identify homologies or structural motifs.

Figure 5:
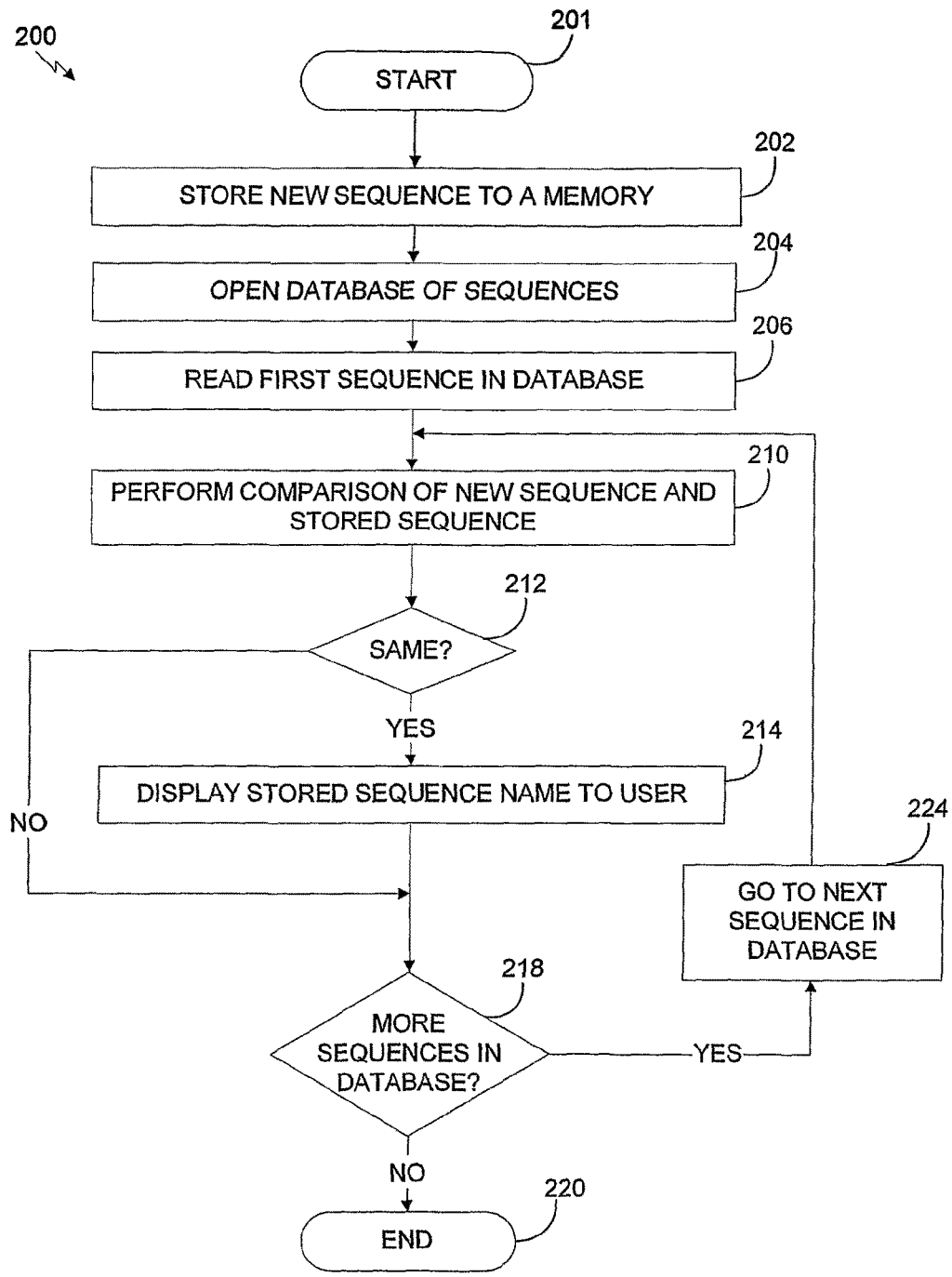
FIG. 5 is a flow diagram illustrating one aspect of a process of the invention for comparing a new nucleotide or protein sequence with a database of sequences in order to determine the homology levels between the new sequence and the sequences in the database, as described in detail, below.

FIG. 5 is a flow diagram illustrating one aspect of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the invention is a computer system comprising a processor, a data storage device having stored thereon a nucleic acid sequence of the invention, or a polypeptide sequence of the invention, a data storage device having retrievably stored thereon reference nucleotide sequences or polypeptide sequences to be compared to a nucleic acid sequence of the invention, or a polypeptide sequence of the invention and a sequence comparer for conducting the comparison. The sequence comparer may indicate a homology level between the sequences compared or identify structural motifs in the above described nucleic acid code a nucleic acid sequence of the invention, or a polypeptide sequence of the invention, or it may identify structural motifs in sequences which are compared to these nucleic acid codes and polypeptide codes. In some aspects, the data storage device may have stored thereon the sequences of at least 2, 5, 10, 15, 20, 25, 30 or 40 or more of the nucleic acid sequences of the invention, or the polypeptide sequences of the invention.

Another aspect of the invention is a method for determining the level of homology between a nucleic acid sequence of the invention, or a polypeptide sequence of the invention and a reference nucleotide sequence. The method including reading the nucleic acid code or the polypeptide code and the reference nucleotide or polypeptide sequence through the use of a computer program which determines homology levels and determining homology between the nucleic acid code or polypeptide code and the reference nucleotide or polypeptide sequence with the computer program. The computer program may be any of a number of computer programs for determining homology levels, including those specifically enumerated herein, (e.g., BLAST2N with the default parameters or with any modified parameters). The method may be implemented using the computer systems described above. The method may also be performed by reading at least 2, 5, 10, 15, 20, 25, 30 or 40 or more of the above described nucleic acid sequences of the invention, or the polypeptide sequences of the invention through use of the computer program and determining homology between the nucleic acid codes or polypeptide codes and reference nucleotide sequences or polypeptide sequences.

Figure 6:
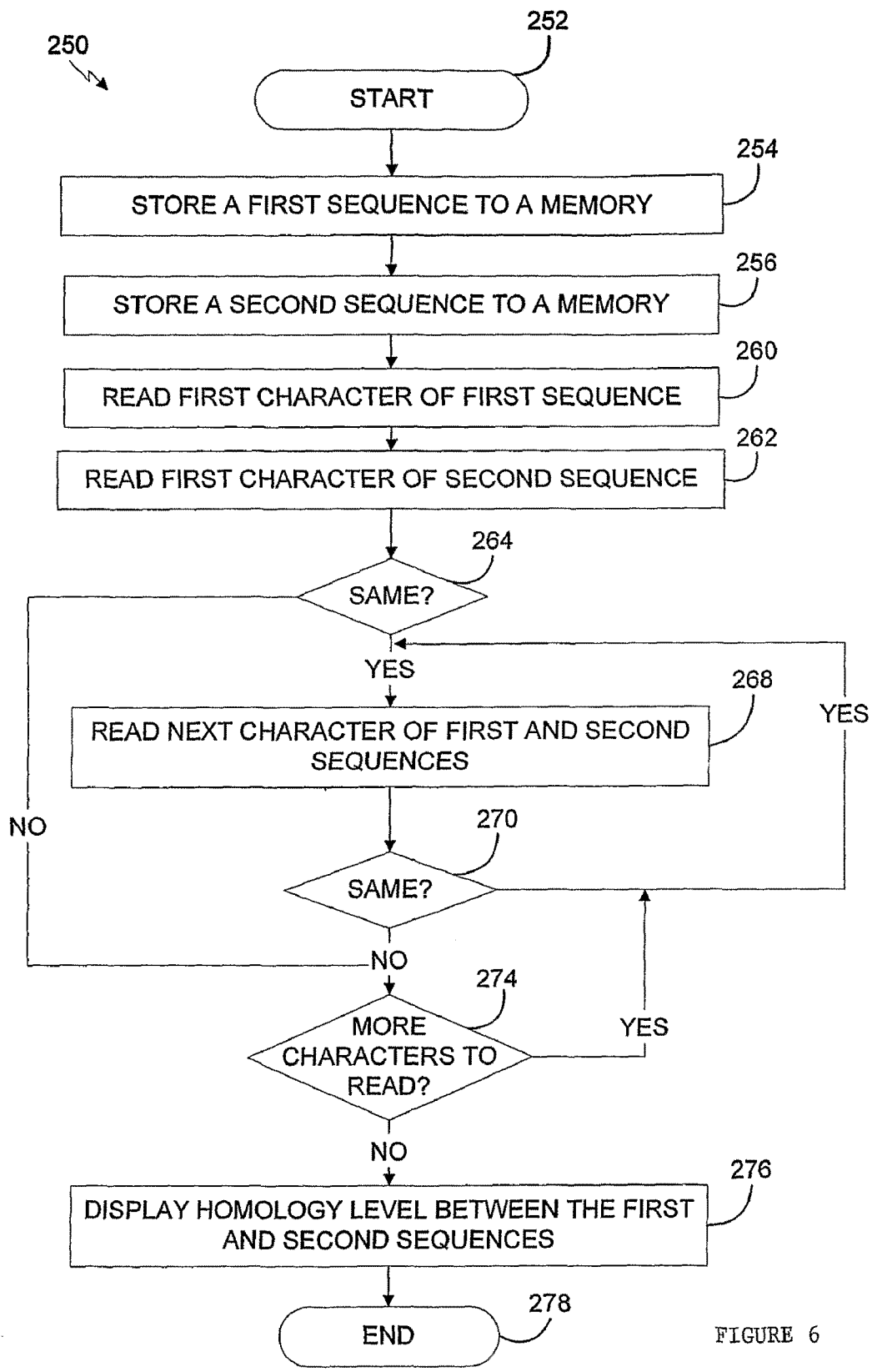
FIG. 6 is a flow diagram illustrating one aspect of a process in a computer for determining whether two sequences are homologous, as described in detail, below.

FIG. 6 is a flow diagram illustrating one aspect of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it is in one aspect in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of a nucleic acid sequence as set forth in the invention, to one or more reference nucleotide sequences in order to determine whether the nucleic acid code of the invention, differs from a reference nucleic acid sequence at one or more positions. Optionally such a program records the length and identity of inserted, deleted or substituted nucleotides with respect to the sequence of either the reference polynucleotide or a nucleic acid sequence of the invention. In one aspect, the computer program may be a program which determines whether a nucleic acid sequence of the invention, contains a single nucleotide polymorphism (SNP) with respect to a reference nucleotide sequence.

Accordingly, another aspect of the invention is a method for determining whether a nucleic acid sequence of the invention, differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some aspects, the computer program is a program which identifies single nucleotide polymorphisms. The method may be implemented by the computer systems described above and the method illustrated in FIG. 6. The method may also be performed by reading at least 2, 5, 10, 15, 20, 25, 30, or 40 or more of the nucleic acid sequences of the invention and the reference nucleotide sequences through the use of the computer program and identifying differences between the nucleic acid codes and the reference nucleotide sequences with the computer program.

In other aspects the computer based system may further comprise an identifier for identifying features within a nucleic acid sequence of the invention or a polypeptide sequence of the invention.

An "identifier" refers to one or more programs which identifies certain features within a nucleic acid sequence of the invention, or a polypeptide sequence of the invention. In one aspect, the identifier may comprise a program which identifies an open reading frame in a nucleic acid sequence of the invention.

Figure 7:
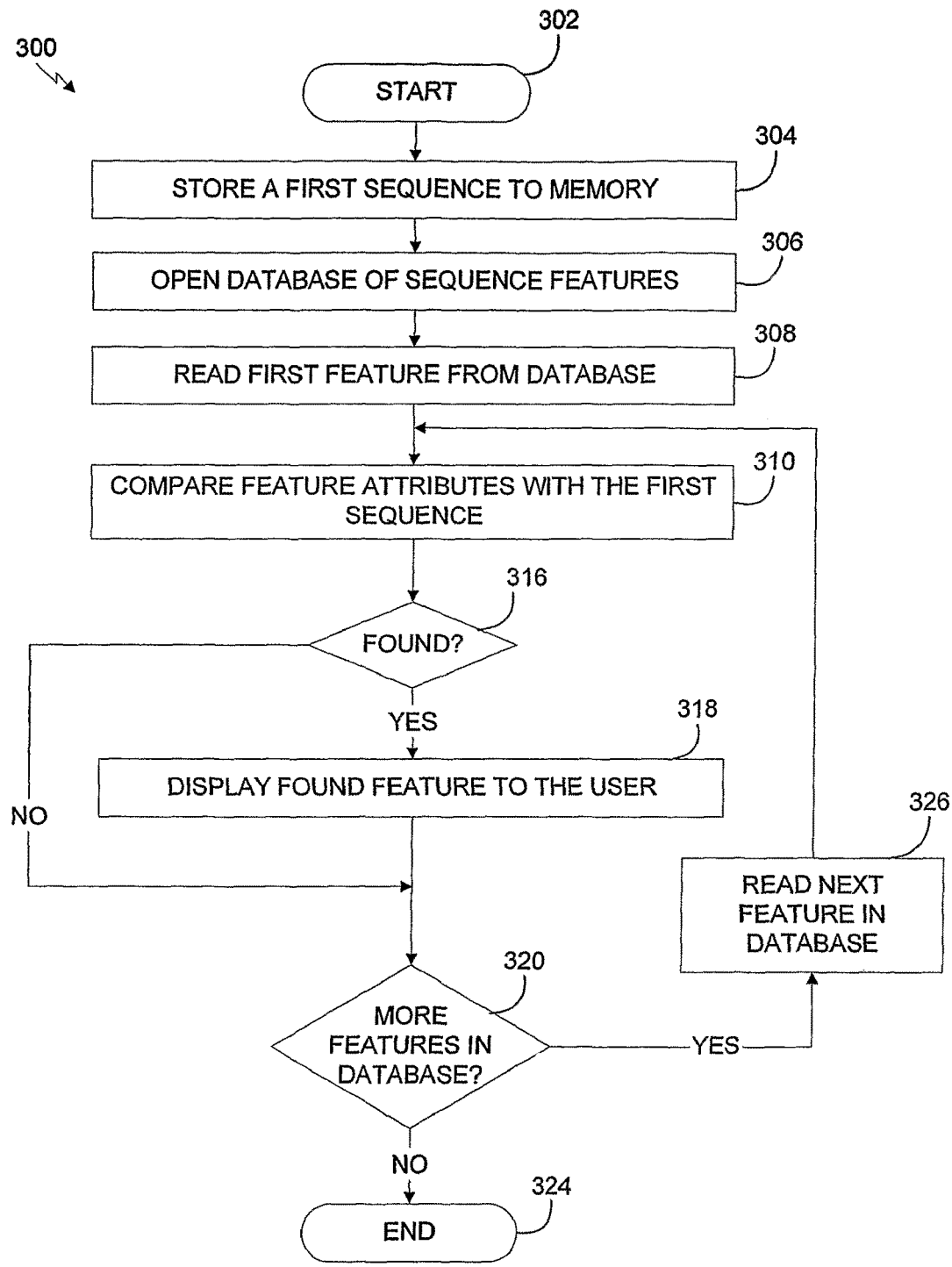
FIG. 7 is a flow diagram illustrating one aspect of an identifier process 300 for detecting the presence of a feature in a sequence, as described in detail, below.

FIG. 7 is a flow diagram illustrating one aspect of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group. Alternatively, the features may be structural polypeptide motifs such as alpha helices, beta sheets, or functional polypeptide motifs such as enzymatic catalytic domains (CDs), or, active sites, helix-turn-helix motifs or other motifs known to those skilled in the art.

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence. It should be noted, that if the feature attribute is not found in the first sequence at the decision state 316, the process 300 moves directly to the decision state 320 in order to determine if any more features exist in the database.

Accordingly, another aspect of the invention is a method of identifying a feature within a nucleic acid sequence of the invention, or a polypeptide sequence of the invention, comprising reading the nucleic acid code(s) or polypeptide code(s) through the use of a computer program which identifies features therein and identifying features within the nucleic acid code(s) with the computer program. In one aspect, computer program comprises a computer program which identifies open reading frames. The method may be performed by reading a single sequence or at least 2, 5, 10, 15, 20, 25, 30, or 40 of the nucleic acid sequences of the invention, or the polypeptide sequences of the invention, through the use of the computer program and identifying features within the nucleic acid codes or polypeptide codes with the computer program.

A nucleic acid sequence of the invention, or a polypeptide sequence of the invention, may be stored and manipulated in a variety of data processor programs in a variety of formats. For example, a nucleic acid sequence of the invention, or a polypeptide sequence of the invention, may be stored as text in a word processing file, such as Microsoft WORD™ or WORDPERFECT™ or as an ASCII file in a variety of database programs familiar to those of skill in the art, such as DB2™, SYBASE™, or ORACLE™. In addition, many computer programs and databases may be used as sequence comparison algorithms, identifiers, or sources of reference nucleotide sequences or polypeptide sequences to be compared to a nucleic acid sequence of the invention, or a polypeptide sequence of the invention. The following list is intended not to limit the invention but to provide guidance to programs and databases which are useful with the nucleic acid sequences of the invention, or the polypeptide sequences of the invention.

The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB (Brutlag et al. Comp. App. Biosci. 6:237-245, 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwents's World Drug Index database, the BioByteMasterFile database, the Genbank database and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices and beta sheets, signal sequences encoding signal peptides which direct the secretion of the encoded proteins, sequences implicated in transcription regulation such as homeoboxes, acidic stretches, enzymatic active sites (catalytic domains (CDs)), substrate binding sites and enzymatic cleavage sites.

Hybridization of Nucleic Acids

The invention provides isolated, synthetic or recombinant nucleic acids that hybridize under stringent conditions to an exemplary sequence of the invention (e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19). The stringent conditions can be highly stringent conditions, medium stringent conditions and/or low stringent conditions, including the high and reduced stringency conditions described herein. In one aspect, it is the stringency of the wash conditions that set forth the conditions which determine whether a nucleic acid is within the scope of the invention, as discussed below.

In alternative aspects, nucleic acids of the invention as defined by their ability to hybridize under stringent conditions can be between about five residues and the full length of nucleic acid of the invention; e.g., they can be at least 5, 10, 15, 20, 25, 30, 35, 40, 50, 55, 60, 65, 70, 75, 80, 90, 100, 150, 200, 250, 300, 350, 400, 450, 500, 550, 600, 650, 700, 750, 800, 850, 900, 950, 1000, or more, residues in length. Nucleic acids shorter than full length are also included. These nucleic acids can be useful as, e.g., hybridization probes, labeling probes, PCR oligonucleotide probes, iRNA (single or double stranded), antisense or sequences encoding antibody binding peptides (epitopes), motifs, active sites (catalytic domains (CDs)) and the like.

In one aspect, nucleic acids of the invention are defined by their ability to hybridize under high stringency comprises conditions of about 50% formamide at about 37° C. to 42° C. In one aspect, nucleic acids of the invention are defined by their ability to hybridize under reduced stringency comprising conditions in about 35% to 25% formamide at about 30° C. to 35° C.

Alternatively, nucleic acids of the invention are defined by their ability to hybridize under high stringency comprising conditions at 42° C. in 50% formamide, 5×SSPE, 0.3% SDS, and a repetitive sequence blocking nucleic acid, such as cot-1 or salmon sperm DNA (e.g., 200 n/ml sheared and denatured salmon sperm DNA). In one aspect, nucleic acids of the invention are defined by their ability to hybridize under reduced stringency conditions comprising 35% formamide at a reduced temperature of 35° C.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content) and nucleic acid type (e.g., RNA v. DNA) of the hybridizing regions of the nucleic acids can be considered in selecting hybridization conditions. An additional consideration is whether one of the nucleic acids is immobilized, for example, on a filter.

Hybridization may be carried out under conditions of low stringency, moderate stringency or high stringency. As an example of nucleic acid hybridization, a polymer membrane containing immobilized denatured nucleic acids is first prehybridized for 30 minutes at 45□ C. in a solution consisting of 0.9 M NaCl, 50 mM NaH$_2$PO$_4$, pH 7.0, 5.0 mM Na$_2$EDTA, 0.5% SDS, 10×Denhardt's and 0.5 mg/ml polyriboadenylic acid. Approximately 2×10$^7$ cpm (specific activity 4-9×10$^8$ cpm/ug) of $^{32}$P end-labeled oligonucleotide probe are then added to the solution. After 12-16 hours of incubation, the membrane is washed for 30 minutes at room temperature in 1×SET (150 mM NaCl, 20 mM Tris hydrochloride, pH 7.8, 1 mM Na$_2$EDTA) containing 0.5% SDS, followed by a 30 minute wash in fresh 1×SET at T$_m$-10□ C. for the oligonucleotide probe. The membrane is then exposed to auto-radiographic film for detection of hybridization signals.

All of the foregoing hybridizations would be considered to be under conditions of high stringency.

Following hybridization, a filter can be washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content) and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes. Some other examples are given below.

Nucleic acids which have hybridized to the probe are identified by autoradiography or other conventional techniques.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5□C. from 68□C. to 42□C. in a hybridization buffer having a Na+ concentration of approximately 1M. Following hybridization, the filter may be washed with 2×SSC, 0.5% SDS at the temperature of hybridization. These conditions are considered to be "moderate" conditions above 50□C. and "low" conditions below 50□C. A specific example of "moderate" hybridization conditions is when the above hybridization is conducted at 55□C. A specific example of "low stringency" hybridization conditions is when the above hybridization is conducted at 45□C.

Alternatively, the hybridization may be carried out in buffers, such as 6×SSC, containing formamide at a temperature of 42□C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50□C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook, Tijssen and Ausubel for a description of SSC buffer and equivalent conditions.

These methods may be used to isolate nucleic acids of the invention. For example, the preceding methods may be used to isolate nucleic acids having a sequence with at least about 97%, at least 95%, at least 90%, at least 85%, at least 80%, at least 75%, at least 70%, at least 65%, at least 60%, at least 55%, or at least 50% homology to a nucleic acid sequence selected from the group consisting of one of the sequences of the invention, or fragments comprising at least about 10, 15, 20, 25, 30, 35, 40, 50, 75, 100, 150, 200, 300, 400, or 500 consecutive bases thereof and the sequences complementary thereto. Homology may be measured using the alignment algorithm. For example, the homologous polynucleotides may have a coding sequence which is a naturally occurring allelic variant of one of the coding sequences described herein. Such allelic variants may have a substitution, deletion or addition of one or more nucleotides when compared to the nucleic acids of the invention.

Additionally, the above procedures may be used to isolate nucleic acids which encode polypeptides having at least about 99%, 95%, at least 90%, at least 85%, at least 80%, at least 75%, at least 70%, at least 65%, at least 60%, at least 55%, or at least 50% homology to a polypeptide of the invention, or fragments comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters).

Oligonucleotides Probes and Methods for Using them

The invention also provides nucleic acid probes that can be used, e.g., for identifying nucleic acids encoding a polypeptide with an enzyme activity or fragments thereof or for identifying genes or other nucleic acids encoding polypeptides having a chlorophyllase enzyme activity or enzymes involved in the catabolism of chlorophyll. In one aspect, the probe comprises at least 10 consecutive bases of a nucleic acid of the invention. Alternatively, a probe of the invention can be at least about 5, 6, 7, 8, 9, 10, 11, 12, 13, 14, 15, 16, 17, 18, 19, 20, 21, 22, 23, 24, 25, 30, 35, 40, 45, 50, 60, 70, 80, 90, 100, 110, 120, 130, 150 or about 10 to 50, about 20 to 60 about 30 to 70, consecutive bases of a sequence as set forth in a nucleic acid of the invention. The probes identify a nucleic acid by binding and/or hybridization. The probes can be used in arrays of the invention, see discussion below, including, e.g., capillary arrays. The probes of the invention can also be used to isolate other nucleic acids or polypeptides.

The isolated nucleic acids of the invention, the sequences complementary thereto, or a fragment comprising at least 10, 15, 20, 25, 30, 35, 40, 50, 75, 100, 150, 200, 300, 400, or 500 consecutive bases of one of the sequences of the invention, or the sequences complementary thereto may also be used as probes to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences from which are present therein.

Where necessary, conditions which permit the probe to specifically hybridize to complementary sequences may be determined by placing the probe in contact with complementary sequences from samples known to contain the complementary sequence as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids.

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product.

Many methods for using the labeled probes to detect the presence of complementary nucleic acids in a sample are familiar to those skilled in the art. These include Southern Blots, Northern Blots, colony hybridization procedures and dot blots. Protocols for each of these procedures are provided in Ausubel et al. *Current Protocols in Molecular Biology*, John Wiley 503 Sons, Inc. (1997) and Sambrook et al., *Molecular Cloning: A Laboratory Manual 2nd Ed.*, Cold Spring Harbor Laboratory Press (1989.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). Typically, the probes comprise oligonucleotides. In one aspect, the amplification reaction may comprise a PCR reaction. PCR protocols are described in Ausubel and Sambrook, supra. Alternatively, the amplification may comprise a ligase chain reaction, 3 SR, or strand displacement reaction. (See Barany, F., "The Ligase Chain Reaction in a PCR World", *PCR Methods and Applications* 1:5-16, 1991; E. Fahy et al., "Self-sustained Sequence Replication (3SR): An Isothermal Transcription-based Amplification System Alternative to PCR", *PCR Methods and Applications* 1:25-33, 1991; and Walker G. T. et al., "Strand Displacement Amplification—an Isothermal in vitro DNA Amplification Technique", *Nucleic Acid Research* 20:1691-1696, 1992). In such procedures, the nucleic acids in the sample are contacted with the probes, the amplification reaction is performed and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the ends of the sequences of the invention, may also be used in chromosome walking procedures to identify clones containing genomic sequences located adjacent to the sequences of the invention. Such methods allow the isolation of genes which encode additional proteins from the host organism.

The isolated nucleic acids of the invention, the sequences complementary thereto, or a fragment comprising at least 10, 15, 20, 25, 30, 35, 40, 50, 75, 100, 150, 200, 300, 400, or 500 consecutive bases of one of the sequences of the invention, or the sequences complementary thereto may be used as probes to identify and isolate related nucleic acids. In some aspects, the related nucleic acids may be cDNAs or genomic DNAs from organisms other than the one from which the nucleic acid was isolated. For example, the other organisms may be related organisms. In such procedures, a nucleic acid sample is contacted with the probe under conditions which permit the probe to specifically hybridize to related sequences. Hybridization of the probe to nucleic acids from the related organism is then detected using any of the methods described above.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, $T_m$, is the temperature (under defined ionic strength and pH) at which 50% of the target sequence hybridizes to a perfectly complementary probe. Very stringent conditions are selected to be equal to or about 5° C. lower than the $T_m$ for a particular probe. The melting temperature of the probe may be calculated using the following formulas:

For probes between 14 and 70 nucleotides in length the melting temperature ($T_m$) is calculated using the formula: $T_m=81.5+16.6(\log [Na+])+0.41(\text{fraction } G+C)-(600/N)$ where N is the length of the probe.

If the hybridization is carried out in a solution containing formamide, the melting temperature may be calculated using the equation: $T_m=81.5+16.6(\log [Na+])+0.41(\text{fraction } G+C)-(0.63\% \text{ formamide})-(600/N)$ where N is the length of the probe.

Prehybridization may be carried out in 6×SSC, 5×Denhardt's reagent, 0.5% SDS, 100 □g denatured fragmented salmon sperm DNA or 6×SSC, 5×Denhardt's reagent, 0.5% SDS, 100 □g denatured fragmented salmon sperm DNA, 50% formamide. The formulas for SSC and Denhardt's solutions are listed in Sambrook et al., supra.

In one aspect, hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the $T_m$. For shorter probes, such as oligonucleotide probes, the hybridization may be conducted at 5-10° C. below the $T_m$. In one aspect, for hybridizations in 6×SSC, the hybridization is conducted at approximately 68° C. In one aspect, for hybridizations in 50% formamide containing solutions, the hybridization is conducted at approximately 42° C.

Inhibiting Expression of Enzymes

The invention provides nucleic acids complementary to (e.g., antisense sequences to) the nucleic acids of the invention, e.g., nucleic acids encoding polypeptides having an enzyme activity involved in chlorophyll catabolism or having an esterase (e.g., chlorophyllase) activity. Antisense sequences are capable of inhibiting the transport, splicing or transcription of enzyme-encoding genes. The inhibition can be effected through the targeting of genomic DNA or messenger RNA. The transcription or function of targeted nucleic acid can be inhibited, for example, by hybridization and/or cleavage. One particularly useful set of inhibitors provided by the present invention includes oligonucleotides which are able to either bind gene or message, in either case preventing or inhibiting the production or function of the desired enzyme. The association can be through sequence specific hybridization. Another useful class of inhibitors includes oligonucleotides which cause inactivation or cleavage of nucleic acids encoding polypeptides having an enzyme activity involved in chlorophyll catabolism or having an esterase (e.g., chlorophyllase) activity. The oligonucleotide can have enzyme activity which causes such cleavage, such as ribozymes. The oligonucleotide can be chemically modified or conjugated to an enzyme or composition capable of cleaving the complementary nucleic acid. A pool of many different such oligonucleotides can be screened for those with the desired activity. Thus, the invention provides various compositions for the inhibition of enzyme expression on a nucleic acid and/or protein level, e.g., antisense, iRNA and ribozymes comprising nucleic acid sequences of the invention and antibodies of the invention.

Inhibition of expression of nucleic acids encoding polypeptides having an enzyme activity involved in chlorophyll catabolism or having an esterase (e.g., chlorophyllase) activity can have a variety of industrial applications. For example, compositions of the invention for the inhibition of enzyme expression (e.g., antisense, iRNA, ribozymes, antibodies) can be used as pharmaceutical compositions, e.g., as anti-pathogen agents or in other therapies, e.g., where the inhibited enzyme has an undesired, deleterious or toxic effect.

Antisense Oligonucleotides

The invention provides antisense oligonucleotides capable of binding enzyme message or a gene which can inhibit a target gene or message to, e.g., inhibit a polypeptide involved in chlorophyll catabolism or having an esterase (e.g., chlorophyllase) activity by targeting mRNA. Strategies for designing antisense oligonucleotides are well described in the scientific and patent literature, and the skilled artisan can design such oligonucleotides using the novel reagents of the invention. For example, gene walking/RNA mapping protocols to screen for effective antisense oligonucleotides are well known in the art, see, e.g., Ho (2000) Methods Enzymol. 314:168-183, describing an RNA mapping assay, which is based on standard molecular techniques to provide an easy and reliable method for potent antisense sequence selection. See also Smith (2000) Eur. J. Pharm. Sci. 11:191-198.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl)glycine units can be used. Antisense oligonucleotides having phosphorothioate linkages can also be used, as described in WO 97/03211; WO 96/39154; Mata (1997) Toxicol Appl Pharmacol 144:189-197; Antisense Therapeutics, ed. Agrawal (Humana Press, Totowa, N.J., 1996). Antisense oligonucleotides having synthetic DNA backbone analogues provided by the invention can also include phosphorodithioate, methylphosphonate, phosphoramidate, alkyl phosphotriester, sulfamate, 3'-thioacetal, methylene(methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense sequences of the invention (see, e.g., Gold (1995) J. of Biol. Chem. 270:13581-13584).

Inhibitory Ribozymes

The invention provides ribozymes capable of binding message or genes encoding polypeptides of the invention, or, encoding polypeptides involved in chlorophyll catabolism or having an esterase (e.g., chlorophyllase) activity. These ribozymes can inhibit activity by, e.g., targeting mRNA. Strategies for designing ribozymes and selecting the enzyme-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it can be released from that RNA to bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The ribozyme of the invention, e.g., an enzymatic ribozyme RNA molecule, can be formed in a hammerhead motif, a hairpin motif, as a hepatitis delta virus motif, a group I intron motif and/or an RNaseP-like RNA in association with an RNA guide sequence. Examples of hammerhead motifs are described by, e.g., Rossi (1992) Aids Research and Human Retroviruses 8:183; hairpin motifs by Hampel (1989) Biochemistry 28:4929, and Hampel (1990) Nuc. Acids Res. 18:299; the hepatitis delta virus motif by Perrotta (1992) Biochemistry 31:16; the RNaseP motif by Guerrier-Takada (1983) Cell 35:849; and the group I intron by Cech U.S. Pat. No. 4,987,071. The recitation of these specific motifs is not intended to be limiting. Those skilled in the art will recognize that a ribozyme of the invention, e.g., an enzymatic RNA molecule of this invention, can have a specific substrate binding site complementary to one or more of the target gene RNA regions. A ribozyme of the invention can have a nucleotide sequence within or surrounding that substrate binding site which imparts an RNA cleaving activity to the molecule.

RNA Interference (RNAi)

In one aspect, the invention provides an RNA inhibitory molecule, a so-called "RNAi" molecule, comprising a sequence of the invention. The RNAi molecule comprises a double-stranded RNA (dsRNA) molecule. The RNAi can inhibit expression of a nucleic acid encoding a polypeptide involved in chlorophyll catabolism or having an esterase (e.g., chlorophyllase) activity, e.g., as described herein. In one aspect, the RNAi is about 15, 16, 17, 18, 19, 20, 21, 22, 23, 24, 25 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi is the breaking of a double-stranded RNA (dsRNA) matching a specific gene sequence into short pieces called short interfering RNA, which trigger the degradation of mRNA that matches its sequence. In one aspect, the RNAi's of the invention are used in gene-silencing therapeutics, see, e.g., Shuey (2002) Drug Discov. Today 7:1040-1046. In one aspect, the invention provides methods to selectively degrade RNA using the RNAi's of the invention. The process may be practiced in vitro, ex vivo or in vivo. In one aspect, the RNAi molecules of the invention can be used to generate a loss-of-function mutation in a cell, an organ or an animal. Methods for making and using RNAi molecules for selectively degrade RNA are well known in the art, see, e.g., U.S. Pat. Nos. 6,506,559; 6,511,824; 6,515,109; 6,489,127.

Modification of Nucleic Acids

The invention provides methods of generating variants of the nucleic acids of the invention, e.g., those encoding a polypeptide involved in chlorophyll catabolism or having an esterase (e.g., chlorophyllase) activity, e.g., enzymes described herein. These methods can be repeated or used in various combinations to generate polypeptides involved in chlorophyll catabolism or having an esterase (e.g., chlorophyllase) activity having an altered or different activity or an altered or different stability from that of an enzyme encoded by the template nucleic acid. These methods also can be repeated or used in various combinations, e.g., to generate variations in gene/message expression, message translation or message stability. In another aspect, the genetic composition of a cell is altered by, e.g., modification of a homologous gene ex vivo, followed by its reinsertion into the cell.

A nucleic acid of the invention can be altered by any means. For example, random or stochastic methods, or, non-stochastic, or "directed evolution," methods, see, e.g., U.S. Pat. No. 6,361,974. Methods for random mutation of genes are well known in the art, see, e.g., U.S. Pat. No. 5,830,696. For example, mutagens can be used to randomly mutate a gene. Mutagens include, e.g., ultraviolet light or gamma irradiation, or a chemical mutagen, e.g., mitomycin, nitrous acid, photo-activated psoralens, alone or in combination, to induce DNA breaks amenable to repair by recombination. Other chemical mutagens include, for example, sodium bisulfite, nitrous acid, hydroxylamine, hydrazine or formic acid. Other mutagens are analogues of nucleotide precursors, e.g., nitrosoguanidine, 5-bromouracil, 2-aminopurine, or acridine. These agents can be added to a PCR reaction in place of the nucleotide precursor thereby mutating the sequence. Intercalating agents such as proflavine, acriflavine, quinacrine and the like can also be used.

Any technique in molecular biology can be used, e.g., random PCR mutagenesis, see, e.g., Rice (1992) Proc. Natl. Acad. Sci. USA 89:5467-5471; or, combinatorial multiple cassette mutagenesis, see, e.g., Crameri (1995) Biotechniques 18:194-196. Alternatively, nucleic acids, e.g., genes, can be reassembled after random, or "stochastic," fragmentation, see, e.g., U.S. Pat. Nos. 6,291,242; 6,287,862; 6,287, 861; 5,955,358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis™ (GSSM™), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

The following publications describe a variety of recursive recombination procedures and/or methods which can be incorporated into the methods of the invention: Stemmer (1999) "Molecular breeding of viruses for targeting and other clinical properties" Tumor Targeting 4:1-4; Ness (1999) Nature Biotechnology 17:893-896; Chang (1999) "Evolution of a cytokine using DNA family shuffling" Nature Biotechnology 17:793-797; Minshull (1999) "Protein evolution by molecular breeding" Current Opinion in Chemical Biology 3:284-290; Christians (1999) "Directed evolution of thymidine kinase for AZT phosphorylation using DNA family shuffling" Nature Biotechnology 17:259-264; Crameri (1998) "DNA shuffling of a family of genes from diverse species accelerates directed evolution" Nature 391:288-291; Crameri (1997) "Molecular evolution of an arsenate detoxification pathway by DNA shuffling," Nature Biotechnology 15:436-438; Zhang (1997) "Directed evolution of an effective fucosidase from a galactosidase by DNA shuffling and screening" Proc. Natl. Acad. Sci. USA 94:4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Gates et al. (1996) "Affinity selective isolation of ligands from peptide libraries through display on a lac repressor 'headpiece dimer'" Journal of Molecular Biology 255: 373-386; Stemmer (1996) "Sexual PCR and Assembly PCR" In: The Encyclopedia of Molecular Biology. VCH Publishers, New York. pp. 447-457; Crameri and Stemmer (1995) "Combinatorial multiple cassette mutagenesis creates all the permutations of mutant and wildtype cassettes" BioTechniques 18:194-195; Stemmer et al. (1995) "Single-step assembly of a gene and entire plasmid form large numbers of oligodeoxyribonucleotides" Gene, 164:49-53; Stemmer (1995) "The Evolution of Molecular Computation" Science 270: 1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: In vitro recombination for molecular evolution." Proc. Natl. Acad. Sci. USA 91:10747-10751.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100:468-500; and Zoller (1987) Oligonucleotide-directed mutagenesis: a simple method using two oligonucleotide primers and a single-stranded DNA template" Methods in Enzymol. 154: 329-350); phosphorothioate-modified DNA mutagenesis (Taylor (1985) "The use of phosphorothioate-modified DNA in restriction enzyme reactions to prepare nicked DNA" Nucl. Acids Res. 13: 8749-8764; Taylor (1985) "The rapid generation of oligonucleotide-directed mutations at high frequency using phosphorothioate-modified DNA" Nucl. Acids Res. 13: 8765-8787 (1985); Nakamaye (1986) "Inhibition of restriction endonuclease Nci I cleavage by phosphorothioate groups and its application to oligonucleotide-directed mutagenesis" Nucl. Acids Res. 14: 9679-9698; Sayers (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154:350-367; Kramer (1988) "Improved enzymatic in vitro reactions in the gapped duplex DNA approach to oligonucleotide-directed construction of mutations" Nucl. Acids Res. 16: 7207; and Fritz (1988) "Oligonucleotide-directed construction of mutations: a gapped duplex DNA procedure without enzymatic reactions in vitro" Nucl. Acids Res. 16: 6987-6999).

Additional protocols that can be used to practice the invention include point mismatch repair (Kramer (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh (1986) "Use of oligonucleotides to generate large deletions" Nucl. Acids Res. 14: 5115), restriction-selection and restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shot-gun' gene synthesis" Nucl. Acids Res. 13: 3305-3316), double-strand break repair (Mandecki (1986); Arnold (1993) "Protein engineering for unusual environments" Current Opinion in Biotechnology 4:450-455. "Oligonucleotide-directed double-strand break repair in plasmids of *Escherichia coli*: a method for site-specific mutagenesis" Proc. Natl. Acad. Sci. USA, 83:7177-7181). Additional details on many of the above methods can be found in Methods in Enzymology Volume 154, which also describes useful controls for trouble-shooting problems with various mutagenesis methods.

Protocols that can be used to practice the invention are described, e.g., in U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

Protocols that can be used to practice the invention (providing details regarding various diversity generating methods) are described, e.g., in U.S. patent application Ser. No. (USSN) 09/407,800, "SHUFFLING OF CODON ALTERED GENES" by Patten et al. filed Sep. 28, 1999; "EVOLUTION OF WHOLE CELLS AND ORGANISMS BY RECURSIVE SEQUENCE RECOMBINATION" by del Cardayre et al., U.S. Pat. No. 6,379,964; "OLIGONUCLEOTIDE MEDIATED NUCLEIC ACID RECOMBINATION" by Crameri et al., U.S. Pat. Nos. 6,319,714; 6,368,861; 6,376,246; 6,423,542; 6,426,224 and PCT/US00/01203; "USE OF CODON-VARIED OLIGONUCLEOTIDE SYNTHESIS FOR SYNTHETIC SHUFFLING" by Welch et al., U.S. Pat. No. 6,436,675; "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g. "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549); and U.S. Pat. Nos. 6,177,263; 6,153,410.

Non-stochastic, or "directed evolution," methods include, e.g., Gene Site Saturation Mutagenesis (GSSM), synthetic ligation reassembly (SLR), or a combination thereof are used to modify the nucleic acids of the invention to generate polypeptides involved in chlorophyll catabolism or having an esterase (e.g., chlorophyllase) activity with new or altered properties (e.g., activity under highly acidic or alkaline conditions, high or low temperatures, and the like). Polypeptides encoded by the modified nucleic acids can be screened for an activity before testing for glucan or other polysaccharide hydrolysis or other activity. Any testing modality or protocol can be used, e.g., using a capillary array platform. See, e.g., U.S. Pat. Nos. 6,361,974; 6,280,926; 5,939,250.

Gene Site Saturation Mutagenesis (GSSM)

In one aspect, codon primers containing a degenerate N,N, G/T sequence are used to introduce point mutations into a polynucleotide, e.g., a nucleic acid of the invention, so as to generate a set of progeny polypeptides in which a full range of single amino acid substitutions is represented at each amino acid position, e.g., an amino acid residue in an enzyme active site (catalytic domains (CDs)) or ligand binding site targeted to be modified. These oligonucleotides can comprise a contiguous first homologous sequence, a degenerate N,N,G/T sequence, and, optionally, a second homologous sequence. The downstream progeny translational products from the use of such oligonucleotides include all possible amino acid changes at each amino acid site along the polypeptide, because the degeneracy of the N,N,G/T sequence includes codons for all 20 amino acids. In one aspect, one such degenerate oligonucleotide (comprised of, e.g., one degenerate N,N,G/T cassette) is used for subjecting each original codon in a parental polynucleotide template to a full range of codon substitutions. In another aspect, at least two degenerate cassettes are used—either in the same oligonucleotide or not, for subjecting at least two original codons in a parental polynucleotide template to a full range of codon substitutions. For example, more than one N,N,G/T sequence can be contained in one oligonucleotide to introduce amino acid mutations at more than one site. This plurality of N,N,G/T sequences can be directly contiguous, or separated by one or more additional nucleotide sequence(s). In another aspect, oligonucleotides serviceable for introducing additions and deletions can be used either alone or in combination with the codons containing an N,N,G/T sequence, to introduce any combination or permutation of amino acid additions, deletions, and/or substitutions.

In one aspect, simultaneous mutagenesis of two or more contiguous amino acid positions is done using an oligonucleotide that contains contiguous N,N,G/T triplets, i.e. a degenerate (N,N,G/T)n sequence. In another aspect, degenerate cassettes having less degeneracy than the N,N,G/T sequence are used. For example, it may be desirable in some instances to use (e.g. in an oligonucleotide) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g. in an oligo) a degenerate N,N,N triplet sequence.

In one aspect, use of degenerate triplets (e.g., N,N,G/T triplets) allows for systematic and easy generation of a full range of possible natural amino acids (for a total of 20 amino acids) into each and every amino acid position in a polypeptide (in alternative aspects, the methods also include generation of less than all possible substitutions per amino acid residue, or codon, position). For example, for a 100 amino acid polypeptide, 2000 distinct species (i.e. 20 possible amino acids per position X 100 amino acid positions) can be generated. Through the use of an oligonucleotide or set of oligonucleotides containing a degenerate N,N,G/T triplet, 32 individual sequences can code for all 20 possible natural amino acids. Thus, in a reaction vessel in which a parental polynucleotide sequence is subjected to saturation mutagenesis using at least one such oligonucleotide, there are generated 32 distinct progeny polynucleotides encoding 20 distinct polypeptides. In contrast, the use of a non-degenerate oligonucleotide in site-directed mutagenesis leads to only one progeny polypeptide product per reaction vessel. Nondegenerate oligonucleotides can optionally be used in combination with degenerate primers disclosed; for example, nondegenerate oligonucleotides can be used to generate specific point mutations in a working polynucleotide. This provides one means to generate specific silent point mutations, point mutations leading to corresponding amino acid changes, and point mutations that cause the generation of stop codons and the corresponding expression of polypeptide fragments.

In one aspect, each saturation mutagenesis reaction vessel contains polynucleotides encoding at least 20 progeny polypeptide (e.g., polypeptides of the invention involved in chlorophyll catabolism or having an esterase (e.g., chlorophyllase) activity) molecules such that all 20 natural amino acids are represented at the one specific amino acid position corresponding to the codon position mutagenized in the parental polynucleotide (other aspects use less than all 20 natural combinations). The 32-fold degenerate progeny polypeptides generated from each saturation mutagenesis reaction vessel can be subjected to clonal amplification (e.g. cloned into a suitable host, e.g., *E. coli* host, using, e.g., an expression vector) and subjected to expression screening. When an individual progeny polypeptide is identified by screening to display a favorable change in property (when compared to the parental polypeptide, such as increased glucan hydrolysis activity under alkaline or acidic conditions), it can be sequenced to identify the correspondingly favorable amino acid substitution contained therein.

In one aspect, upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined–6 single point mutations (i.e. 2 at each of three positions) and no change at any position.

In yet another aspect, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

The invention also provides for the use of proprietary codon primers (containing a degenerate N,N,N sequence) to introduce point mutations into a polynucleotide, so as to generate a set of progeny polypeptides in which a full range of single amino acid substitutions is represented at each amino acid position (Gene Site Saturation Mutagenesis™ (GSSM™)). The oligos used are comprised contiguously of a first homologous sequence, a degenerate N,N,N sequence and in one aspect but not necessarily a second homologous sequence. The downstream progeny translational products from the use of such oligos include all possible amino acid changes at each amino acid site along the polypeptide, because the degeneracy of the N,N,N sequence includes codons for all 20 amino acids.

In one aspect, one such degenerate oligo (comprised of one degenerate N,N,N cassette) is used for subjecting each original codon in a parental polynucleotide template to a full range of codon substitutions. In another aspect, at least two degenerate N,N,N cassettes are used—either in the same oligo or not, for subjecting at least two original codons in a parental polynucleotide template to a full range of codon substitutions. Thus, more than one N,N,N sequence can be contained in one oligo to introduce amino acid mutations at more than one site. This plurality of N,N,N sequences can be directly contiguous, or separated by one or more additional nucleotide sequence(s). In another aspect, oligos serviceable for introducing additions and deletions can be used either alone or in combination with the codons containing an N,N,N sequence, to introduce any combination or permutation of amino acid additions, deletions and/or substitutions.

In a particular exemplification, it is possible to simultaneously mutagenize two or more contiguous amino acid positions using an oligo that contains contiguous N,N,N triplets, i.e. a degenerate $(N,N,N)_n$ sequence.

In another aspect, the present invention provides for the use of degenerate cassettes having less degeneracy than the N,N,N sequence. For example, it may be desirable in some instances to use (e.g. in an oligo) a degenerate triplet sequence comprised of only one N, where the N can be in the first second or third position of the triplet. Any other bases including any combinations and permutations thereof can be used in the remaining two positions of the triplet. Alternatively, it may be desirable in some instances to use (e.g., in an oligo) a degenerate N,N,N triplet sequence, N,N,G/T, or an N,N, G/C triplet sequence.

It is appreciated, however, that the use of a degenerate triplet (such as N,N,G/T or an N,N, G/C triplet sequence) as disclosed in the instant invention is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the invention provides a way to systematically and fairly easily generate 2000 distinct species (i.e., 20 possible amino acids per position times 100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes and point mutations that cause the generation of stop codons and the corresponding expression of polypeptide fragments.

Thus, in one aspect of this invention, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g., cloned into a suitable *E. coli* host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

It is appreciated that upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid and each of two favorable changes) and 3 positions. Thus, there are 3×3×3 or 27 total possibilities, including 7 that were previously examined —6 single point mutations (i.e., 2 at each of three positions) and no change at any position.

Thus, in a non-limiting exemplification, this invention provides for the use of saturation mutagenesis in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, the instant invention provides that mutagenesis can be use to replace each of any number of bases in a polynucleotide sequence, wherein the number of bases to be mutagenized is in one aspect every integer from 15 to 100,000. Thus, instead of mutagenizing every position along a molecule, one can subject every or a discrete number of bases (in one aspect a subset totaling from 15 to 100,000) to mutagenesis. In one aspect, a separate nucleotide is used for mutagenizing each position or group of positions along a polynucleotide sequence. A group of 3 positions to be mutagenized may be a codon. The mutations can be introduced using a mutagenic primer, containing a heterologous cassette, also referred to as a mutagenic cassette. Exemplary cassettes can have from 1 to 500 bases. Each nucleotide position in such heterologous cassettes be N, A, C, G, T, A/C, A/G, A/T, C/G, C/T, G/T, C/G/T, A/G/T, A/C/T, A/C/G, or E, where E is any base that is not A, C, G, or T (E can be referred to as a designer oligo).

In a general sense, saturation mutagenesis is comprised of mutagenizing a complete set of mutagenic cassettes (wherein each cassette is in one aspect about 1-500 bases in length) in defined polynucleotide sequence to be mutagenized (wherein the sequence to be mutagenized is in one aspect from about 15 to 100,000 bases in length). Thus, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons and groupings of particular nucleotide cassettes.

Defined sequences to be mutagenized include a whole gene, pathway, cDNA, an entire open reading frame (ORF) and entire promoter, enhancer, repressor/transactivator, origin of replication, intron, operator, or any polynucleotide functional group. Generally, a "defined sequences" for this purpose may be any polynucleotide that a 15 base-polynucleotide sequence and polynucleotide sequences of lengths between 15 bases and 15,000 bases (this invention specifically names every integer in between). Considerations in choosing groupings of codons include types of amino acids encoded by a degenerate mutagenic cassette.

In one exemplification a grouping of mutations that can be introduced into a mutagenic cassette, this invention specifically provides for degenerate codon substitutions (using degenerate oligos) that code for 2, 3, 4, 5, 6, 7, 8, 9, 10, 11, 12, 13, 14, 15, 16, 17, 18, 19 and 20 amino acids at each position and a library of polypeptides encoded thereby.

Synthetic Ligation Reassembly (SLR)

The invention provides a non-stochastic gene modification system termed "synthetic ligation reassembly," or simply "SLR," a "directed evolution process," to generate polypeptides, e.g., enzymes of the invention, with new or altered properties.

SLR is a method of ligating oligonucleotide fragments together non-stochastically. This method differs from stochastic oligonucleotide shuffling in that the nucleic acid building blocks are not shuffled, concatenated or chimerized randomly, but rather are assembled non-stochastically. See, e.g., U.S. patent application Ser. No. (USSN) 09/332,835 entitled "Synthetic Ligation Reassembly in Directed Evolution" and filed on Jun. 14, 1999 ("U.S. Ser. No. 09/332,835"). In one aspect, SLR comprises the following steps: (a) providing a template polynucleotide, wherein the template polynucleotide comprises sequence encoding a homologous gene; (b) providing a plurality of building block polynucleotides, wherein the building block polynucleotides are designed to cross-over reassemble with the template polynucleotide at a predetermined sequence, and a building block polynucleotide comprises a sequence that is a variant of the homologous gene and a sequence homologous to the template polynucleotide flanking the variant sequence; (c) combining a building block polynucleotide with a template polynucleotide such that the building block polynucleotide cross-over reassembles with the template polynucleotide to generate polynucleotides comprising homologous gene sequence variations.

SLR does not depend on the presence of high levels of homology between polynucleotides to be rearranged. Thus, this method can be used to non-stochastically generate libraries (or sets) of progeny molecules comprised of over $10^{100}$ different chimeras. SLR can be used to generate libraries comprised of over $10^{1000}$ different progeny chimeras. Thus, aspects of the present invention include non-stochastic methods of producing a set of finalized chimeric nucleic acid molecule shaving an overall assembly order that is chosen by design. This method includes the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, the overall assembly order in which the nucleic acid building blocks can be coupled is specified by the design of the ligatable ends. If more than one assembly step is to be used, then the overall assembly order in which the nucleic acid building blocks can be coupled is also specified by the sequential order of the assembly step(s). In one aspect, the annealed building pieces are treated with an enzyme, such as a ligase (e.g. T4 DNA ligase), to achieve covalent bonding of the building pieces.

In one aspect, the design of the oligonucleotide building blocks is obtained by analyzing a set of progenitor nucleic acid sequence templates that serve as a basis for producing a progeny set of finalized chimeric polynucleotides. These parental oligonucleotide templates thus serve as a source of sequence information that aids in the design of the nucleic acid building blocks that are to be mutagenized, e.g., chimerized or shuffled. In one aspect of this method, the sequences of a plurality of parental nucleic acid templates are aligned in order to select one or more demarcation points. The demarcation points can be located at an area of homology, and are comprised of one or more nucleotides. These demarcation points are in one aspect shared by at least two of the progenitor templates. The demarcation points can thereby be used to delineate the boundaries of oligonucleotide building blocks to be generated in order to rearrange the parental polynucleotides. The demarcation points identified and selected in the progenitor molecules serve as potential chimerization points in the assembly of the final chimeric progeny molecules. A demarcation point can be an area of homology (comprised of at least one homologous nucleotide base) shared by at least two parental polynucleotide sequences. Alternatively, a demarcation point can be an area of homology that is shared by at least half of the parental polynucleotide sequences, or, it can be an area of homology that is shared by at least two thirds of the parental polynucleotide sequences. Even more in one aspect a serviceable demarcation points is an area of homology that is shared by at least three fourths of the parental polynucleotide sequences, or, it can be shared by at almost all of the parental polynucleotide sequences. In one aspect, a demarcation point is an area of homology that is shared by all of the parental polynucleotide sequences.

In one aspect, a ligation reassembly process is performed exhaustively in order to generate an exhaustive library of progeny chimeric polynucleotides. In other words, all possible ordered combinations of the nucleic acid building blocks are represented in the set of finalized chimeric nucleic acid molecules. At the same time, in another aspect, the assembly order (i.e. the order of assembly of each building block in the 5' to 3 sequence of each finalized chimeric nucleic acid) in each combination is by design (or non-stochastic) as described above. Because of the non-stochastic nature of this invention, the possibility of unwanted side products is greatly reduced.

In another aspect, the ligation reassembly method is performed systematically. For example, the method is performed in order to generate a systematically compartmentalized library of progeny molecules, with compartments that can be screened systematically, e.g. one by one. In other words this invention provides that, through the selective and judicious use of specific nucleic acid building blocks, coupled with the selective and judicious use of sequentially stepped assembly reactions, a design can be achieved where specific sets of progeny products are made in each of several reaction vessels. This allows a systematic examination and screening procedure to be performed. Thus, these methods allow a potentially very large number of progeny molecules to be examined systematically in smaller groups. Because of its ability to perform chimerizations in a manner that is highly flexible yet exhaustive and systematic as well, particularly when there is a low level of homology among the progenitor molecules, these methods provide for the generation of a library (or set) comprised of a large number of progeny molecules. Because of the non-stochastic nature of the instant ligation reassembly invention, the progeny molecules generated in one aspect comprise a library of finalized chimeric nucleic acid molecules having an overall assembly order that is chosen by design. The saturation mutagenesis and optimized directed evolution methods also can be used to generate different progeny molecular species. It is appreciated that the invention provides freedom of choice and control regarding the selection of demarcation points, the size and number of the nucleic acid building blocks, and the size and design of the couplings. It is appreciated, furthermore, that the requirement for intermolecular homology is highly relaxed for the operability of this invention. In fact, demarcation points can even be chosen in areas of little or no intermolecular homology. For example, because of codon wobble, i.e. the degeneracy of codons, nucleotide substitutions can be introduced into nucleic acid building blocks without altering the amino acid originally encoded in the corresponding progenitor template. Alternatively, a codon can be altered such that the coding for an originally amino acid is altered. This invention provides that such substitutions can be introduced into the nucleic acid building block in order to increase the incidence of intermolecular homologous demarcation points and thus to allow an increased number of couplings to be achieved among the building blocks, which in turn allows a greater number of progeny chimeric molecules to be generated.

In one aspect, the present invention provides a non-stochastic method termed synthetic gene reassembly, that is somewhat related to stochastic shuffling, save that the nucleic acid building blocks are not shuffled or concatenated or chimerized randomly, but rather are assembled non-stochastically.

The synthetic gene reassembly method does not depend on the presence of a high level of homology between polynucleotides to be shuffled. The invention can be used to non-stochastically generate libraries (or sets) of progeny molecules comprised of over $10^{100}$ different chimeras. Conceivably, synthetic gene reassembly can even be used to generate libraries comprised of over $10^{1000}$ different progeny chimeras.

Thus, in one aspect, the invention provides a non-stochastic method of producing a set of finalized chimeric nucleic acid molecules having an overall assembly order that is chosen by design, which method is comprised of the steps of generating by design a plurality of specific nucleic acid building blocks having serviceable mutually compatible ligatable ends and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In a one aspect of the invention, the annealed building pieces are treated with an enzyme, such as a ligase (e.g., T4 DNA ligase) to achieve covalent bonding of the building pieces.

In a another aspect, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, the invention provides for the chimerization of a family of related genes and their encoded family of related products. In a particular exemplification, the encoded products are enzymes. The polypeptides of the present invention can be mutagenized in accordance with the methods described herein.

Thus according to one aspect of the invention, the sequences of a plurality of progenitor nucleic acid templates (e.g., polynucleotides of the invention) are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

Typically a serviceable demarcation point is an area of homology (comprised of at least one homologous nucleotide base) shared by at least two progenitor templates, but the demarcation point can be an area of homology that is shared by at least half of the progenitor templates, at least two thirds of the progenitor templates, at least three fourths of the progenitor templates and in one aspect at almost all of the progenitor templates. Even more in one aspect still a serviceable demarcation point is an area of homology that is shared by all of the progenitor templates.

In a one aspect, the gene reassembly process is performed exhaustively in order to generate an exhaustive library. In other words, all possible ordered combinations of the nucleic acid building blocks are represented in the set of finalized chimeric nucleic acid molecules. At the same time, the assembly order (i.e. the order of assembly of each building block in the 5' to 3 sequence of each finalized chimeric nucleic acid) in each combination is by design (or non-stochastic). Because of the non-stochastic nature of the method, the possibility of unwanted side products is greatly reduced.

In another aspect, the method provides that the gene reassembly process is performed systematically, for example to generate a systematically compartmentalized library, with compartments that can be screened systematically, e.g., one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant gene reassembly invention, the progeny molecules generated in one aspect comprise a library of finalized chimeric nucleic acid molecules having an overall assembly order that is chosen by design. In a particularly aspect, such a generated library is comprised of greater than $10^3$ to greater than $10^{1000}$ different progeny molecular species.

In one aspect, a set of finalized chimeric nucleic acid molecules, produced as described is comprised of a polynucleotide encoding a polypeptide. According to one aspect, this polynucleotide is a gene, which may be a man-made gene. According to another aspect, this polynucleotide is a gene pathway, which may be a man-made gene pathway. The invention provides that one or more man-made genes generated by the invention may be incorporated into a man-made gene pathway, such as pathway operable in a eukaryotic organism (including a plant).

In another exemplification, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g., by mutagenesis) or in an in vivo process (e.g., by utilizing the gene splicing ability of a host organism). It is appreciated that in many instances the introduction of these nucleotides may also be desirable for many other reasons in addition to the potential benefit of creating a serviceable demarcation point.

Thus, according to another aspect, the invention provides that a nucleic acid building block can be used to introduce an intron. Thus, the invention provides that functional introns may be introduced into a man-made gene of the invention. The invention also provides that functional introns may be introduced into a man-made gene pathway of the invention. Accordingly, the invention provides for the generation of a chimeric polynucleotide that is a man-made gene containing one (or more) artificially introduced intron(s).

Accordingly, the invention also provides for the generation of a chimeric polynucleotide that is a man-made gene pathway containing one (or more) artificially introduced intron(s). In one aspect, the artificially introduced intron(s) are functional in one or more host cells for gene splicing much in the way that naturally-occurring introns serve functionally in gene splicing. The invention provides a process of producing man-made intron-containing polynucleotides to be introduced into host organisms for recombination and/or splicing.

A man-made gene produced using the invention can also serve as a substrate for recombination with another nucleic acid. Likewise, a man-made gene pathway produced using the invention can also serve as a substrate for recombination with another nucleic acid. In one aspect, the recombination is facilitated by, or occurs at, areas of homology between the man-made, intron-containing gene and a nucleic acid, which serves as a recombination partner. In one aspect, the recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

The synthetic gene reassembly method of the invention utilizes a plurality of nucleic acid building blocks, each of which in one aspect has two ligatable ends. The two ligatable ends on each nucleic acid building block may be two blunt ends (i.e. each having an overhang of zero nucleotides), or in one aspect one blunt end and one overhang, or more in one aspect still two overhangs.

A useful overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

In one aspect, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large. Exemplary sizes for building block range from 1 base pair (not including any overhangs) to 100,000 base pairs (not including any overhangs). Other exemplary size ranges are also provided, which have lower limits of from 1 bp to 10,000 bp (including every integer value in between) and upper limits of from 2 bp to 100,000 bp (including every integer value in between).

Many methods exist by which a double-stranded nucleic acid building block can be generated that is serviceable for the invention; and these are known in the art and can be readily performed by the skilled artisan.

According to one aspect, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another aspect, the two strands of a double-stranded nucleic acid building block are complementary at fewer than every nucleotide apart from any that form an overhang. Thus, according to this aspect, a double-stranded nucleic acid building block can be used to introduce codon degeneracy. In one aspect the codon degeneracy is introduced using the site-saturation mutagenesis described herein, using one or more N,N,G/T cassettes or alternatively using one or more N,N,N cassettes.

The in vivo recombination method of the invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

In one aspect the invention described herein is directed to the use of repeated cycles of reductive reassortment, recombination and selection which allow for the directed molecular evolution of highly complex linear sequences, such as DNA, RNA or proteins thorough recombination.

Optimized Directed Evolution System

The invention provides a non-stochastic gene modification system termed "optimized directed evolution system" to generate polypeptides, e.g., enzymes or antibodies of the invention, with new or altered properties. Optimized directed evolution is directed to the use of repeated cycles of reductive reassortment, recombination and selection that allow for the directed molecular evolution of nucleic acids through recombination. Optimized directed evolution allows generation of a large population of evolved chimeric sequences, wherein the generated population is significantly enriched for sequences that have a predetermined number of crossover events.

A crossover event is a point in a chimeric sequence where a shift in sequence occurs from one parental variant to another parental variant. Such a point is normally at the juncture of where oligonucleotides from two parents are ligated together to form a single sequence. This method allows calculation of the correct concentrations of oligonucleotide sequences so that the final chimeric population of sequences is enriched for the chosen number of crossover events. This provides more control over choosing chimeric variants having a predetermined number of crossover events.

In addition, this method provides a convenient means for exploring a tremendous amount of the possible protein variant space in comparison to other systems. Previously, if one generated, for example, $10^{13}$ chimeric molecules during a reaction, it would be extremely difficult to test such a high number of chimeric variants for a particular activity. Moreover, a significant portion of the progeny population would have a very high number of crossover events which resulted in proteins that were less likely to have increased levels of a particular activity. By using these methods, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

One method for creating a chimeric progeny polynucleotide sequence is to create oligonucleotides corresponding to fragments or portions of each parental sequence. Each oligonucleotide in one aspect includes a unique region of overlap so that mixing the oligonucleotides together results in a new variant that has each oligonucleotide fragment assembled in the correct order. Additional information can also be found, e.g., in U.S. Ser. No. 09/332,835; U.S. Pat. No. 6,361,974.

The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a ⅓ chance (assuming 3 parents) that an oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. By utilizing these methods, one can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events. These methods are directed to the use of repeated cycles of reductive reassortment, recombination and selection that allow for the directed molecular evolution of a nucleic acid encoding a polypeptide through recombination. This system allows generation of a large population of evolved chimeric sequences, wherein the generated population is significantly enriched for sequences that have a predetermined number of crossover events. A crossover event is a point in a chimeric sequence where a shift in sequence occurs from one parental variant to another parental variant. Such a point is normally at the juncture of where oligonucleotides from two parents are ligated together to form a single sequence. The method allows calculation of the correct concentrations of oligonucleotide sequences so that the final chimeric population of sequences is enriched for the chosen number of crossover events. This provides more control over choosing chimeric variants having a predetermined number of crossover events.

In addition, these methods provide a convenient means for exploring a tremendous amount of the possible protein variant space in comparison to other systems. By using the methods described herein, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

In one aspect, the method creates a chimeric progeny polynucleotide sequence by creating oligonucleotides corresponding to fragments or portions of each parental sequence. Each oligonucleotide in one aspect includes a unique region of overlap so that mixing the oligonucleotides together results in a new variant that has each oligonucleotide fragment assembled in the correct order. See also U.S. Ser. No. 09/332,835.

Determining Crossover Events

Aspects of the invention include a system and software that receive a desired crossover probability density function (PDF), the number of parent genes to be reassembled, and the number of fragments in the reassembly as inputs. The output of this program is a "fragment PDF" that can be used to determine a recipe for producing reassembled genes, and the estimated crossover PDF of those genes. The processing described herein is in one aspect performed in MATLAB™ (The Mathworks, Natick, Mass.) a programming language and development environment for technical computing.

Iterative Processes

In practicing the invention, these processes can be iteratively repeated. For example, a nucleic acid (or, the nucleic acid) responsible for an altered or new phenotype is identified, re-isolated (e.g., using a nucleic acid of the invention), again modified, re-tested for activity. This process can be iteratively repeated until a desired phenotype is engineered. For example, an entire biochemical anabolic or catabolic pathway can be engineered into a cell, including, e.g., new or altered biosynthetic or (e.g., chlorophyll) degradative pathway.

Similarly, if it is determined that a particular oligonucleotide has no affect at all on the desired trait (e.g., a new or altered biosynthetic or (e.g., chlorophyll) degradative pathway phenotype), it can be removed as a variable by synthesizing larger parental oligonucleotides that include the sequence to be removed. Since incorporating the sequence within a larger sequence prevents any crossover events, there will no longer be any variation of this sequence in the progeny polynucleotides. This iterative practice of determining which oligonucleotides are most related to the desired trait, and which are unrelated, allows more efficient exploration all of the possible protein variants that might be provide a particular trait or activity.

In Vivo Shuffling

In vivo shuffling of molecules is use in methods of the invention that provide variants of polypeptides of the invention, e.g., antibodies, enzymes and the like. In vivo shuffling can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In another aspect, the invention includes a method for producing a hybrid polynucleotide from at least a first polynucleotide and a second polynucleotide. The invention can be used to produce a hybrid polynucleotide by introducing at least a first polynucleotide and a second polynucleotide which share at least one region of partial sequence homology (e.g., SEQ ID NOS: 1, 3, 5, 7, 9, 11, 13, 15, 17, 19 and combinations thereof) into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

In vivo reassortment is focused on "inter-molecular" processes collectively referred to as "recombination" which in bacteria, is generally viewed as a "RecA-dependent" phenomenon. The invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process.

Therefore, in another aspect of the invention, novel polynucleotides can be generated by the process of reductive reassortment. The method involves the generation of constructs containing consecutive sequences (original encoding sequences), their insertion into an appropriate vector and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences and results in the production of novel molecular species. Various treatments may be applied to enhance the rate of reassortment. These could include treatment with ultra-violet light, or DNA damaging chemicals and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. In the present invention, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, it is preferable with the present method that the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:
a) Primers that include a poly-A head and poly-T tail which when made single-stranded would provide orientation can be utilized. This is accomplished by having the first few bases of the primers made from RNA and hence easily removed RNaseH.
b) Primers that include unique restriction cleavage sites can be utilized. Multiple sites, a battery of unique sequences and repeated synthesis and ligation steps would be required.
c) The inner few bases of the primer could be thiolated and an exonuclease used to produce properly tailed molecules.

The recovery of the re-assorted sequences relies on the identification of cloning vectors with a reduced repetitive index (RI). The re-assorted encoding sequences can then be recovered by amplification. The products are re-cloned and expressed. The recovery of cloning vectors with reduced RI can be affected by:
1) The use of vectors only stably maintained when the construct is reduced in complexity.
2) The physical recovery of shortened vectors by physical procedures. In this case, the cloning vector would be recovered using standard plasmid isolation procedures and size fractionated on either an agarose gel, or column with a low molecular weight cut off utilizing standard procedures.
3) The recovery of vectors containing interrupted genes which can be selected when insert size decreases.
4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

The following example demonstrates a method of the invention. Encoding nucleic acid sequences (quasi-repeats) derived from three (3) unique species are described. Each sequence encodes a protein with a distinct set of properties. Each of the sequences differs by a single or a few base pairs at a unique position in the sequence. The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI).

Once formed, the constructs may, or may not be size fractionated on an agarose gel according to published protocols, inserted into a cloning vector and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations.

Optionally, the method comprises the additional step of screening the library members of the shuffled pool to identify individual shuffled library members having the ability to bind or otherwise interact, or catalyze a particular reaction (e.g., such as catalytic domain of an enzyme) with a predetermined macromolecule, such as for example a proteinaceous receptor, an oligosaccharide, virion, or other predetermined compound or structure.

The polypeptides that are identified from such libraries can be used for therapeutic, diagnostic, research and related purposes (e.g., catalysts, solutes for increasing osmolarity of an aqueous solution and the like) and/or can be subjected to one or more additional cycles of shuffling and/or selection.

In another aspect, it is envisioned that prior to or during recombination or reassortment, polynucleotides generated by the method of the invention can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N3-Adenine (See Sun and Hurley, (1992); an N-acetylated or deacetylated 4'-fluoro-4-aminobiphenyl adduct capable of inhibiting DNA synthesis (See, for example, van de Poll et al. (1992)); or a N-acetylated or deacetylated 4-aminobiphenyl adduct capable of inhibiting DNA synthesis (See also, van de Poll et al. (1992), pp. 751-758); trivalent chromium, a trivalent chromium salt, a polycyclic aromatic hydrocarbon (PAH) DNA adduct capable of inhibiting DNA replication, such as 7-bromomethyl-benz[a]anthracene ("BMA"), tris(2,3-dibromopropyl)phosphate ("Tris-BP"), 1,2-dibromo-3-chloropropane ("DBCP"), 2-bromoacrolein (2BA), benzo[a]pyrene-7,8-dihydrodiol-9-10-epoxide ("BPDE"), a platinum(II) halogen salt, N-hydroxy-2-amino-3-methylimidazo[4,5-f]quinoline ("N-hydroxy-IQ") and N-hydroxy-2-amino-1-methyl-6-phenylimidazo[4,5-f]-pyridine ("N-hydroxy-PhIP"). Exemplary means for slowing or halting PCR amplification consist of UV light (+)-CC-1065 and (+)-CC-1065-(N3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In another aspect the invention is directed to a method of producing recombinant proteins having biological activity by treating a sample comprising double-stranded template polynucleotides encoding a wild-type protein under conditions according to the invention which provide for the production of hybrid or re-assorted polynucleotides.

Producing Sequence Variants

The invention also provides additional methods for making sequence variants of the nucleic acid sequences of the invention. The invention also provides additional methods for isolating polypeptides of the invention. In one aspect, the invention provides for variants of coding sequences (e.g., a gene, cDNA or message) of the invention, which can be altered by any means, including, e.g., random or stochastic methods, or, non-stochastic, or "directed evolution," methods, as described above.

The isolated variants may be naturally occurring. Variant can also be created in vitro. Variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures. Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. These nucleotide differences can result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described, e.g., in Leung, D. W., et al., Technique, 1:11-15, 1989) and Caldwell, R. C. & Joyce G. F., PCR Methods Applic., 2:28-33, 1992. Briefly, in such procedures, nucleic acids to be mutagenized are mixed with PCR primers, reaction buffer, $MgCl_2$, $MnCl_2$, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM MgCl2, 0.5 mM $MnCl_2$, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids are evaluated.

Variants may also be created using oligonucleotide directed mutagenesis to generate site-specific mutations in any cloned DNA of interest. Oligonucleotide mutagenesis is described, e.g., in Reidhaar-Olson (1988) Science 241:53-57. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, e.g., U.S. Pat. No. 5,965,408.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described, e.g., in Stemmer (1994) Proc. Natl. Acad. Sci. USA 91:10747-10751. Briefly, in such procedures a plurality of nucleic acids to be recombined are digested with DNase to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/μl in a solution of 0.2 mM of each dNTP, 2.2 mM $MgCl_2$, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50-55° C. for 30 seconds, 72° C. for 30 seconds (30-45 times) and 72° C. for 5 minutes. However, it will be appreciated that these parameters may be varied as appropriate. In some aspects, oligonucleotides may be included in the PCR reactions. In other aspects, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some aspects, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described in PCT Publication No. WO 91/16427, published Oct. 31, 1991, entitled "Methods for Phenotype Creation from Multiple Gene Populations".

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in Arkin, A. P. and Youvan, D. C., PNAS, USA, 89:7811-7815, 1992.

In some aspects, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in Delegrave, S. and Youvan, D. C., Biotechnology Research, 11:1548-1552, 1993. Random and site-directed mutagenesis are described in Arnold, F. H., Current Opinion in Biotechnology, 4:450-455, 1993.

In some aspects, the variants are created using shuffling procedures wherein portions of a plurality of nucleic acids which encode distinct polypeptides are fused together to create chimeric nucleic acid sequences which encode chimeric polypeptides as described in U.S. Pat. No. 5,965,408, filed Jul. 9, 1996, entitled, "Method of DNA Reassembly by Interrupting Synthesis" and U.S. Pat. No. 5,939,250, filed May 22, 1996, entitled, "Production of Enzymes Having Desired Activities by Mutagenesis.

The variants of the polypeptides of the invention may be variants in which one or more of the amino acid residues of the polypeptides of the sequences of the invention are substituted with a conserved or non-conserved amino acid residue (in one aspect a conserved amino acid residue) and such substituted amino acid residue may or may not be one encoded by the genetic code.

The invention provides alternative embodiments of the polypeptides of the invention (and the nucleic acids that encode them) comprising at least one conservative amino acid substitution, as discussed herein (e.g., conservative amino acid substitutions are those that substitute a given amino acid in a polypeptide by another amino acid of like characteristics). The invention provides polypeptides (and the nucleic acids that encode them) wherein any, some or all amino acids residues are substituted by another amino acid of like characteristics, e.g., a conservative amino acid substitution.

Conservative substitutions are those that substitute a given amino acid in a polypeptide by another amino acid of like characteristics. Typically seen as conservative substitutions are the following replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue. In alternative aspects, these conservative substitutions can also be synthetic equivalents of these amino acids.

Other variants are those in which one or more of the amino acid residues of a polypeptide of the invention includes a substituent group.

Still other variants are those in which the polypeptide is associated with another compound, such as a compound to increase the half-life of the polypeptide (for example, polyethylene glycol).

Additional variants are those in which additional amino acids are fused to the polypeptide, such as a leader sequence, a secretory sequence, a proprotein sequence or a sequence which facilitates purification, enrichment, or stabilization of the polypeptide.

In some aspects, the fragments, derivatives and analogs retain the same biological function or activity as the polypeptides of the invention. In other aspects, the fragment, derivative, or analog includes a proprotein, such that the fragment, derivative, or analog can be activated by cleavage of the proprotein portion to produce an active polypeptide.

Optimizing Codons to Achieve High Levels of Protein Expression in Host Cells

The invention provides methods for modifying nucleic acids encoding polypeptides involved in chlorophyll catabolism or having an esterase (e.g., chlorophyllase) activity by modifying codon usage. In one aspect, the invention provides methods for modifying codons in a nucleic acid encoding a polypeptide to increase or decrease its expression in a host cell. The invention also provides nucleic acids encoding polypeptides involved in chlorophyll catabolism or having an esterase (e.g., chlorophyllase) activity modified to increase its expression in a host cell, enzymes so modified, and methods of making the modified polypeptides involved in chlorophyll catabolism or having an esterase (e.g., chlorophyllase) activity. The method comprises identifying a "non-preferred" or a "less preferred" codon in enzyme-encoding nucleic acid and replacing one or more of these non-preferred or less preferred codons with a "preferred codon" encoding the same amino acid as the replaced codon and at least one non-preferred or less preferred codon in the nucleic acid has been replaced by a preferred codon encoding the same amino acid. A preferred codon is a codon over-represented in coding sequences in genes in the host cell and a non-preferred or less preferred codon is a codon under-represented in coding sequences in genes in the host cell.

Host cells for expressing the nucleic acids, expression cassettes and vectors of the invention include bacteria, yeast, fungi, plant cells, insect cells and mammalian cells. Thus, the invention provides methods for optimizing codon usage in all of these cells, codon-altered nucleic acids and polypeptides made by the codon-altered nucleic acids. Exemplary host cells include gram negative bacteria, such as *Escherichia coli*; gram positive bacteria, such as *Streptomyces, Lactobacillus gasseri, Lactococcus lactis, Lactococcus cremoris, Bacillus* sp., *Bacillus subtilis, Bacillus cereus*. Exemplary host cells also include eukaryotic organisms, e.g., various yeast, such as *Saccharomyces* sp., including *Saccharomyces cerevisiae, Schizosaccharomyces pombe, Pichia pastoris,* and *Kluyveromyces lactis, Hansenula polymorphs, Aspergillus niger*, and mammalian cells and cell lines and insect cells and cell lines. Thus, the invention also includes nucleic acids and polypeptides optimized for expression in these organisms and species, e.g., the nucleic acids of the invention are codon-optimized for expression in a host cell, e.g., a *Pichia* sp., e.g., *P. pastoris*, a *Saccharomyces* sp., or a *Bacillus* sp., a *Streptomyces* sp., and the like.

For example, the codons of a nucleic acid encoding a polypeptide of the invention or a similar enzyme isolated from a bacterial cell are modified such that the nucleic acid (encoding the enzyme) is optimally expressed in a bacterial cell different from the bacteria from which the enzyme (e.g., a polypeptide of the invention) was derived, a yeast, a fungi, a plant cell, an insect cell or a mammalian cell. Methods for optimizing codons are well known in the art, see, e.g., U.S. Pat. No. 5,795,737; Baca (2000) Int. J. Parasitol. 30:113-118; Hale (1998) Protein Expr. Purif. 12:185-188; Narum (2001) Infect. Immun. 69:7250-7253. See also Narum (2001) Infect. Immun. 69:7250-7253, describing optimizing codons in mouse systems; Outchkourov (2002) Protein Expr. Purif. 24:18-24, describing optimizing codons in yeast; Feng (2000) Biochemistry 39:15399-15409, describing optimizing codons in *E. coli*; Humphreys (2000) Protein Expr. Purif. 20:252-264, describing optimizing codon usage that affects secretion in *E. coli*; Gao (2004) Biotechnol Prog. 20:443-448, describing "UpGene", an application of a web-based DNA codon optimization algorithm.

Transgenic Non-Human Animals

The invention provides transgenic non-human animals comprising a nucleic acid, a polypeptide, an expression cassette or vector or a transfected or transformed cell of the invention. The invention also provides methods of making and using these transgenic non-human animals.

The transgenic non-human animals can be, e.g., goats, rabbits, sheep, pigs, cows, rats and mice, comprising the nucleic acids of the invention. These animals can be used, e.g., as in vivo models to study enzyme activity, or, as models to screen for agents that change the enzyme activity in vivo. The coding sequences for the polypeptides to be expressed in the transgenic non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock (1999) J. Immunol. Methods 231:147-157, describing the production of recombinant proteins in the milk of transgenic dairy animals; Baguisi (1999) Nat. Biotechnol. 17:456-461, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP).

"Knockout animals" can also be used to practice the methods of the invention. For example, in one aspect, the transgenic or modified animals of the invention comprise a "knockout animal," e.g., a "knockout mouse," engineered not to express an endogenous gene, which is replaced with a gene expressing and enzyme of the invention, or, a fusion protein comprising an enzyme of the invention.

Transgenic Plants and Seeds

The invention provides transgenic plants and seeds comprising a nucleic acid, a polypeptide (e.g., a polypeptide involved in chlorophyll catabolism or having an esterase (e.g., chlorophyllase) activity), an expression cassette or vector or a transfected or transformed cell of the invention. The invention also provides plant products, e.g., oils, seeds, leaves, extracts and the like, comprising a nucleic acid and/or a polypeptide of the invention. The transgenic plant can be dicotyledonous (a dicot) or monocotyledonous (a monocot). The invention also provides methods of making and using these transgenic plants and seeds. The transgenic plant or plant cell expressing a polypeptide of the invention may be constructed in accordance with any method known in the art. See, for example, U.S. Pat. No. 6,309,872.

Nucleic acids and expression constructs of the invention can be introduced into a plant cell by any means. For example, nucleic acids or expression constructs can be introduced into the genome of a desired plant host, or, the nucleic acids or expression constructs can be episomes. Introduction into the genome of a desired plant can be such that the host's endogenous transcriptional and/or translational control elements regulate the activity of the introduced nucleic acid, whether it be integrated or episomal. The invention also provides "knockout plants" where insertion of gene sequence by, e.g., homologous recombination, has disrupted the expression of the endogenous gene. Means to generate "knockout" plants are well-known in the art, see, e.g., Strepp (1998) Proc Natl. Acad. Sci. USA 95:4368-4373; Miao (1995) Plant J 7:359-365. See discussion on transgenic plants, below.

The nucleic acids of the invention can be used to confer desired traits on essentially any plant, e.g., on starch-producing plants, such as potato, wheat, rice, barley, and the like. Nucleic acids of the invention can be used to manipulate metabolic pathways of a plant in order to optimize or alter host's expression of a polypeptide of the invention or a homologous enzyme in the host. This can change enzyme (e.g., chlorophyllase) activity or biosynthetic pathway product (a chlorophyll degradative pathway) in the plant. Alternatively, an enzyme or nucleic acid of the invention can be used in production of a transgenic plant to produce a compound not naturally produced by that plant. This can lower production costs or create a novel product.

In one aspect, the first step in production of a transgenic plant involves making an expression construct for expression in a plant cell. These techniques are well known in the art. They can include selecting and cloning a promoter, a coding sequence for facilitating efficient binding of ribosomes to mRNA and selecting the appropriate gene terminator sequences. One exemplary constitutive promoter is CaMV35S, from the cauliflower mosaic virus, which generally results in a high degree of expression in plants. Other promoters are more specific and respond to cues in the plant's internal or external environment. An exemplary light-inducible promoter is the promoter from the cab gene, encoding the major chlorophyll a/b binding protein.

In one aspect, the nucleic acid is modified to achieve greater expression in a plant cell. For example, a sequence of the invention is likely to have a higher percentage of A-T nucleotide pairs compared to that seen in a plant, some of which prefer G-C nucleotide pairs. Therefore, A-T nucleotides in the coding sequence can be substituted with G-C nucleotides without significantly changing the amino acid sequence to enhance production of the gene product in plant cells.

Selectable marker gene can be added to the gene construct in order to identify plant cells or tissues that have successfully integrated the transgene. This may be necessary because achieving incorporation and expression of genes in plant cells is a rare event, occurring in just a few percent of the targeted tissues or cells. Selectable marker genes encode proteins that provide resistance to agents that are normally toxic to plants, such as antibiotics or herbicides. Only plant cells that have integrated the selectable marker gene will survive when grown on a medium containing the appropriate antibiotic or herbicide. As for other inserted genes, marker genes also require promoter and termination sequences for proper function.

In one aspect, making transgenic plants or seeds comprises incorporating sequences of the invention and, optionally, marker genes into a target expression construct (e.g., a plasmid), along with positioning of the promoter and the terminator sequences. This can involve transferring the modified gene into the plant through a suitable method. For example, a construct may be introduced directly into the genomic DNA of the plant cell using techniques such as electroporation and microinjection of plant cell protoplasts, or the constructs can be introduced directly to plant tissue using ballistic methods, such as DNA particle bombardment. For example, see, e.g., Christou (1997) Plant Mol. Biol. 35:197-203; Pawlowski (1996) Mol. Biotechnol. 6:17-30; Klein (1987) Nature 327: 70-73; Takumi (1997) Genes Genet. Syst. 72:63-69, discussing use of particle bombardment to introduce transgenes into wheat; and Adam (1997) supra, for use of particle bombardment to introduce YACs into plant cells. For example, Rinehart (1997) supra, used particle bombardment to generate transgenic cotton plants. Apparatus for accelerating particles is described U.S. Pat. No. 5,015,580; and, the commercially available BioRad (Biolistics) PDS-2000 particle acceleration instrument; see also, John, U.S. Pat. No. 5,608,148; and Ellis, U.S. Pat. No. 5,681,730, describing particle-mediated transformation of gymnosperms.

In one aspect, protoplasts can be immobilized and injected with a nucleic acids, e.g., an expression construct. Although plant regeneration from protoplasts is not easy with cereals, plant regeneration is possible in legumes using somatic embryogenesis from protoplast derived callus. Organized tissues can be transformed with naked DNA using gene gun technique, where DNA is coated on tungsten microprojectiles, shot 1/100th the size of cells, which carry the DNA deep into cells and organelles. Transformed tissue is then induced to regenerate, usually by somatic embryogenesis. This technique has been successful in several cereal species including maize and rice.

Nucleic acids, e.g., expression constructs, can also be introduced in to plant cells using recombinant viruses. Plant cells can be transformed using viral vectors, such as, e.g., tobacco mosaic virus derived vectors (Rouwendal (1997) Plant Mol. Biol. 33:989-999), see Porta (1996) "Use of viral replicons for the expression of genes in plants," Mol. Biotechnol. 5:209-221.

Alternatively, nucleic acids, e.g., an expression construct, can be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, e.g., Horsch (1984) *Science* 233:496-498; Fraley (1983) *Proc. Natl. Acad. Sci. USA* 80:4803 (1983); *Gene Transfer to Plants*, Potrykus, ed. (Springer-Verlag, Berlin 1995). The DNA in an *A. tumefaciens* cell is contained in the bacterial chromosome as well as in another structure known as a Ti (tumor-inducing) plasmid. The Ti plasmid contains a stretch of DNA termed T-DNA (~20 kb long) that is transferred to the plant cell in the infection process and a series of vir (virulence) genes that direct the infection process. *A. tumefaciens* can only infect a plant through wounds: when a plant root or stem is wounded it gives off certain chemical signals, in response to which, the vir genes of *A. tumefaciens* become activated and direct a series of events necessary for the transfer of the T-DNA from the Ti plasmid to the plant's chromosome. The T-DNA then enters the plant cell through the wound. One speculation is that the T-DNA waits until the plant DNA is being replicated or transcribed, then inserts itself into the exposed plant DNA. In order to use *A. tumefaciens* as a transgene vector, the tumor-inducing section of T-DNA have to be removed, while retaining the T-DNA border regions and the vir genes. The transgene is then inserted between the T-DNA border regions, where it is transferred to the plant cell and becomes integrated into the plant's chromosomes.

The invention provides for the transformation of monocotyledonous plants using the nucleic acids of the invention, including important cereals, see Hiei (1997) Plant Mol. Biol. 35:205-218. See also, e.g., Horsch, Science (1984) 233:496; Fraley (1983) Proc. Natl. Acad. Sci USA 80:4803; Thykjaer (1997) supra; Park (1996) Plant Mol. Biol. 32:1135-1148, discussing T-DNA integration into genomic DNA. See also D'Halluin, U.S. Pat. No. 5,712,135, describing a process for the stable integration of a DNA comprising a gene that is functional in a cell of a cereal, or other monocotyledonous plant.

In one aspect, the third step can involve selection and regeneration of whole plants capable of transmitting the incorporated target gene to the next generation. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee (1987) Ann. Rev. of Plant Phys. 38:467-486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

After the expression cassette is stably incorporated in transgenic plants, it can be introduced into other plants by sexual crossing. Any of a number of standard breeding techniques can be used, depending upon the species to be crossed. Since transgenic expression of the nucleic acids of the invention leads to phenotypic changes, plants comprising the recombinant nucleic acids of the invention can be sexually crossed with a second plant to obtain a final product. Thus, the seed of the invention can be derived from a cross between two transgenic plants of the invention, or a cross between a plant of the invention and another plant. The desired effects (e.g., expression of the polypeptides of the invention to produce a plant in which flowering or seeding behavior is altered) can be enhanced when both parental plants express the polypeptides of the invention. The desired effects can be passed to future plant generations by standard propagation means.

The nucleic acids and polypeptides of the invention are expressed in or inserted in any plant or seed. Transgenic plants of the invention can be dicotyledonous or monocotyledonous. Examples of monocot transgenic plants of the invention are grasses, such as meadow grass (blue grass, *Poa*), forage grass such as *festuca, lolium*, temperate grass, such as *Agrostis*, and cereals, e.g., wheat, oats, rye, barley, rice, sorghum, and maize (corn). Examples of dicot transgenic plants of the invention are tobacco, legumes, such as lupins, potato, sugar beet, pea, bean and soybean, and cruciferous plants (family Brassicaceae), such as cauliflower, rape seed, and the closely related model organism *Arabidopsis thaliana*. Thus, the transgenic plants and seeds of the invention include a broad range of plants, including, but not limited to, species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna*, and *Zea*.

In alternative embodiments, the nucleic acids of the invention are expressed in plants which contain fiber cells, including, e.g., cotton, silk cotton tree (Kapok, *Ceiba pentandra*), desert willow, creosote bush, winterfat, balsa, ramie, kenaf, hemp, roselle, jute, sisal abaca and flax. In alternative embodiments, the transgenic plants of the invention can be members of the genus *Gossypium*, including members of any *Gossypium* species, such as *G. arboreum; G. herbaceum, G. barbadense*, and *G. hirsutum*.

The invention also provides for transgenic plants to be used for producing large amounts of the polypeptides (e.g., enzymes or antibody) of the invention. For example, see Palmgren (1997) Trends Genet. 13:348; Chong (1997) Transgenic Res. 6:289-296 (producing human milk protein beta-casein in transgenic potato plants using an auxin-inducible, bidirectional mannopine synthase (mas1',2') promoter with *Agrobacterium tumefaciens*-mediated leaf disc transformation methods).

Using known procedures, one of skill can screen for plants of the invention by detecting the increase or decrease of transgene mRNA or protein in transgenic plants. Means for detecting and quantitation of mRNAs or proteins are well known in the art.

Polypeptides and Peptides

In one aspect, the invention provides isolated, synthetic or recombinant polypeptides having a sequence identity (e.g., at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or more, or complete (100%) sequence identity) to an exemplary sequence of the invention, e.g., proteins having a sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 or SEQ ID NO:20.

In one aspect, a polypeptide of the invention has an esterase activity, such as a chlorophyllase (a chlase) activity, or, has an enzyme activity comprising enzymatic modification of a chlorophyll molecule, e.g., wherein the enzymatic modification comprises catabolism of the chlorophyll molecule. In one aspect, the esterase activity comprises a chlorophyll chlorophyllido-hydrolyase activity.

Another aspect of the invention provides an isolated, synthetic or recombinant polypeptide or peptide including at least 10, 15, 20, 25, 30, 35, 40, 45, 50, 55, 60, 65, 70, 75, 80, 85, 90, 95 or 100 or more consecutive bases of a polypeptide or peptide sequence of the invention, sequences substantially identical thereto, and the sequences complementary thereto. The peptide can be, e.g., an immunogenic fragment, a motif (e.g., a binding site), a signal sequence, a prepro sequence or a catalytic domains (CDs) or active site.

The invention also provides chimeric polypeptides (and the nucleic acids encoding them) comprising at least two enzymes of the invention or subsequences thereof, e.g., active sites, or catalytic domains (CDs). A chimeric protein of the invention (e.g., a fusion protein, or, other heterodimer, e.g., two domains joined by other means, e.g., a linker, or, electrostatically) can comprise one polypeptide (e.g., active site or catalytic domain peptide) of the invention and another polypeptide (e.g., active site or catalytic domain peptide) of the invention or other polypeptide. For example, a chimeric protein of the invention can have any activity of a polypeptide involved chlorophyll catabolism or having an esterase (e.g., chlorophyllase) activity, e.g., as described herein. In one aspect the chimeric protein of the invention comprises a fusion of domains, e.g., a single domain can exhibit one or any combination of activities.

The polypeptides of the invention include enzymes in an active or inactive form. For example, the polypeptides of the invention include proproteins before "maturation" or processing of prepro sequences, e.g., by a proprotein-processing enzyme, such as a proprotein convertase to generate an "active" mature protein. The polypeptides of the invention include enzymes inactive for other reasons, e.g., before "activation" by a post-translational processing event, e.g., an endo- or exo-peptidase or proteinase action, a phosphorylation event, an amidation, a glycosylation or a sulfation, a dimerization event, and the like. The polypeptides of the invention include all active forms, including active subsequences, e.g., catalytic domains or active sites, of the enzymes.

Methods for identifying "prepro" domain sequences and signal sequences are well known in the art, see, e.g., Van de Ven (1993) Crit. Rev. Oncog. 4(2):115-136. For example, to identify a prepro sequence, the protein is purified from the extracellular space and the N-terminal protein sequence is determined and compared to the unprocessed form.

The invention includes polypeptides with or without a signal sequence and/or a prepro sequence. The invention includes polypeptides with heterologous signal sequences and/or prepro sequences. The prepro sequence (including a sequence of the invention used as a heterologous prepro domain) can be located on the amino terminal or the carboxy terminal end of the protein. The invention also includes isolated or recombinant signal sequences, prepro sequences and catalytic domains (e.g., "active sites") comprising sequences of the invention.

The percent sequence identity can be over the full length of the polypeptide, or, the identity can be over a region of at least about 50, 60, 70, 80, 90, 100, 150, 200, 250, 300, 350, 400, 450, 500, 550, 600, 650, 700 or more residues. Polypeptides of the invention can also be shorter than the full length of exemplary polypeptides. In alternative aspects, the invention provides polypeptides (peptides, fragments) ranging in size between about 5 and the full length of a polypeptide, e.g., an enzyme, of the invention; exemplary sizes being of about 5, 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, or more residues, e.g., contiguous residues of an exemplary enzymes of the invention.

Peptides of the invention (e.g., a subsequence of an exemplary polypeptide of the invention) can be useful as, e.g., labeling probes, antigens, toleragens, motifs, enzyme active sites (e.g., "catalytic domains" of enzymes of the invention), binding sites of enzymes of the invention, signal sequences and/or prepro domains.

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer) in accordance with the instructions provided by the manufacturer.

The peptides and polypeptides of the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

The peptides and polypeptides of the invention, as defined above, include all "mimetic" and "peptidomimetic" forms. The terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered from an exemplary polypeptide of the invention. In one aspect, a mimetic composition is used in a composition, cell system or process of the invention (e.g., a host cell having a plasmid expressing at least one enzyme of the invention).

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

A polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thienylalanine; D- or L-1, -2,3-, or 4-pyrenylalanine; D- or L-3 thienylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N=C=N—R') such as, e.g., 1-cyclohexyl-3(2-morpholinyl-(4-ethyl)carbodiimide or 1-ethyl-3(4-azonia-4, 4-dimetholpentyl)carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, in one aspect under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzene-sulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The invention also provides methods for modifying the polypeptides of the invention by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent crosslinks, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides of the invention, either by direct synthesis or by synthesis of a series of fragments that can be coupled using other known techniques.

The invention includes polypeptides of the invention with and without signal. The polypeptide comprising a signal sequence of the invention can be a polypeptide of the invention or another polypeptide.

The invention includes immobilized polypeptides of the invention, including enzymes, antibodies and fragments thereof. The invention provides methods for inhibiting polypeptide activity, e.g., using dominant negative mutants or antibodies of the invention. The invention includes heterocomplexes, e.g., fusion proteins, heterodimers, etc., comprising the enzymes of the invention.

Polypeptides of the invention can have enzyme activity under various conditions, e.g., extremes in pH and/or temperature, oxidizing agents, and the like. The invention provides methods leading to alternative enzyme preparations with different catalytic efficiencies and stabilities, e.g., towards temperature, oxidizing agents and changing wash conditions. In one aspect, enzyme variants can be produced using techniques of site-directed mutagenesis and/or random mutagenesis. In one aspect, directed evolution can be used to produce a great variety of enzyme variants with alternative specificities and stability.

The proteins of the invention are also useful as research reagents to identify enzyme modulators, e.g., activators or inhibitors of enzyme activity. Briefly, test samples (compounds, broths, extracts, and the like) are added to enzyme assays to determine their ability to inhibit substrate cleavage Inhibitors identified in this way can be used in industry and research to reduce or prevent undesired proteolysis. Enzyme inhibitors can be combined to increase the spectrum of activity.

The invention also provides methods of discovering a new enzymes having similar activity to an enzyme of the invention using the nucleic acids, polypeptides and antibodies of the invention. In one aspect, phagemid libraries are screened for expression-based discovery of a new enzyme. In another aspect, lambda phage libraries are screened for expression-based discovery of a new enzyme. Screening of the phage or phagemid libraries can allow the detection of toxic clones; improved access to substrate; reduced need for engineering a host, by-passing the potential for any bias resulting from mass excision of the library; and, faster growth at low clone densities. Screening of phage or phagemid libraries can be in liquid phase or in solid phase. In one aspect, the invention provides screening in liquid phase. This gives a greater flexibility in assay conditions; additional substrate flexibility; higher sensitivity for weak clones; and ease of automation over solid phase screening.

The invention provides screening methods using the proteins and nucleic acids of the invention and robotic automation to enable the execution of many thousands of biocatalytic reactions and screening assays in a short period of time, e.g., per day, as well as ensuring a high level of accuracy and reproducibility (see discussion of arrays, below). As a result, a library of derivative compounds can be produced in a matter of weeks. For further teachings on modification of molecules, including small molecules, see PCT/US94/09174.

Another aspect of the invention is an isolated or purified polypeptide comprising the sequence of one of the invention, or fragments comprising at least about 5, 10, 15, 20, 25, 30, 35, 40, 50, 75, 100, or 150 consecutive amino acids thereof. As discussed above, such polypeptides may be obtained by inserting a nucleic acid encoding the polypeptide into a vector such that the coding sequence is operably linked to a sequence capable of driving the expression of the encoded polypeptide in a suitable host cell. For example, the expression vector may comprise a promoter, a ribosome binding site for translation initiation and a transcription terminator. The vector may also include appropriate sequences for amplifying expression.

Another aspect of the invention is polypeptides or fragments thereof which have at least about 50%, at least about 55%, at least about 60%, at least about 65%, at least about 70%, at least about 75%, at least about 80%, at least about 85%, at least about 90%, at least about 95%, or more than about 95% sequence identity (homology) to one of the polypeptides of the invention, or a fragment comprising at least 5, 10, 15, 20, 25, 30, 35, 40, 50, 75, 100, or 150 or more consecutive amino acids thereof. Sequence identity (homology) may be determined using any of the programs described above which aligns the polypeptides or fragments being compared and determines the extent of amino acid identity or similarity between them. It will be appreciated that amino acid equivalence, or identity, or "homology," includes conservative amino acid substitutions such as those described above.

The polypeptides or fragments having homology to one of the polypeptides of the invention, or a fragment comprising at least about 5, 10, 15, 20, 25, 30, 35, 40, 50, 75, 100, or 150 consecutive amino acids thereof may be obtained by isolating the nucleic acids encoding them using the techniques described above.

Alternatively, the homologous polypeptides or fragments may be obtained through biochemical enrichment or purification procedures. The sequence of potentially homologous polypeptides or fragments may be determined by activity assays, gel electrophoresis and/or microsequencing. The sequence of the prospective homologous polypeptide or fragment can be compared to one of the polypeptides of the invention, or a fragment comprising at least about 5, 10, 15, 20, 25, 30, 35, 40, 50, 75, 100, or 150 consecutive amino acids thereof using any of the programs described above.

Another aspect of the invention is an assay for identifying fragments or variants of the invention, which retain the enzymatic function of the polypeptides of the invention. For example the fragments or variants of polypeptides of the invention may be used to catalyze biochemical reactions, which indicate that the fragment or variant retains the enzymatic activity of a polypeptide of the invention.

The assay for determining if fragments of variants retain the enzymatic activity of the polypeptides of the invention includes the steps of: contacting the polypeptide fragment or variant with a substrate molecule under conditions which allow the polypeptide fragment or variant to function and detecting either a decrease in the level of substrate or an increase in the level of the specific reaction product of the reaction between the polypeptide and substrate.

The polypeptides of the invention or fragments comprising at least 5, 10, 15, 20, 25, 30, 35, 40, 50, 75, 100, or 150 consecutive amino acids thereof may be used in a variety of applications. For example, the polypeptides or fragments thereof may be used to catalyze biochemical reactions. In accordance with one aspect of the invention, there is provided a process for utilizing the polypeptides of the invention or polynucleotides encoding such polypeptides for hydrolyzing ester linkages. In such procedures, a substance containing an ester linkage (e.g., a chlorophyll) is contacted with one of the polypeptides of the invention, or sequences substantially identical thereto under conditions which facilitate the hydrolysis of the ester linkage.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds, such as small molecules. Each biocatalyst is specific for one functional group, or several related functional groups and can react with many starting compounds containing this functional group.

The biocatalytic reactions produce a population of derivatives from a single starting compound. These derivatives can be subjected to another round of biocatalytic reactions to produce a second population of derivative compounds. Thousands of variations of the original small molecule or compound can be produced with each iteration of biocatalytic derivatization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

Many of the procedural steps are performed using robotic automation enabling the execution of many thousands of biocatalytic reactions and screening assays per day as well as ensuring a high level of accuracy and reproducibility. As a result, a library of derivative compounds can be produced in a matter of weeks which would take years to produce using current chemical methods.

In a particular aspect, the invention provides a method for modifying small molecules, comprising contacting a polypeptide encoded by a polynucleotide described herein or enzymatically active fragments thereof with a small molecule to produce a modified small molecule. A library of modified small molecules is tested to determine if a modified small molecule is present within the library which exhibits a desired activity. A specific biocatalytic reaction which produces the modified small molecule of desired activity is identified by systematically eliminating each of the biocatalytic reactions used to produce a portion of the library and then testing the small molecules produced in the portion of the library for the presence or absence of the modified small molecule with the desired activity. The specific biocatalytic reactions which produce the modified small molecule of desired activity is optionally repeated. The biocatalytic reactions are conducted with a group of biocatalysts that react with distinct structural moieties found within the structure of a small molecule, each biocatalyst is specific for one structural moiety or a group of related structural moieties; and each biocatalyst reacts with many different small molecules which contain the distinct structural moiety.

Signal Sequences, Prepro, Binding Domains and Catalytic Domains

The invention provides enzyme signal sequences (e.g., signal peptides (SPs)), prepro domains, binding domains and catalytic domains (CDs) (e.g., active sites). The SPs, prepro domains and/or CDs of the invention can be isolated or recombinant peptides or can be part of a fusion protein, e.g., as a heterologous domain in a chimeric protein. The invention provides nucleic acids encoding these catalytic domains (CDs), prepro domains and signal sequences (SPs, e.g., a peptide having a sequence comprising/consisting of amino terminal residues of a polypeptide of the invention). In one aspect, the invention provides a signal sequence comprising a peptide comprising/consisting of a sequence as set forth in residues 1 to 10, 1 to 11, 1 to 12, 1 to 13, 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 39, 1 to 40, 1 to 41, 1 to 42, 1 to 43, 1 to 44, 1 to 45, 1 to 46, 1 to 47, 1 to 48, 1 to 49, 1 to 50, 1 to 51, or 1 to 52 or more, of a polypeptide of the invention.

In one aspect, the invention also provides chimeric polypeptides (and the nucleic acids encoding them) comprising at least two enzymes of the invention or subsequences thereof, e.g., catalytic domains (CDs) or active sites. For example, a chimeric protein of the invention can have any combination of activities. In one aspect the chimeric protein of the invention comprises a fusion of domains, e.g., a single domain can exhibit one or any combination of activities (e.g., as a recombinant chimeric protein).

The invention also provides isolated, synthetic or recombinant signal sequences comprising/consisting of a signal sequence of the invention, e.g., exemplary signal sequences as set forth in Table 1, below, and polypeptides comprising these signal sequences. The polypeptide can be another enzyme of the invention, or another type of enzyme or polypeptide. For example, to aid in reading Table 1, the invention provides an isolated, synthetic or recombinant signal sequence as set forth by the amino terminal amino acid residues 1 to 21 ("NH$_2$-MSRVCLPLTLTLALTLSARA") of SEQ ID NO: 2, encoded, e.g., by SEQ ID NO:1, etc.:

TABLE 1

| SEQ ID NO: | Signal sequence position (AA = Amino Acid) | Signal sequence |
|---|---|---|
| 1, 2<br>11, 12<br>13, 14<br>15, 16 | AA1-20 | MSRVCLPLTLTLALTLSARA |
| 17, 18<br>19, 20<br>3, 4 | AA1-25 | MKKYKTGLVLSGGGTRGFAHLGVIA |
| 5, 6 | AA1-25 | MRRIVFLYILALLCVSCANRNPSVS |
| 7, 8 | AA1-51 | MTRKKIGLALSGGAARGFAHLGVLKVF<br>AEHGIPVDFVAGTSAGSFAGAAFA |
| 9, 10 | AA1-23 | MFNKALPAAAAVAGLFLSTSAMA |

The signal sequences (SPs) and/or prepro sequences of the invention can be isolated peptides, or, sequences joined to another enzyme of the invention, or a heterologous protein, e.g., as a fusion (chimeric) protein. In one aspect, the invention provides polypeptides comprising signal sequences of the invention. In one aspect, polypeptides comprising signal sequences SPs and/or prepro of the invention comprise sequences heterologous to enzymes of the invention (e.g., a fusion protein comprising an SP and/or prepro of the invention and/or sequences from another protein). In one aspect, the invention provides an enzyme of the invention with heterologous SPs and/or prepro sequences, e.g., sequences with a yeast signal sequence. Enzymes of the invention can comprise a heterologous SP and/or prepro in a vector, e.g., a pPIC series vector (Invitrogen, Carlsbad, Calif.). In one aspect, SPs and/or prepro sequences of the invention are identified following identification of novel polypeptides. The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence. This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. More than 100 signal sequences for proteins in this group have been determined. The signal sequences can vary in length from 13 to 36 amino acid residues. Various methods of recognition of signal sequences are known to those of skill in the art. For example, in one aspect, novel signal peptides are identified by a method referred to as SignalP. SignalP uses a combined neural network which recognizes both signal peptides and their cleavage sites. (Nielsen, et al., "Identification of prokaryotic and eukaryotic signal peptides and prediction of their cleavage sites." Protein Engineering, vol. 10, no. 1, p. 1-6 (1997).

It should be understood that in some aspects an enzyme of the invention may not have SPs and/or prepro sequences, or one or more "domains." In one aspect, the invention provides an enzyme of the invention lacking all or part of an SP and/or a prepro domain. In one aspect, the invention provides a nucleic acid sequence encoding a signal sequence (SP) and/or prepro from one enzyme of the invention operably linked to a nucleic acid sequence of a different enzyme of the invention or, optionally, a signal sequence (SPs) and/or prepro domain from a different type of protein may be desired.

The invention also provides isolated or recombinant polypeptides comprising signal sequences (SPs), prepro domain and/or catalytic domains (CDs) of the invention and heterologous sequences. The heterologous sequences are sequences not naturally associated (e.g., to enzymes of the invention) with an SP, prepro domain and/or CD. The sequence to which the SP, prepro domain and/or CD are not naturally associated can be on the SP's, prepro domain and/or CD's amino terminal end, carboxy terminal end, and/or on both ends of the SP and/or CD. In one aspect, the invention provides an isolated or recombinant polypeptide comprising (or consisting of) a polypeptide comprising a signal sequence (SP), prepro domain and/or catalytic domain (CD) of the invention with the proviso that it is not associated with any sequence to which it is naturally associated. Similarly in one aspect, the invention provides isolated or recombinant nucleic acids encoding these polypeptides. Thus, in one aspect, the isolated or recombinant nucleic acid of the invention comprises coding sequence for a signal sequence (SP), prepro domain and/or catalytic domain (CD) of the invention and a heterologous sequence (i.e., a sequence not naturally associated with the a signal sequence (SP), prepro domain and/or catalytic domain (CD) of the invention). The heterologous sequence can be on the 3' terminal end, 5' terminal end, and/or on both ends of the SP, prepro domain and/or CD coding sequence.

Hybrid (Chimeric) Enzymes and Peptide Libraries

In one aspect, the invention provides hybrid enzymes of the invention and fusion proteins, including peptide libraries, comprising sequences of the invention. The peptide libraries of the invention can be used to isolate peptide modulators (e.g., activators or inhibitors) of targets, such as enzyme of the invention, their substrates, etc. The peptide libraries of the invention can be used to identify formal binding partners of targets, such as ligands, e.g., cytokines, hormones and the like. In one aspect, the invention provides chimeric proteins comprising a signal sequence (SP), prepro domain and/or catalytic domain (CD) of the invention or a combination thereof and a heterologous sequence (see above).

In one aspect, the fusion proteins of the invention (e.g., the peptide moiety) are conformationally stabilized (relative to linear peptides) to allow a higher binding affinity for targets. The invention provides fusions of enzymes of the invention and other peptides, including known and random peptides. They can be fused in such a manner that the structure of a polypeptide is not significantly perturbed and the peptide is metabolically or structurally conformationally stabilized. This allows the creation of a peptide library that is easily monitored both for its presence within cells and its quantity.

Amino acid sequence variants of the invention can be characterized by a predetermined nature of the variation, a feature that sets them apart from a naturally occurring form, e.g., an allelic or interspecies variation of enzymes of the invention. In one aspect, the variants of the invention exhibit the same qualitative biological activity as the naturally occurring analogue. Alternatively, the variants can be selected for having modified characteristics. In one aspect, while the site or region for introducing an amino acid sequence variation is predetermined, the mutation per se need not be predetermined. For example, in order to optimize the performance of a mutation at a given site, random mutagenesis may be conducted at the target codon or region and the expressed enzyme variants screened for the optimal combination of desired activity. Techniques for making substitution mutations at predetermined sites in DNA having a known sequence are well known, as discussed herein for example, M13 primer mutagenesis and PCR mutagenesis. Screening of the mutants can be done using, e.g., assays of chlorophyll hydrolysis, as described in Example 1, below. In alternative aspects, amino acid substitutions can be single residues; insertions can be on the order of from about 1 to 20 amino acids, although considerably larger insertions can be done. Deletions can range from about 1 to about 20, 30, 40, 50, 60, 70 residues or more. To obtain a final derivative with the optimal properties, substitutions, deletions, insertions or any combination thereof may be used. Generally, these changes are done on a few amino acids to minimize the alteration of the molecule. However, larger changes may be tolerated in certain circumstances.

The invention provides polypeptides, e.g., enzymes, of the invention where the structure of the polypeptide backbone, the secondary or the tertiary structure, e.g., an alpha-helical or beta-sheet structure, has been modified. In one aspect, the charge or hydrophobicity has been modified. In one aspect, the bulk of a side chain has been modified. Substantial changes in function or immunological identity are made by selecting substitutions that are less conservative. For example, substitutions can be made which more significantly affect: the structure of the polypeptide backbone in the area of the alteration, for example a alpha-helical or a beta-sheet structure; a charge or a hydrophobic site of the molecule, which can be at an active site; or a side chain. The invention provides substitutions in polypeptide of the invention where (a) a hydrophilic residues, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine. The variants can exhibit the same qualitative biological activity as enzymes of the invention, although variants can be selected to modify the characteristics of the enzyme as needed.

"Amino acid" or "amino acid sequence" as used herein refer to an oligopeptide, peptide, polypeptide, or protein sequence, or to a fragment, portion, or subunit of any of these and to naturally occurring or synthetic molecules.

"Amino acid" or "amino acid sequence" include an oligopeptide, peptide, polypeptide, or protein sequence, or to a fragment, portion, or subunit of any of these, and to naturally occurring or synthetic molecules. The term "polypeptide" as used herein, refers to amino acids joined to each other by peptide bonds or modified peptide bonds, i.e., peptide isosteres and may contain modified amino acids other than the 20 gene-encoded amino acids. The polypeptides may be modified by either natural processes, such as post-translational processing, or by chemical modification techniques which are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, glucan hydrolase processing, phosphorylation, prenylation, racemization, selenoylation, sulfation and transfer-RNA mediated addition of amino acids to protein such as arginylation. (See Creighton, T. E., *Proteins—Structure and Molecular Properties 2nd Ed.*, W.H. Freeman and Company, New York (1993); *Posttranslational Covalent Modification of Proteins*, B. C. Johnson, Ed., Academic Press, New York, pp. 1-12 (1983)). The peptides and polypeptides of the invention also include all "mimetic" and "peptidomimetic" forms, as described in further detail, below.

Additionally a "substantially identical" amino acid sequence is a sequence that differs from a reference sequence by one or more conservative or non-conservative amino acid substitutions, deletions, or insertions, particularly when such a substitution occurs at a site that is not the active site (catalytic domains (CDs)) of the molecule and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from a polypeptide, resulting in modification of the structure of the polypeptide, without significantly altering its biological activity. For example, amino- or carboxyl-terminal amino acids that are not required for enzyme biological activity can be removed. Modified polypeptide sequences of the invention can be assayed for biological (e.g., enzymatic, or binding) activity by any number of methods, including contacting the modified polypeptide sequence with an enzyme substrate and determining whether the modified polypeptide decreases the amount of specific substrate in the assay or increases the bioproducts of the enzymatic reaction of a functional polypeptide with the substrate.

"Fragments" as used herein are a portion of a naturally occurring protein which can exist in at least two different conformations. Fragments can have the same or substantially the same amino acid sequence as the naturally occurring protein. "Substantially the same" means that an amino acid sequence is largely, but not entirely, the same, but retains at least one functional activity of the sequence to which it is related. In alternative aspects, two amino acid sequences are "substantially the same" or "substantially homologous" if they have at least about 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity. Fragments which have different three dimensional structures as the naturally occurring protein are also included; e.g., a "pro-form" molecule, such as a low activity proprotein that can be modified by cleavage to produce a mature enzyme with significantly higher activity.

In one aspect, enzymes of the invention comprise epitopes or purification tags, signal sequences or other fusion sequences, etc. In one aspect, enzymes can be fused to a random peptide to form a fusion polypeptide. By "fused" or "operably linked" herein is meant that the random peptide and the enzyme are linked together, in such a manner as to minimize the disruption to the stability of the enzyme structure, e.g., it retains activity. The fusion polypeptide (or fusion polynucleotide encoding the fusion polypeptide) can comprise further components as well, including multiple peptides at multiple loops.

In one aspect, the peptides and nucleic acids encoding them are randomized, either fully randomized or they are biased in their randomization, e.g. in nucleotide/residue frequency generally or per position. "Randomized" means that each nucleic acid and peptide consists of essentially random nucleotides and amino acids, respectively. In one aspect, the nucleic acids which give rise to the peptides can be chemically synthesized, and thus may incorporate any nucleotide at any position. Thus, when the nucleic acids are expressed to form peptides, any amino acid residue may be incorporated at any position. The synthetic process can be designed to generate randomized nucleic acids, to allow the formation of all or most of the possible combinations over the length of the nucleic acid, thus forming a library of randomized nucleic acids. The library can provide a sufficiently structurally diverse population of randomized expression products to affect a probabilistically sufficient range of cellular responses to provide one or more cells exhibiting a desired response.

Thus, the invention provides an interaction library large enough so that at least one of its members will have a structure that gives it affinity for some molecule, protein, or other factor.

The invention provides a means for generating chimeric polypeptides which may encode biologically active hybrid polypeptides (e.g., hybrid enzymes of the invention). In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular enzyme from different microorganisms. An enzyme encoded by a first polynucleotide from one organism or variant may, for example, function effectively under a particular environmental condition, e.g. high salinity. An enzyme encoded by a second polynucleotide from a different organism or variant may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

A hybrid polypeptide resulting from the method of the invention may exhibit specialized enzyme activity not displayed in the original enzymes. For example, following recombination and/or reductive reassortment of polynucleotides encoding enzyme activities, the resulting hybrid polypeptide encoded by a hybrid polynucleotide can be screened for specialized enzyme activities obtained from each of the original enzymes, i.e. the type of bond on which the enzyme acts and the temperature at which the enzyme functions. Thus, for example, the enzyme may be screened to ascertain those chemical functionalities which distinguish the hybrid enzyme from the original enzymes, such as substrate specificity, or temperature, pH or salt concentration at which the hybrid polypeptide functions.

Sources of the original polynucleotides may be isolated from individual organisms ("isolates"), collections of organisms that have been grown in defined media ("enrichment cultures"), or, uncultivated organisms ("environmental samples"). The use of a culture-independent approach to derive polynucleotides encoding novel bioactivities from environmental samples is most preferable since it allows one to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions which promote recombination and/or reductive reassortment creating potentially active biomolecules with novel or enhanced activities.

The microorganisms from which the polynucleotide may be prepared include prokaryotic microorganisms, such as Eubacteria and Archaebacteria and lower eukaryotic microorganisms such as fungi, some algae and protozoa. Polynucleotides may be isolated from environmental samples in which case the nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles. Polynucleotides encoding enzymes isolated from extremophilic microorganisms can be used. Such enzymes may function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. For example, several esterases and lipases cloned and expressed from extremophilic organisms show high activity throughout a wide range of temperatures and pHs.

Polynucleotides selected and isolated as hereinabove described are introduced into a suitable host cell. A suitable host cell is any cell which is capable of promoting recombination and/or reductive reassortment. The selected polynucleotides are in one aspect already in a vector which includes appropriate control sequences. The host cell can be a higher eukaryotic cell, such as a mammalian cell, or a lower eukaryotic cell, such as a yeast cell, or in one aspect, the host cell can be a prokaryotic cell, such as a bacterial cell. Introduction of the construct into the host cell can be effected by calcium phosphate transfection, DEAE-Dextran mediated transfection, or electroporation (Davis et al., 1986).

As representative examples of appropriate hosts, there may be mentioned: bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; and plant cells. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described in "SV40-transformed simian cells support the replication of early SV40 mutants" (Gluzman, 1981) and other cell lines capable of expressing a compatible vector, for example, the C127, 3T3, CHO, HeLa and BHK cell lines. Mammalian expression vectors will comprise an origin of replication, a suitable promoter and enhancer and also any necessary ribosome binding sites, polyadenylation site, splice donor and acceptor sites, transcriptional termination sequences and 5' flanking nontranscribed sequences. DNA sequences derived from the SV40 splice and polyadenylation sites may be used to provide the required nontranscribed genetic elements.

In another aspect, it is envisioned the method of the present invention can be used to generate novel polynucleotides encoding biochemical pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. Thus, a gene cluster is a group of adjacent genes that are either identical or related, usually as to their function. An example of a biochemical pathway encoded by gene clusters are polyketides.

Gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of *E. coli*. This f-factor of *E. coli* is a plasmid which affects high-frequency transfer of itself during conjugation and is ideal to achieve and stably propagate large DNA fragments, such as gene clusters from mixed microbial samples. One aspect is to use cloning vectors, referred to as "fosmids" or bacterial artificial chromosome (BAC) vectors. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library." Another type of vector for use in the present invention is a cosmid vector. Cosmid vectors were originally designed to clone and propagate large segments of genomic DNA. Cloning into cosmid vectors is described in detail in Sambrook et al., *Molecular Cloning: A Laboratory Manual, 2nd Ed.*, Cold Spring Harbor Laboratory Press (1989). Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Therefore, in a one aspect, the invention relates to a method for producing a biologically active hybrid polypeptide and screening such a polypeptide for enhanced activity by:
  1) introducing at least a first polynucleotide in operable linkage and a second polynucleotide in operable linkage, the at least first polynucleotide and second polynucleotide sharing at least one region of partial sequence homology, into a suitable host cell;
  2) growing the host cell under conditions which promote sequence reorganization resulting in a hybrid polynucleotide in operable linkage;
  3) expressing a hybrid polypeptide encoded by the hybrid polynucleotide;
  4) screening the hybrid polypeptide under conditions which promote identification of enhanced biological activity; and
  5) isolating the a polynucleotide encoding the hybrid polypeptide.

Methods for screening for various enzyme activities are known to those of skill in the art and are discussed throughout the present specification. Such methods may be employed when isolating the polypeptides and polynucleotides of the invention.

Screening Methodologies and "On-Line" Monitoring Devices

In practicing the methods of the invention, a variety of apparatus and methodologies can be used to in conjunction with the polypeptides and nucleic acids of the invention, e.g., to screen polypeptides for enzyme activity, to screen compounds as potential modulators, e.g., activators or inhibitors of activity, for antibodies that bind to a polypeptide of the invention, for nucleic acids that hybridize to a nucleic acid of the invention, to screen for cells expressing a polypeptide of the invention and the like. In addition to the array formats described in detail below for screening samples, alternative formats can also be used to practice the methods of the invention. Such formats include, for example, mass spectrometers, chromatographs, e.g., high-throughput HPLC and other forms of liquid chromatography, and smaller formats, such as 1536-well plates, 384-well plates and so on. High throughput screening apparatus can be adapted and used to practice the methods of the invention, see, e.g., U.S. Patent Application No. 20020001809.

Capillary Arrays

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. Capillary arrays, such as the GIGAMATRIX™, Diversa Corporation, San Diego, Calif.; and arrays described in, e.g., U.S. Patent Application No. 20020080350 A1; WO 0231203 A; WO 0244336 A, provide an alternative apparatus for holding and screening samples. In one aspect, the capillary array includes a plurality of capillaries formed into an array of adjacent capillaries, wherein each capillary comprises at least one wall defining a lumen for retaining a sample. The lumen may be cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. Additionally, the capillary array can include interstitial material disposed between adjacent capillaries in the array, thereby forming a solid planar device containing a plurality of through-holes.

A capillary array can be formed of any number of individual capillaries, for example, a range from 100 to 4,000,000 capillaries. Further, a capillary array having about 100,000 or more individual capillaries can be formed into the standard size and shape of a Microtiter® plate for fitment into standard laboratory equipment. The lumens are filled manually or automatically using either capillary action or microinjection using a thin needle. Samples of interest may subsequently be removed from individual capillaries for further analysis or characterization. For example, a thin, needle-like probe is positioned in fluid communication with a selected capillary to either add or withdraw material from the lumen.

In a single-pot screening assay, the assay components are mixed yielding a solution of interest, prior to insertion into the capillary array. The lumen is filled by capillary action when at least a portion of the array is immersed into a solution of interest. Chemical or biological reactions and/or activity in each capillary are monitored for detectable events. A detectable event is often referred to as a "hit", which can usually be distinguished from "non-hit" producing capillaries by optical detection. Thus, capillary arrays allow for massively parallel detection of "hits".

In a multi-pot screening assay, a polypeptide or nucleic acid, e.g., a ligand, can be introduced into a first component, which is introduced into at least a portion of a capillary of a capillary array. An air bubble can then be introduced into the capillary behind the first component. A second component can then be introduced into the capillary, wherein the second component is separated from the first component by the air bubble. The first and second components can then be mixed by applying hydrostatic pressure to both sides of the capillary array to collapse the bubble. The capillary array is then monitored for a detectable event resulting from reaction or non-reaction of the two components.

In a binding screening assay, a sample of interest can be introduced as a first liquid labeled with a detectable particle into a capillary of a capillary array, wherein the lumen of the capillary is coated with a binding material for binding the detectable particle to the lumen. The first liquid may then be removed from the capillary tube, wherein the bound detectable particle is maintained within the capillary, and a second liquid may be introduced into the capillary tube. The capillary is then monitored for a detectable event resulting from reaction or non-reaction of the particle with the second liquid.

Arrays, or "Biochips"

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of a gene, e.g., a gene of the invention (a nucleic acid encoding a polypeptide of the invention). One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays" can also be used to simultaneously quantify a plurality of proteins. The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

In practicing the methods of the invention, any known array and/or method of making and using arrays can be incorporated in whole or in part, or variations thereof, as described, for example, in U.S. Pat. Nos. 6,277,628; 6,277,489; 6,261, 776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999)

Nature Genetics Supp. 21:25-32. See also published U.S. patent applications Nos. 20010018642; 20010019827; 20010016322; 20010014449; 20010014448; 20010012537; 20010008765.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface, as discussed in further detail, below.

Antibodies and Antibody-Based Screening Methods

The invention provides isolated or recombinant antibodies that specifically bind to a polypeptide of the invention. These antibodies can be used to isolate, identify or quantify a polypeptide of the invention or related polypeptides. These antibodies can be used to isolate other polypeptides within the scope the invention or other related polypeptides. The antibodies can be designed to bind to an active site of a polypeptide of the invention. Thus, the invention provides methods of inhibiting enzymes using the antibodies of the invention (see discussion above). The invention provides fragments of the enzymes of the invention, including immunogenic fragments of a polypeptide of the invention. The invention provides compositions comprising a polypeptide or peptide of the invention and adjuvants or carriers and the like.

The antibodies can be used in immunoprecipitation, staining, immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention. Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu Rev. Biophys. Biomol. Struct. 26:27-45.

The polypeptides of the invention or fragments comprising at least about 5, 10, 15, 20, 25, 30, 35, 40, 50, 75, 100, or 150 or more consecutive amino acids thereof, may also be used to generate antibodies which bind specifically to the polypeptides or fragments. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention, or fragments comprising at least about 5, 10, 15, 20, 25, 30, 35, 40, 50, 75, 100, or 150 or more consecutive amino acids thereof.

In immunoaffinity procedures, the antibody is attached to a solid support, such as a bead or other column matrix. The protein preparation is placed in contact with the antibody under conditions in which the antibody specifically binds to one of the polypeptides of the invention, or fragment thereof. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays and Western Blots.

Polyclonal antibodies generated against the polypeptides of the invention, or fragments comprising at least about 5, 10, 15, 20, 25, 30, 35, 40, 50, 75, 100, or 150 or more consecutive amino acids thereof can be obtained by direct injection of the polypeptides into an animal or by administering the polypeptides to an animal, for example, a nonhuman. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique (Kohler and Milstein, Nature, 256:495-497, 1975), the trioma technique, the human B-cell hybridoma technique (Kozbor et al., Immunology Today 4:72, 1983) and the EBV-hybridoma technique (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be adapted to produce single chain antibodies to the polypeptides of the invention, or fragments comprising at least about 5, 10, 15, 20, 25, 30, 35, 40, 50, 75, 100, or 150 consecutive amino acids thereof. Alternatively, transgenic mice may be used to express humanized antibodies to these polypeptides or fragments thereof.

Antibodies generated against the polypeptides of the invention, or fragments comprising at least about 5, 10, 15, 20, 25, 30, 35, 40, 50, 75, 100, or 150 or more consecutive amino acids thereof may be used in screening for similar polypeptides from other organisms and samples. In such techniques, polypeptides from the organism are contacted with the antibody and those polypeptides which specifically bind the antibody are detected. Any of the procedures described above may be used to detect antibody binding. One such screening assay is described in "Methods for Measuring Cellulase Activities", *Methods in Enzymology*, Vol 160, pp. 87-116.

The term "antibody" includes a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Kits

The invention provides kits comprising the compositions, e.g., nucleic acids, expression cassettes, vectors, cells, transgenic seeds or plants or plant parts, polypeptides (e.g., enzymes involved in chlorophyll catabolism or having an esterase (e.g., chlorophyllase) activity) and/or antibodies of the invention. The kits also can contain instructional material teaching the methodologies and industrial uses of the invention, as described herein. In one aspect, the kits are designed to accommodate industrial scale levels of processing, e.g., of foods, feeds, oils and the like.

Whole Cell Engineering and Measuring Metabolic Parameters

The methods of the invention provide whole cell evolution, or whole cell engineering, of a cell to develop a new cell strain having a new phenotype, e.g., a modified chlorophyll catabolism pathway, or, a new or modified enzyme (e.g., chlorophyllase) activity, by modifying the genetic composition of the cell. The genetic composition can be modified by addition to the cell of a nucleic acid of the invention, e.g., a coding sequence for an enzyme of the invention. See, e.g., WO0229032; WO0196551.

To detect the new phenotype, at least one metabolic parameter of a modified cell is monitored in the cell in a "real time" or "on-line" time frame. In one aspect, a plurality of cells, such as a cell culture, is monitored in "real time" or "on-line." In one aspect, a plurality of metabolic parameters is monitored in "real time" or "on-line." Metabolic parameters can be monitored using an enzyme of the invention.

Metabolic flux analysis (MFA) is based on a known biochemistry framework. A linearly independent metabolic matrix is constructed based on the law of mass conservation and on the pseudo-steady state hypothesis (PSSH) on the intracellular metabolites. In practicing the methods of the invention, metabolic networks are established, including the:
  identity of all pathway substrates, products and intermediary metabolites
  identity of all the chemical reactions interconverting the pathway metabolites, the stoichiometry of the pathway reactions,
  identity of all the enzymes catalyzing the reactions, the enzyme reaction kinetics,
  the regulatory interactions between pathway components, e.g. allosteric interactions, enzyme-enzyme interactions etc,
  intracellular compartmentalization of enzymes or any other supramolecular organization of the enzymes, and,
  the presence of any concentration gradients of metabolites, enzymes or effector molecules or diffusion barriers to their movement.

Once the metabolic network for a given strain is built, mathematic presentation by matrix notion can be introduced to estimate the intracellular metabolic fluxes if the on-line metabolome data is available. Metabolic phenotype relies on the changes of the whole metabolic network within a cell. Metabolic phenotype relies on the change of pathway utilization with respect to environmental conditions, genetic regulation, developmental state and the genotype, etc. In one aspect of the methods of the invention, after the on-line MFA calculation, the dynamic behavior of the cells, their phenotype and other properties are analyzed by investigating the pathway utilization. For example, if the glucose supply is increased and the oxygen decreased during the yeast fermentation, the utilization of respiratory pathways will be reduced and/or stopped, and the utilization of the fermentative pathways will dominate. Control of physiological state of cell cultures will become possible after the pathway analysis. The methods of the invention can help determine how to manipulate the fermentation by determining how to change the substrate supply, temperature, use of inducers, etc. to control the physiological state of cells to move along desirable direction. In practicing the methods of the invention, the MFA results can also be compared with transcriptome and proteome data to design experiments and protocols for metabolic engineering or gene shuffling, etc.

In practicing the methods of the invention, any modified or new phenotype can be conferred and detected, including new or improved characteristics in the cell. Any aspect of metabolism or growth can be monitored.

Monitoring Expression of an mRNA Transcript

In one aspect of the invention, the engineered phenotype comprises increasing or decreasing the expression of an mRNA transcript (e.g., a message for a polypeptide involved in chlorophyll catabolism or having an esterase (e.g., chlorophyllase) activity) or generating new transcripts in a cell. This increased or decreased expression can be traced by testing for the presence of an enzyme of the invention or by enzyme activity assays. mRNA transcripts, or messages, also can be detected and quantified by any method known in the art, including, e.g., Northern blots, quantitative amplification reactions, hybridization to arrays, and the like. Quantitative amplification reactions include, e.g., quantitative PCR, including, e.g., quantitative reverse transcription polymerase chain reaction, or RT-PCR; quantitative real time RT-PCR, or "real-time kinetic RT-PCR" (see, e.g., Kreuzer (2001) Br. J. Haematol. 114:313-318; Xia (2001) Transplantation 72:907-914).

In one aspect of the invention, the engineered phenotype is generated by knocking out expression of a homologous gene. The gene's coding sequence or one or more transcriptional control elements can be knocked out, e.g., promoters or enhancers. Thus, the expression of a transcript can be completely ablated or only decreased.

In one aspect of the invention, the engineered phenotype comprises increasing the expression of a homologous gene. This can be effected by knocking out of a negative control element, including a transcriptional regulatory element acting in cis- or trans-, or, mutagenizing a positive control element. One or more, or, all the transcripts of a cell can be measured by hybridization of a sample comprising transcripts of the cell, or, nucleic acids representative of or complementary to transcripts of a cell, by hybridization to immobilized nucleic acids on an array.

Monitoring Expression of a Polypeptides, Peptides and Amino Acids

In one aspect of the invention, the engineered phenotype comprises increasing or decreasing the expression of a polypeptide (e.g., a polypeptide involved in chlorophyll catabolism or having an esterase (e.g., chlorophyllase) activity) or generating new polypeptides in a cell. This increased or decreased expression can be traced by determining the amount of enzyme present or by activity assays. Polypeptides, peptides and amino acids also can be detected and quantified by any method known in the art, including, e.g., nuclear magnetic resonance (NMR), spectrophotometry, radiography (protein radiolabeling), electrophoresis, capillary electrophoresis, high performance liquid chromatography (HPLC), thin layer chromatography (TLC), hyperdiffusion chromatography, various immunological methods, e.g. immunoprecipitation, immunodiffusion, immuno-electrophoresis, radioimmunoassays (RIAs), enzyme-linked immunosorbent assays (ELISAs), immuno-fluorescent assays, gel electrophoresis (e.g., SDS-PAGE), staining with antibodies, fluorescent activated cell sorter (FACS), pyrolysis mass spectrometry, Fourier-Transform Infrared Spectrometry, Raman spectrometry, GC-MS, and LC-Electrospray and cap-LC-tandem-electrospray mass spectrometries, and the like. Novel bioactivities can also be screened using methods, or variations thereof, described in U.S. Pat. No. 6,057,103. Furthermore, as discussed below in detail, one or more, or, all the polypeptides of a cell can be measured using a protein array.

Enzymes

The invention provides novel compositions and methods for enzymatically treating, e.g., decoloring or "bleaching," algal, animal (e.g., fish) and/or plant preparations, feeds, foods or oils comprising chlorophyll (the chlorophyll can be in the preparations, feeds, foods or oils naturally, as a contaminant, as an undesired composition in a processed product, etc). In one aspect, chlorophyll-containing or chlorophyll-contaminated compositions, e.g., algal, animal or plant preparations, feeds, foods or oils are enzymatically treated using a chlorophyllase or equivalent enzyme. Any polypeptide having an activity that can modify a chlorophyll or chlorophyll metabolite, can be used in a composition or method of the invention.

Chlorophyllases

The polypeptides and/or peptides of the invention can have esterase activity, e.g., a chlorophyllase or a similar activity. The polypeptides and/or peptides of the invention can include catalytic antibodies, enzymes, active sites, and the like. These polypeptides and/or peptides of the invention having esterase (e.g., chlorophyllase) activity can be used in compositions or methods of the invention. For example, in one aspect, compositions and methods of the invention enzymatically treat chlorophyll-containing or chlorophyll-contaminated compositions by hydrolyzing chlorophyll (FIG. 1A) to phytol (FIG. 1B) and chlorophyllide (FIG. 1C).

Any chlorophyllase, chlase or chlorophyll chlorophyllidohydrolyase or polypeptide having a similar activity (e.g., chlorophyll-chlorophyllido hydrolase 1 or chlase 1, or, chlorophyll-chlorophyllido hydrolase 2 or chlase 2, see, e.g., NCBI P59677_1 and P59678, respectively) can be used in a composition or method of the invention. Any polypeptide (e.g., enzyme or catalytic antibody) that catalyses the hydrolysis of a chlorophyll ester bond to yield chlorophyllide and phytol can be used in a composition or method of the invention. Any isolated, recombinant or synthetic or chimeric (a combination of synthetic and recombinant) polypeptide (e.g., enzyme or catalytic antibody) can be used, e.g., a chlorophyllase, chlase or chlorophyll chlorophyllido-hydrolyase or polypeptide having a similar activity can be used in a composition or method of the invention, see, e.g., Marchler-Bauer (2003) Nucleic Acids Res. 31: 383-387.

In one aspect, the compositions and methods of the invention can be practiced with enzymes as described in WO 0229022. For example, in one aspect, the compositions and methods of the invention can comprise recombinant expression of enzymes, e.g., chlorophyllases, such as chlorophyllase-encoding polynucleotides. In one aspect, recombinant nucleic acid is expressed in whole cells, cell extracts or in vitro. In one aspect, the enzyme-encoding polynucleotide is modified to result in production of altered levels of enzyme (e.g., chlorophyllase) in a transformed host cell.

In one aspect, the compositions and methods of the invention can be practiced with known enzymes, such as chlorophyllases (including chlases and chlorophyll chlorophyllido-hydrolyases) and related polypeptides are well known in the art. For example, the *Arabidopsis thaliana* chlorophyllase can be used as described, e.g., in NCBI entry NM_123753 (where the enzyme having a sequence as set forth in SEQ ID NO:22 is encoded, e.g., by SEQ ID NO:21):

```
                                                          SEQ ID NO: 21
AAAAAAAGTAAAGAAAAGAAAAACTAATAAAGAACAAAAAAAATGTCCTCTTCTTCATCAAGAAACGCC

TTTGAAGATGGCAAATACAAATCAAATCTCTTAACCTTGGACTCATCATCTCGTTGCTGCAAAATAACA

CCGTCTTCTAGAGCTTCACCGTCTCCGCCAAAGCAGCTGTTGGTGGCTACGCCGGTGGAGGAAGGAGAT

TATCCGGTGGTGATGCTCCTCCATGGTTACCTTCTCTACAACTCCTTCTATTCTCAGCTTATGTTGCAT

GTCTCTTCTCATGGCTTCATCCTCATCGCTCCTCAGTTATATAGTATCGCCGGACCAGACACAATGGAT

GAGATTAAATCAACGGCGGAGATTATGGATTGGTTATCAGTAGGACTTAATCACTTTCTTCCAGCGCAA

GTAACACCAAACCTATCCAAATTTGCCCTCTCCGGCCATAGCCGCGGTGGCAAAACCGCGTTTGCGGTC

GCCTTAAAGAAATTTGGGTACTCCTCGAATCTAAAGATCTCGACATTGATCGGTATAGATCCAGTCGAT

GGAACAGGGAAAGGGAAACAAACCCCTCCTCCGGTGTTGGCTTACCTTCCAAACTCATTTGACCTAGAC

AAAACGCCTATACTTGTGATCGGTTCGGGGCTTGGTGAAACCGCTCGGAACCCATTATTCCCACCGTGT

GCACCTCCCGGAGTGAATCACCGAGAGTTCTTTCGGGAATGTCAAGGTCCAGCATGGCATTTCGTTGCG

AAGGATTATGGGCATTTGGACATGCTTGATGATGATACAAAAGGGATTAGAGGGAAGAGTTCTTATTGT

TTGTGTAAGAATGGTGAAGAGAGGAGACCAATGAGGAGATTCGTTGGTGGACTTGTTGTATCATTTTTG

AAGGCTTATTTGGAAGGAGATGATCGTGAATTAGTTAAGATCAAAGATGGGTGTCACGAGGATGTTCCC

GTTGAAATTCAAGAGTTTGAGGTTATCATGTAAACATAAGTTTTTCTTTAGGGGCTGGTTTTTCTATTG

TCAATATCATCAGCTTTTGTTGCTTATGGTTTTACAAACTTATATTGTACAACTCTTTAAGTCACCTCT

TTGCTTATGATATTAACCCGATC
```

```
                                                       SEQ ID NO: 22
MSSSSSRNAFEDGKYKSNLLTLDSSSRCCKITPSSRASPSPPKQLLVATPVEEGDYPVVMLLHGYLLYN

SFYSQLMLHVSSHGFILIAPQLYSIAGPDTMDEIKSTAEIMDWLSVGLNHFLPAQVTPNLSKFALSGHS

RGGKTAFAVALKKFGYSSNLKISTLIGIDPVDGTGKGKQTPPPVLAYLPNSFDLDKTPILVIGSGLGET

ARNPLFPPCAPPGVNHREFFRECQGPAWHFVAKDYGHLDMLDDDTKGIRGKSSYCLCKNGEERRPMRRF

VGGLVVSFLKAYLEGDDRELVKIKDGCHEDVPVEIQEFEVIM
```

The *Ginkgo biloba* chlorophyllase can be used as described, e.g., in NCBI entry AY292526:

```
                                                       SEQ ID NO: 23
TTGAAAAACAAAAACGAAGAAGATGAACTCAGTACTTGCACACAGCCATCGGCCATGGTTTTAGTGAAG

GATGTGTTCAGCGAAGGTCCTTTACCTGTTCAAATCCTCGCAATTCCACAAGCCAACTCATCTCCATGC

TCAAAATTAGCAGACAAAAACGGAACTGCAACCACGCCTTCTCCTTGTCGGCCTCCTAAACCCCTGCTG

ATCGCTCTTCCTTCCCAACATGGAGATTATCCTCTCATCCTCTTTTTCCACGGCTATGTACTCCTCAAT

TCCTTCTATTCTCAACTCTTGCGCCATGTTGCTTCCCATGGATACATCGCCATAGCTCCTCAGATGTAC

AGTGTAATTGGCCCAAATACGACTCCAGAAATAGCCGATGCAGCGGCCATTACAGACTGGTTACGAGAT

GGACTCTCGGATAATCTTCCGCAAGCTTTAAACAATCATGTGAGGCCCAATTTTGAGAAATTTGTGCTA

GCGGGGCACTCGCGCGGGGGTAAAGTGGCATTTGCACTTGCCCTAGGTCGAGTCTCGCAGCCATCTTTA

AAGTACTCGGCCCTTGTAGGTCTTGATCCAGTCGATGGAATGGGAAAAGATCAACAAACCAGTCATCCT

ATTCTGTCATACAGAGAGCATTCCTTTGATTTGGGTATGCCAACATTAGTGGTAGGTTCGGGCCTGGGT

CCGTGCAAAGAAACCCTCTCTTCCCTCCCTGTGCTCCCCAAGGTGTTAACCACCATGATTTCTTCTAC

GAATGTGTCGCTCCTGCCTATCATTTTGTTGCCTCTGATTATGGGCATCTTGATTTCTTAGACGACGAC

ACCAAAGGAATAAGAGGAAAGGCTACTTATTGCCTCTGTAAGAATGGGGAAGCAAGAGAGCCAATGCGG

AAGTTTAGCGGTGGAATTGTGGTTGCATTTCTTCAAGCATTTCTTGGTGATAATCGTGGAGCCCTGAAT

GATATTATGGTTTATCCTTCACATGCTCCAGTCAAGATTGAGCCTCCAGAGTCTTTGGTTACAGAAGAT

GTAAAATCCCCAGAAGTCGAATTATTACGCCGGGCAGTTTGCAGATGATGTACCATGGTATTATGCATT

AAAGGAATGTATTTGTTATTAAAAAAATATTAAGAAGTAAAAAAAAAAAAAA
                                                       SEQ ID NO: 24
MVLVKDVFSEGPLPVQILAIPQANSSPCSKLADKNGTATTPSPCRPPKPLLIALPSQHGDYPLILFFHG

YVLLNSFYSQLLRHVASHGYIAIAPQMYSVIGPNTTPEIADAAAITDWLRDGLSDNLPQALNNHVRPNF

EKFVLAGHSRGGKVAFALALGRVSQPSLKYSALVGLDPVDGMGKDQQTSHPILSYREHSFDLGMPTLVV

GSGLGPCKRNPLFPPCAPQGVNHHDFFYECVAPAYHFVASDYGHLDFLDDDTKGIRGKATYCLCKNGEA

REPMRKFSGGIVVAFLQAFLGDNRGALNDIMVYPSHAPVKIEPPESLVTEDVKSPEVELLRRAVCR
```

The *Brassica oleracea* chlorophyllase can be used as described, e.g., in NCBI entry AF337546:

```
                                                       SEQ ID NO: 25
ACACAAAAAATATATAACACAAAGAAATAGAAGAAGGAAAAAATGTCCCCCTCCTTTCTTTTCTTTAC

TTTGTTTTTGATAAAGGAAATGTCCTCTTCATCATCAGCAAACTCCTTTGAGGACGGCAAATACAAAAC

AGATCTTTTAACAGTAGGCTTATCATCTTGCTGCTGGAAAAAGCCCTCCTCTTCTCCGACTCCGCAGTC

TCCGCCGAAGAGGCTTTTGGTGGCAACGCCGGTGGAGGAAGGAGAATATCCGGTGGTGATGCTCCTCCA

TGGTTACCTTCTCTACAACTCATTTTATTCCCAGCTTATGTTGCATGTCTCTTCCCATGGCTTCATTGT

CATCGCTCCGCAGTTATATAGCATTGCCGGACCAGACACCATGGATGAGATAAAATCAACGGCAGAGAT
```

-continued
```
TATTGATTGGTTATCGGTCGGACTAAACCACTTTCTTCCACCACAAGTAACACCAAACCTATCCAAGTT

CGCACTCTCCGGCCATAGCCGTGGTGGGAAGACCGCATTTGCCTTGGCCTTAAAGAAATTTGGATACTC

GTCCGACCTAAAGATCTCGGCATTGATAGGTATAGATGTTGGAACTGTTTTTTGGACAAATGGCTATGG

CCAATATTCCGGTGAATTTTTCGAGCAATTTGATTGTCGAAATGACCGGATTGTGGAATCGTAGGATTC

ATTGTTATGAGCACTATGGTATAGTGTAATCATATATCAAAAACGAAGTTCGTTTGAATGAGAAATGAA

AGTCTAAAATAGATTATTTGTAAAATATCTATATTAGAATTATGAGGTAAGAAACCTCTTGTGTTTAAA

ATGGAGAAGTTATAACAAAGTTATAAAAAACTTTGTAAACAATTTGGTGTGTTAGC
```

SEQ ID NO: 26
```
MSPSFLFFTLFLIKEMSSSSSANSFEDGKYKTDLLTVGLSSCCWKKPSSSPTPQSPPKRLLVATPVEEG

EYPVVMLLHGYLLYNSFYSQLMLHVSSHGFIVIAPQLYSIAGPDTMDEIKSTAEIIDWLSVGLNHFLPP

QVTPNLSKFALSGHSRGGKTAFALALKKFGYSSDLKISALIGIDVGTVFWTNGYGQYSGEFFEQFDCRN

DRIVES
```

The *Citrus sinensis* chlorophyllase can be used as described, e.g., in NCBI entry Q9MV14:

SEQ ID NO: 27
```
MAAMVDAKPAASVQGTPLLATATLPVFTRGIYSTKRITLETSSPSSPPPPKPLIIVTPAGKGTFNVILF

LHGTSLSNKSYSKIFDHIASHGFIVVAPQLYTSIPPPSATNELNSAAEVAEWLPQGLQQNLPENTEANV

SLVAVMGHSRGGQTAFALSLRYGFGAVIGLDPVAGTSKTTGLDPSILSFDSFDFSIPVTVIGTGLGGVA

RCITACAPEGANHEEFFNRCKNSSRAHFVATDYGHMDILDDNPSDVKSWALSKYFCKNGNESRDPMRRC

VSGIVVAFLKDFFYGDAEDFRQILKDPSFAPIKLDSVEYIDASSMLTTTHVKV
```

Enzyme Preparations

Enzymes used in the methods of the invention can be formulated or modified, e.g., chemically modified, e.g., to enhance oil solubility, stability, activity or for immobilization. For example, enzymes used in the methods of the invention can be formulated to be amphipathic or more lipophilic. For example, enzymes used in the methods of the invention can be encapsulated, e.g., in liposomes or gels, e.g., alginate hydrogels or alginate beads or equivalents. Enzymes used in the methods of the invention can be formulated in micellar systems, e.g., a ternary micellar (TMS) or reverse micellar system (RMS) medium. Enzymes used in the methods of the invention can be formulated as described in Yi (2002) J. of Molecular Catalysis B: Enzymatic, Vol. 19, No. 0, pgs 319-325. For example, amphipathic enzyme, e.g., chlorophyllase, in the form of a ternary micellar (TMS) or reverse micellar system (RMS) medium can be encapsulated in alginate hydrogels. In one aspect, an enzyme, e.g., a chlorophyllase, is prepared in aqueous buffer and retained in a hydrogel, e.g., TMS/alginate and RMS/alginate. One approach to encapsulating enzyme, e.g., chlorophyllase, can be emulsification and/or internal gelation of the enzyme-TMS or -RMS system.

The enzymatic reactions of the methods of the invention can be done in vitro, including, e.g. capillary arrays, as discussed below, or, in whole cell systems. In one aspect, enzyme reactions of the methods of the invention are done in one reaction vessel or multiple vessels. In one aspect, the enzymatic reactions of the methods of the invention are done in a vegetable oil refining apparatus.

The compositions and methods of the invention can be practiced with immobilized enzymes, e.g., immobilized chlorophyllase. The enzyme can be immobilized on any organic or inorganic support. Exemplary inorganic supports include alumina, celite, Dowex-1-chloride, glass beads and silica gel. Exemplary organic supports include alginate hydrogels or alginate beads or equivalents.

In various aspects of the invention, immobilization of chlorophyllase can be optimized by physical adsorption on various inorganic supports, including alumina, celite, Dowex-1-chloride, glass beads and silica gel. Enzymes used to practice the invention can be immobilized in different media, including water, Tris-HCl buffer solution and a ternary micellar system containing Tris-HCl buffer solution, hexane and surfactant. The highest immobilization efficiency (84.56%) and specific activity (0.34 mmol hydrolyzed chlorophyll mg protein-1 per min) were obtained when chlorophyllase was suspended in Tris-HCl buffer solution and adsorbed onto silica gel.

Industrial and Medical Applications

The polypeptides, e.g., enzymes of the invention involved in chlorophyll catabolism or having an esterase (e.g., chlorophyllase) activity, can be used in a variety of medical and industrial applications, as described herein. The compositions and methods of the invention can be used in conjunction with any industrial use or pharmaceutical or medical application for the treatment of chlorophyll-containing materials, e.g., vegetable preparations, oil-comprising materials. For example, the compositions and methods of the invention can be used with processes for converting a non-hydratable phospholipid to a hydratable form, oil degumming, processing of oils from plants, fish, algae and the like, to name just a few applications. For example, the methods of the invention can be used with the processing of fats and oils as described, e.g., in JP Patent Application Publication H6-306386, describing converting phospholipids present in the oils and fats into water-soluble substances containing phosphoric acid groups.

The compositions and methods of the invention can be used in conjunction with methods for processing plant oils, such as those derived from or isolated from rice bran, soy, canola, palm, cottonseed, corn, palm kernel, coconut, peanut, sesame, sunflower. The compositions and methods of the invention can be used in conjunction with methods for processing essential oils, e.g., those from fruit seed oils, e.g., grapeseed, apricot, borage, etc. The compositions and methods of the invention can be used in conjunction with methods for processing oils and phospholipids in different forms, including crude forms, degummed, gums, wash water, clay, silica, soapstock, and the like. The compositions and methods of the invention can be used in conjunction with methods for processing high phosphorous oils (e.g., a soy bean oil), fish oils, animal oils, plant oils, algae oils and the like.

The compositions and methods of the invention can be used in conjunction with methods for processing and making edible oils, biodiesel oils, liposomes for pharmaceuticals and cosmetics, structured phospholipids and structured lipids. The compositions and methods of the invention can be used in conjunction with methods for oil extraction. The compositions and methods of the invention can be used in conjunction with methods for making various soaps.

The methods can further comprise modifying pH (e.g., increasing pH) to promote aqueous separation of chlorophyllide. Thus, the compositions and methods of the invention can also comprise a caustic neutralization processes, e.g., with caustic-neutralized pH conditions. In one aspect, the compositions and methods of the invention comprise a neutralization step, e.g., in treating "chemically refined oils", e.g., using chlorophyllases and/or in the separation chlorophyllide. The compositions and methods of the invention can comprise modifying pH to promote aqueous separation of chlorophyllide.

In one aspect, the compositions and methods of the invention comprise use of adsorbent-free or reduced adsorbent silica refining devices and processes, which are known in the art, e.g., using TriSyl Silica Refining Processes (Grace Davison, Columbia, Md.), or, SORBSIL R™ silicas (INEOS Silicas, Joliet, Ill.).

Enzymatic Treatment, or "Bleaching" or Decoloring Processes

The invention provides novel compositions and methods for enzymatically treating, e.g., decoloring or "bleaching," algal, animal (e.g., fish) and/or plant preparations, feeds, foods or oils, as illustrated in FIGS. 8 to 16. In one aspect, chlorophyll-containing or chlorophyll-contaminated foods or oils are treated. For example, in alternative aspects, vegetable oils, including oils processed from oilseeds, such as canola (rapeseed) oil or soybean oil, or oil fruits, such as palm oil, are processes using the compositions and/or methods of the invention.

At least one step in this exemplary method involves use of an enzyme, e.g., a chlorophyllase enzyme that can hydrolyze chlorophyll to phytol and chlorophyllide. In alternative aspects, one, several or all steps use an enzyme. The reaction can be in vitro or in vivo.

Figure 8:
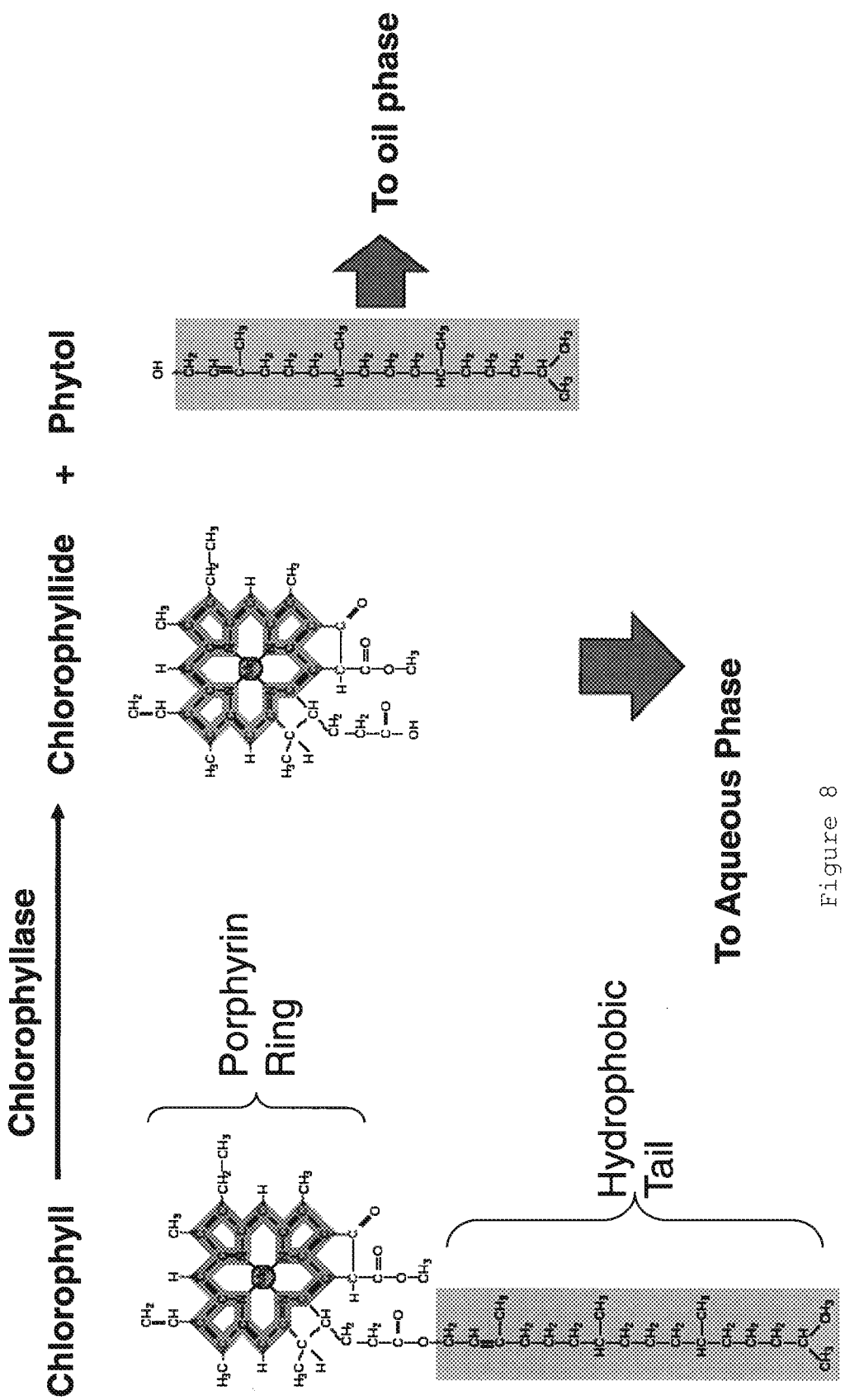
FIG. 8 illustrates the reaction of an exemplary esterase of the invention in chlorophyll degradation, as described in detail, below.

FIG. 8 illustrates the reaction of an exemplary esterase of the invention in chlorophyll degradation—the chlorophyllase (chlase) catalyzes hydrolysis of an ester bond in chlorophyll to yield chlorophyllide and phytol, where the chlorophyllide enters the aqueous phase due to a hydrophilic porphyrin ring, and the phytol separates into an oil (hydrophobic) phase. In one aspect of a process of the invention the hydrophilic porphyrin ring is separated with gum/water fraction using any one of the many well-known methods.

Figure 9:
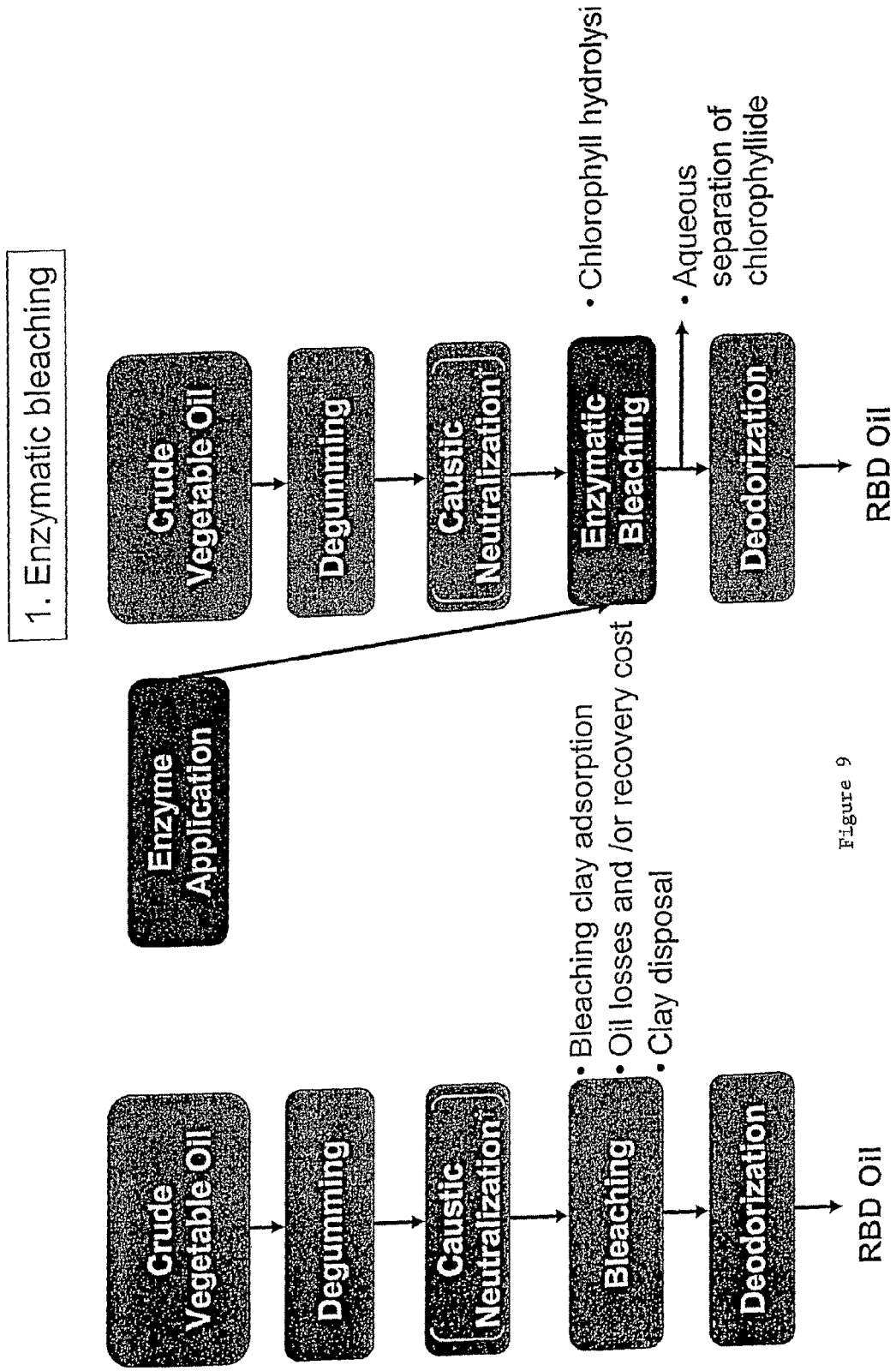
FIG. 9 illustrates and compares traditional versus an exemplary enzymatic decoloring (bleaching) reaction of the invention, as described in detail, below.

FIG. 9 illustrates and compares traditional versus an exemplary enzymatic decoloring (bleaching) process of the invention, where the enzymatic bleaching process can incorporate an esterase of the invention. In the traditional method crude vegetable oil is degummed, (optionally, caustic neutralized), bleached using, e.g., clay adsorption with subsequent clay disposal, and deodorization to produce "refined, bleached and deodorized" or RBD oil. In this exemplary enzymatic bleaching process of the invention, the crude vegetable oil is degummed, (optionally, caustic neutralized), bleached using, e.g., a polypeptide of the invention, such as a chlorophyllase of the invention, with subsequent aqueous separation of the chlorophyllide, followed by deodorization to produce a "refined, bleached and deodorized" or RBD oil. The need for the degumming depends on phosphorus content and other factors (all known in the art). Soy and canola are typically degummed.

Figure 10:
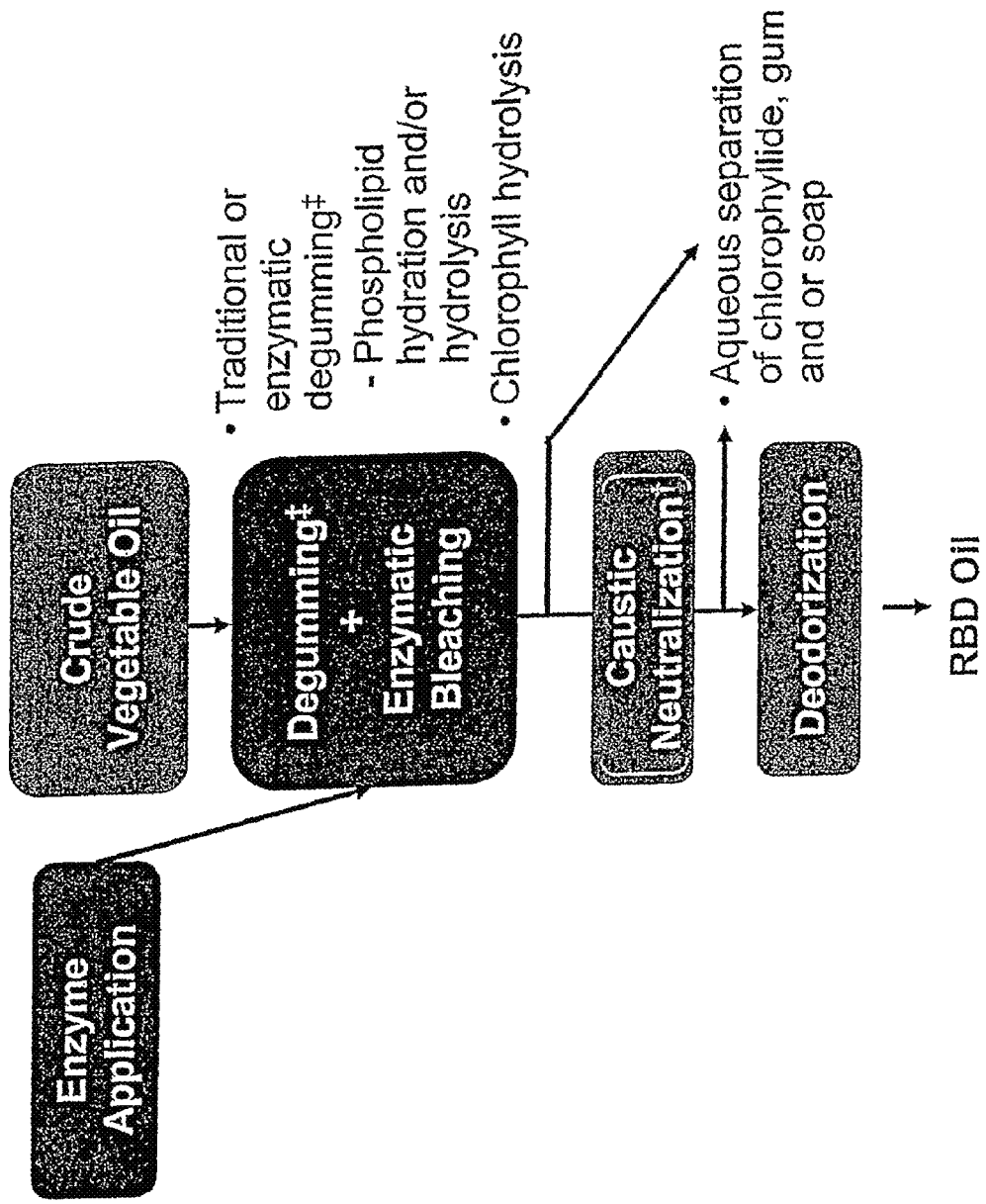
FIG. 10 illustrates an exemplary enzymatic decoloring (bleaching) reaction of the invention, as described in detail, below.

FIG. 10 illustrates an exemplary enzymatic decoloring (bleaching) process of the invention—a combined degumming-bleaching ("decoloring") process. In this exemplary enzymatic bleaching process of the invention, the crude vegetable oil is degummed and enzymatically bleached using a polypeptide of the invention, such as an esterase, e.g., a chlorophyllase, of the invention in one step, or "one pot." The degumming can be a "traditional" or an enzymatic degumming, e.g., involving phospholipid(s) and/or hydrolysis. In one aspect, the exemplary process of the invention comprises a subsequent aqueous separation step to remove the reaction product chlorophyllide, gum and/or soap. In one aspect, this is followed by deodorization to produce a "refined, bleached and deodorized" or RBD oil.

Figure 11:
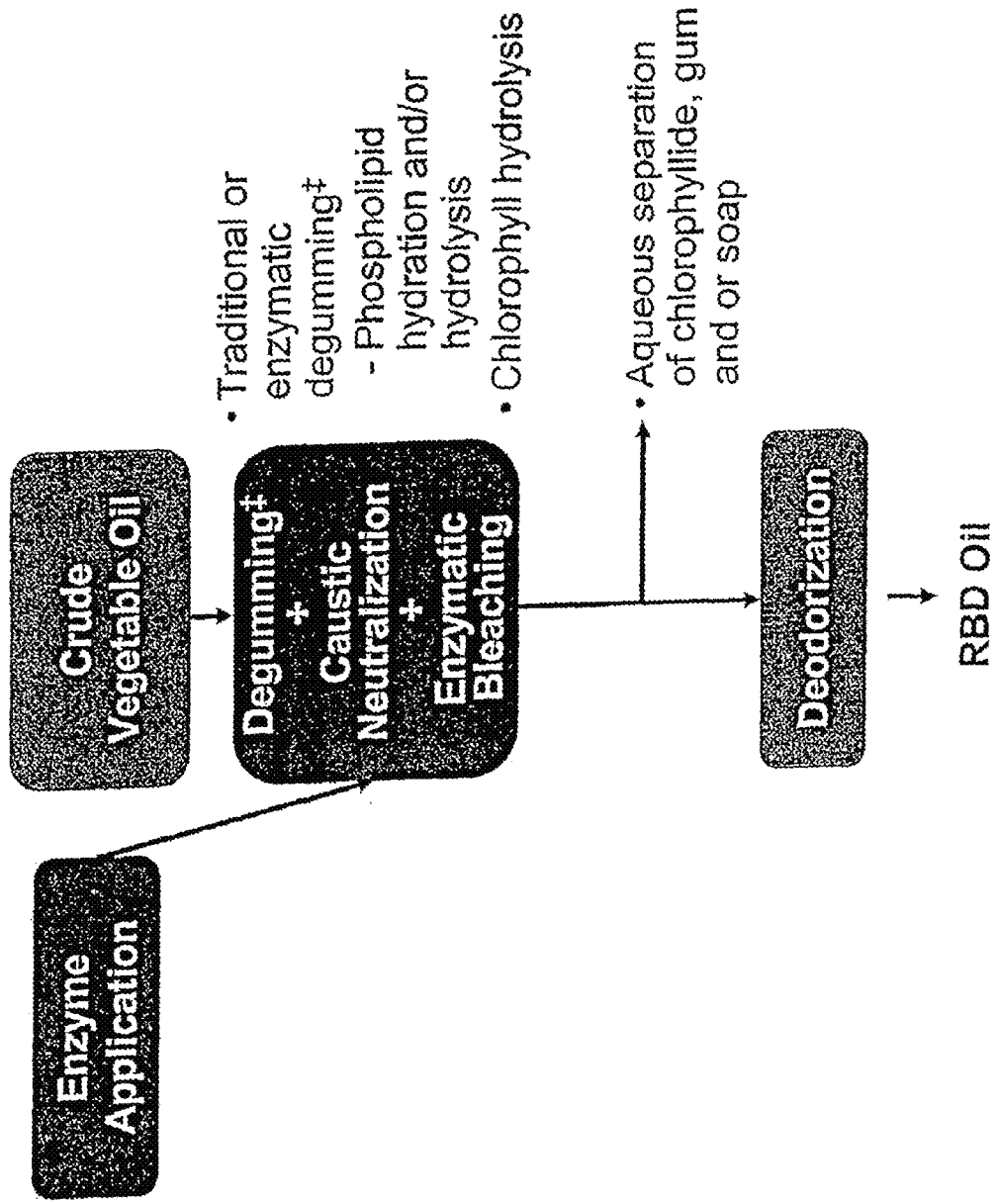
FIG. 11 illustrates an exemplary enzymatic decoloring (bleaching) process of the invention that combines degumming, enzymatic bleaching ("decoloring") and caustic neutralization steps, as described in detail, below.

FIG. 11 illustrates an exemplary enzymatic decoloring (bleaching) process of the invention that combines degumming, enzymatic bleaching ("decoloring") and caustic neutralization steps. In this exemplary enzymatic bleaching process of the invention, the crude vegetable oil is degummed, neutralized and enzymatically bleached using a polypeptide of the invention, such as an esterase, e.g., a chlorophyllase, of the invention in one step, or "one pot." The degumming can be a "traditional" or an enzymatic degumming, e.g., involving phospholipid(s) and/or hydrolysis. In one aspect, the exemplary process of the invention comprises a subsequent aqueous separation step to remove the reaction product chlorophyllide, gum and/or soap.

Figure 12:
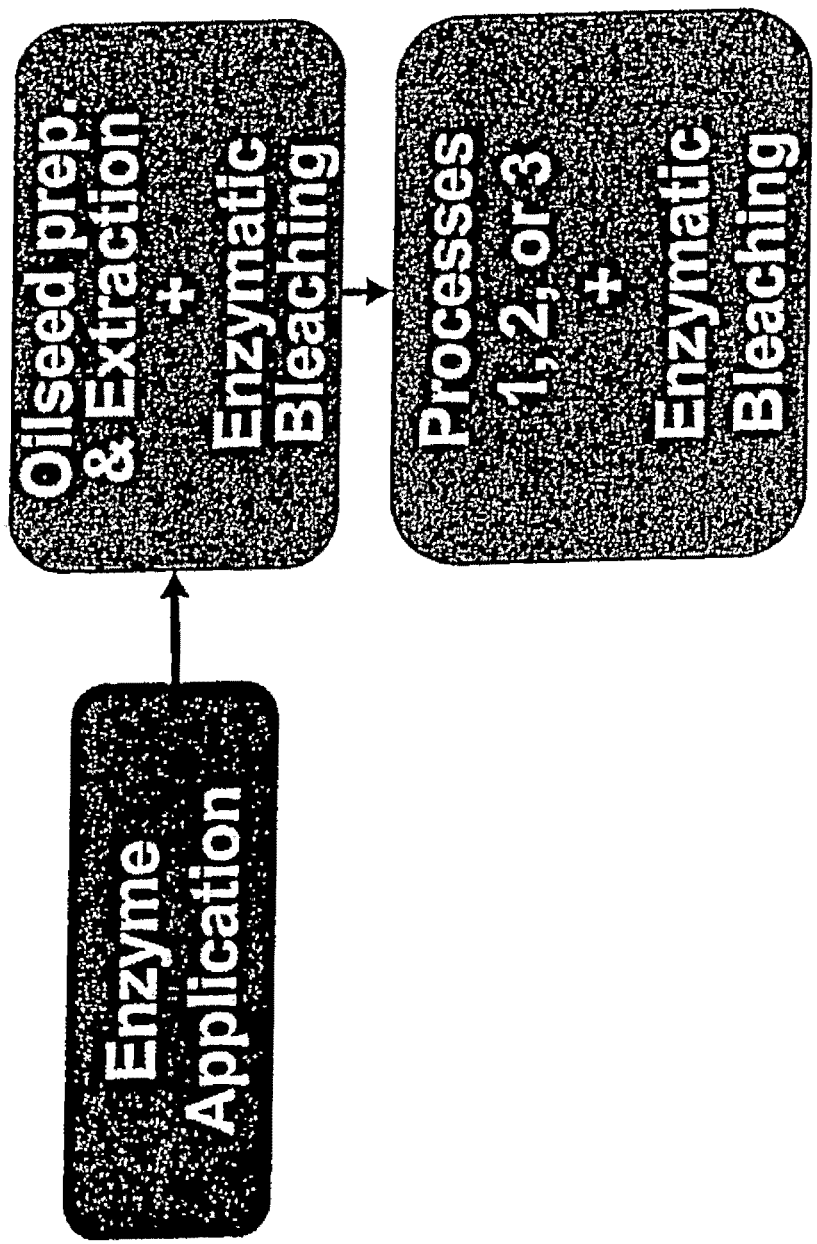
FIG. 12 illustrates an exemplary enzymatic decoloring (bleaching) process of the invention as described in detail, below.

FIG. 12 illustrates an exemplary enzymatic decoloring (bleaching) process of the invention that comprises application of a polypeptide of the invention, such as an esterase, e.g., a chlorophyllase to an oilseed preparation, followed by a subsequent aqueous separation step (to remove, e.g., the reaction product chlorophyllide, or gums and/or soaps), followed by the processes illustrated in FIG. 9, 10, or 11.

Figure 13:
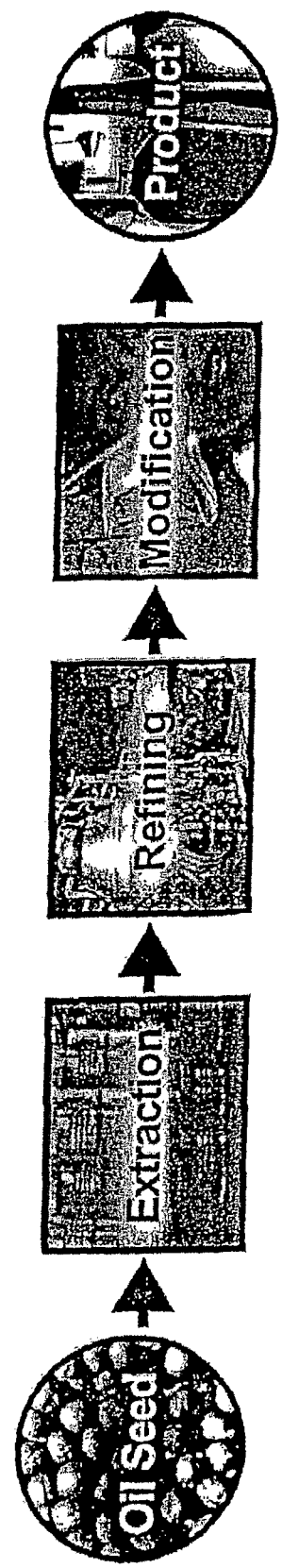
FIG. 13 illustrates an exemplary oilseed refining scheme comprising extraction, refining and modification of an oilseed using an esterase of the invention, as described in detail, below.

FIG. 13 illustrates a general oilseed refining scheme comprising extraction, refining and modification of an oilseed, where in addition to a polypeptide of the invention, such as an esterase, e.g., a chlorophyllase to an oilseed in one or several or all of these steps, other polypeptides and/or chemicals are also added, e.g., cellulase, hemicellulase, protease, pectinase, phospholipase A, B, C and/or D, esterase (e.g., a selective esterase), a lipase (e.g., 1,3 lipase), a selective lipase, a known chlorophyllase or other enzyme involved in chlorophyll catabolism, and the like.

Figure 14:
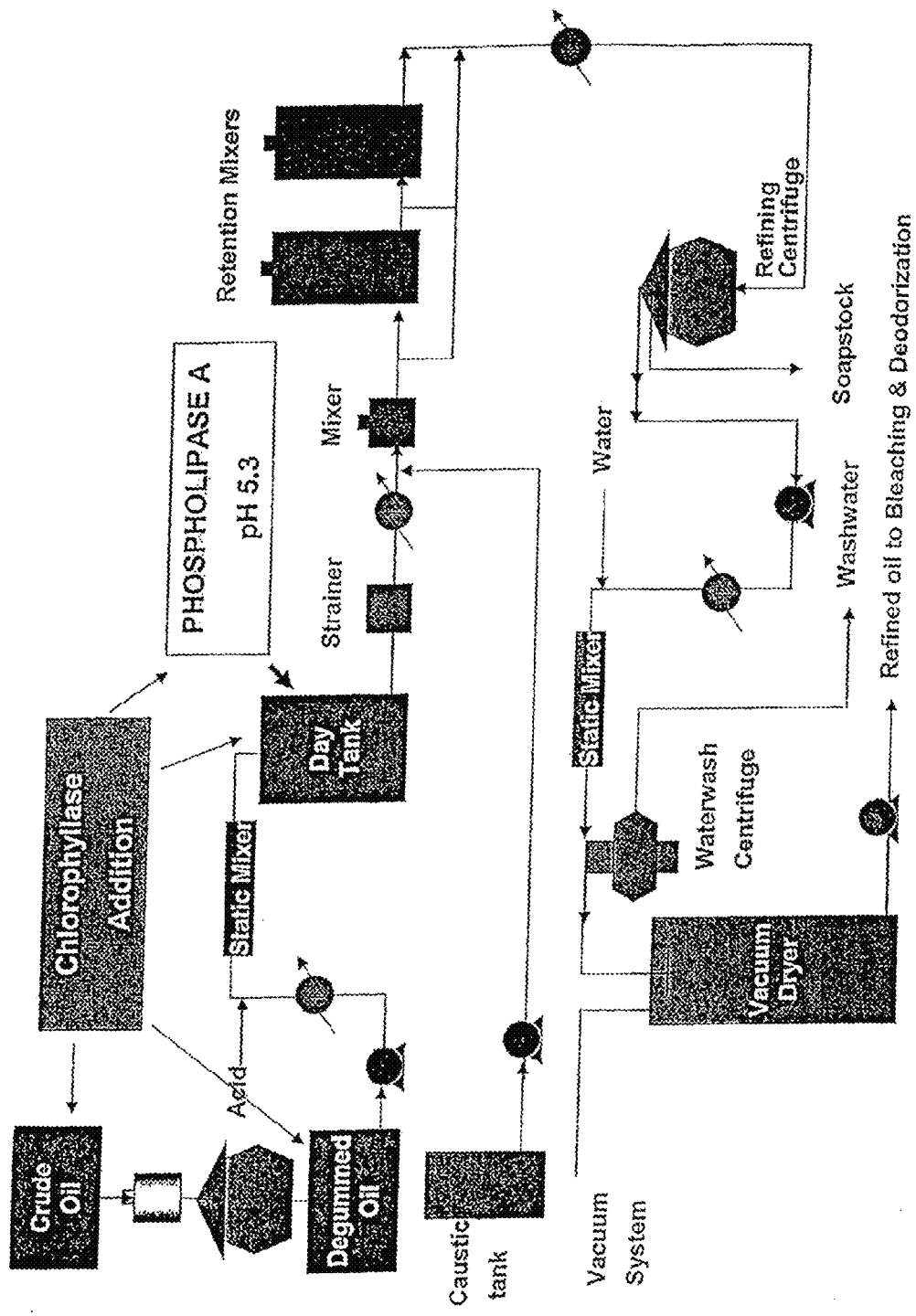
FIG. 14 illustrates an exemplary industrial process of the invention—a biodegumming process, comprising use of at least one polypeptide of the invention, as described in detail, below.

FIG. 14 illustrates an exemplary industrial process of the invention—a biodegumming process, comprising use of a phospholipase A and at least one polypeptide of the invention having chlorophyllase enzyme activity. The at least one polypeptide of the invention having chlorophyllase activity can be added to one or several or all of the following steps:

added to the crude oil, in the degumming process or in the degummed oil, a storage or holding tank, with the phospholipase A (e.g., in "the day tank" of the figure) and/or the caustic tank.

Figure 15:
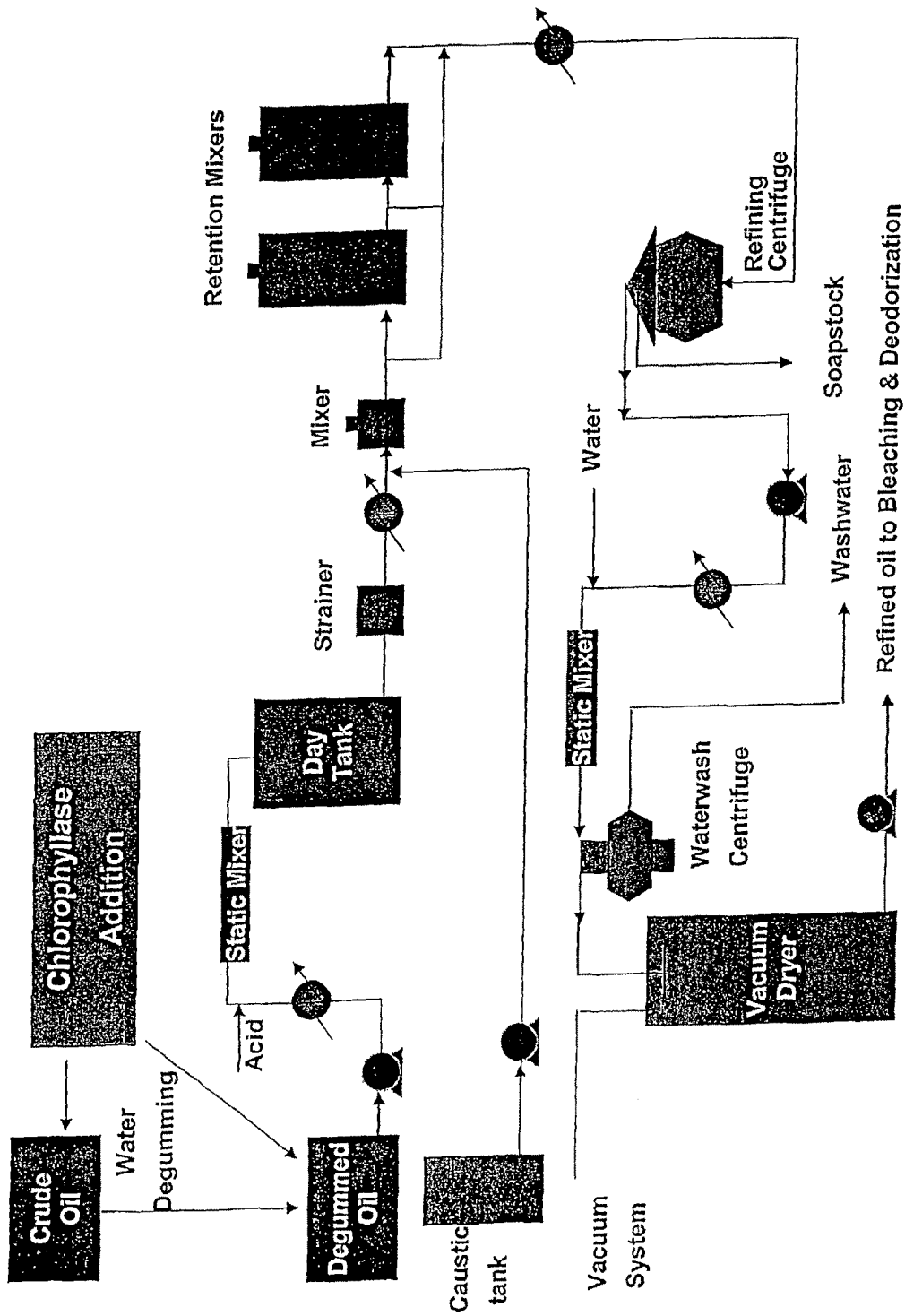
FIG. 15 illustrates another exemplary industrial process of the invention comprising use of at least one polypeptide of the invention, as described in detail, below.

FIG. 15 illustrates another exemplary industrial process of the invention comprising use of at least one polypeptide of the invention having chlorophyllase enzyme activity. The at least one polypeptide of the invention having chlorophyllase activity can be added to one or several or all of the following steps: added to the crude oil, in the degumming process or in the degummed oil, a storage or holding tank, a caustic tank and/or a retention mixer.

Figure 16:
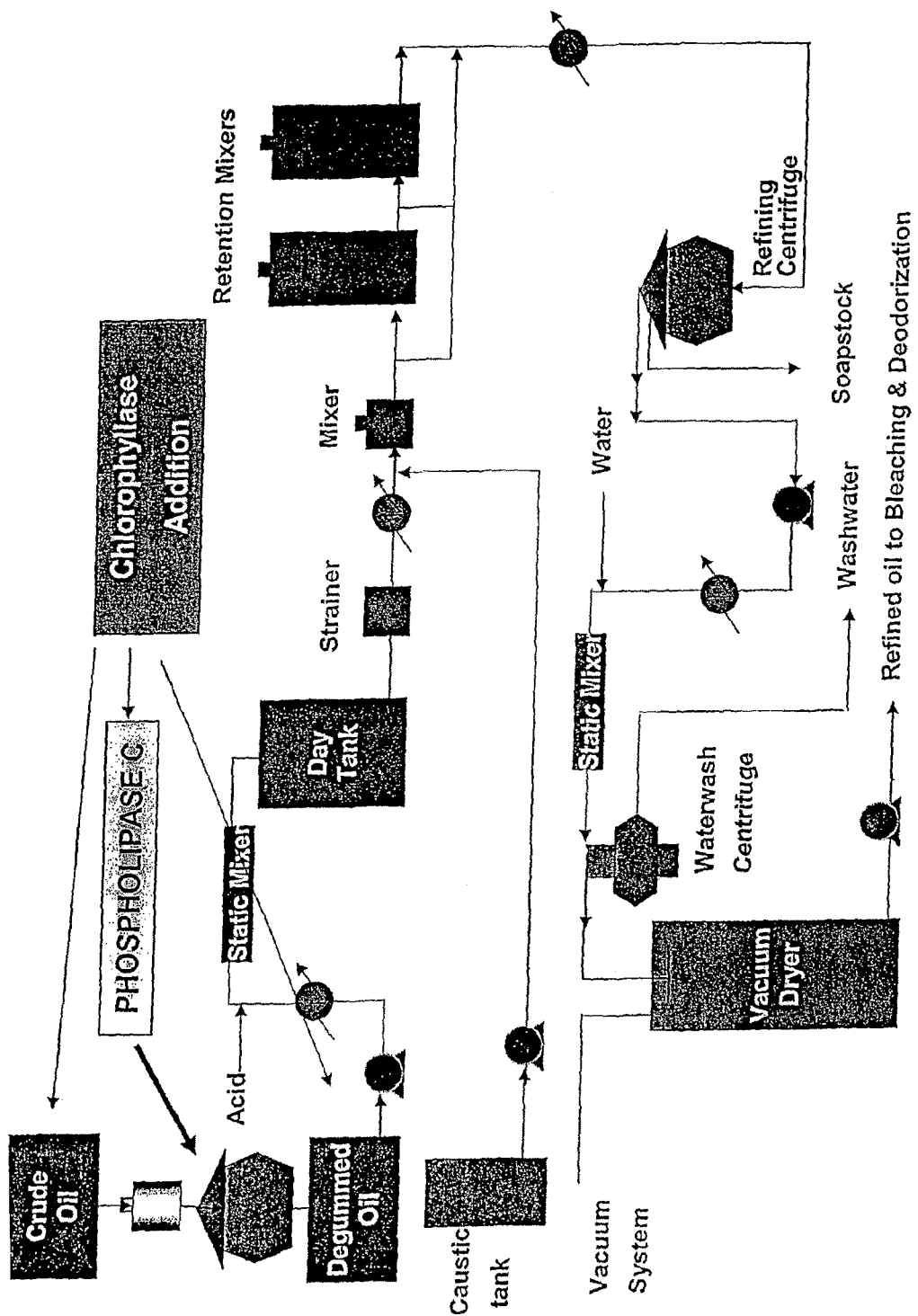
FIG. 16 illustrates another exemplary industrial process of the invention comprising use of at least one polypeptide of the invention having chlorophyllase enzyme activity.

FIG. 16 illustrates another exemplary industrial process of the invention comprising use of at least one polypeptide of the invention having chlorophyllase enzyme activity. In this exemplary process, phospholipase C (PLC) is added into the degumming process or in the degummed oil with the chlorophyllase enzyme of the invention. The at least one polypeptide of the invention having chlorophyllase activity can be added to one or several or all of the following steps: added to the crude oil, in the degumming process or in the degummed oil (with a PLC), a storage or holding tank, a caustic tank and/or a retention mixer.

Oil Degumming and Vegetable Oil Processing

The compositions and methods of the invention can be used in various vegetable oil processing steps, such as in vegetable oil extraction, particularly, in the removal of "phospholipid gums" in a process called "oil degumming,".

The compositions and methods of the invention can be used in methods for processing vegetable oils from various sources, such as rice bran, soybeans, rapeseed, peanuts and other nuts, sesame, sunflower, palm and corn. The methods can used in conjunction with processes based on extraction with as hexane, with subsequent refining of the crude extracts to edible oils. The first step in the refining sequence is the so-called "degumming" process, which serves to separate phosphatides by the addition of water. The material precipitated by degumming is separated and further processed to mixtures of lecithins. The commercial lecithins, such as soybean lecithin and sunflower lecithin, are semi-solid or very viscous materials. They consist of a mixture of polar lipids, mainly phospholipids, and oil, mainly triglycerides. The compositions and methods of the invention can be used before or after any step in a process, or before or after any combination of steps, or before or after all of the steps, in a process, e.g., prior to, during or following mechanical and/or chemical extraction, degumming and/or bleaching and the like.

The compositions and methods of the invention can be used in (i.e., in conjunction with) any "degumming" procedure, including water degumming, ALCON oil degumming (e.g., for soybeans), safinco degumming, "super degumming," UF degumming, TOP degumming, uni-degumming, dry degumming and ENZYMAX™ degumming. See, e.g., U.S. Pat. Nos. 6,355,693; 6,162,623; 6,103,505; 6,001,640; 5,558,781; 5,264,367. Compositions and methods of the invention can be used in any oil processing method, e.g., degumming or equivalent processes. For example, compositions and methods of the invention can be used in processes as described in U.S. Pat. Nos. 5,558,781; 5,288,619; 5,264,367; 6,001,640; 6,376,689; WO 0229022; oil degumming as described, e.g., in WO 98/18912; processes as described in JP Application No.: H5-132283 (filed Apr. 25, 1993); EP Application number: 82870032.8, and the like. Various "degumming" procedures incorporated by the methods of the invention are described in Bockisch, M. (1998) In Fats and Oils Handbook, The extraction of Vegetable Oils (Chapter 5), 345-445, AOCS Press, Champaign, Ill. The compositions and methods of the invention can be used in the industrial application of enzymatic degumming of triglyceride oils as described, e.g., in EP 513 709.

In one aspect, compositions and methods of the invention are used to treat vegetable oils, e.g., crude oils, such as rice bran, soy, canola, flower and the like. In one aspect, this improves the efficiency of the degumming process. In one aspect the methods of the invention result in the improved separation of chlorophyll from the oil phase, e.g., during centrifugation. The improved separation of these phases can result in more efficient removal of chlorophylls from the oil, including both hydratable and nonhydratable oils.

The compositions and methods of the invention can be used in the industrial application of enzymatic degumming as described, e.g., in CA 1102795, which describes a method of isolating polar lipids from cereal lipids by the addition of at least 50% by weight of water. This method is a modified degumming in the sense that it utilizes the principle of adding water to a crude oil mixture.

In one aspect, the invention provides enzymatic processes comprising use of compositions and methods of the invention comprising hydrolysis of hydrated phospholipids in oil at a temperature of about 20° C. to 40° C., at an alkaline pH, e.g., a pH of about pH 8 to pH 10, using a reaction time of about 3 to 10 minutes.

In various exemplary processes of the invention, a number of distinct steps comprise the degumming process preceding the core bleaching and deodorization refining processes. These steps include heating, mixing, holding, separating and drying. Following the heating step, water and often acid are added and mixed to allow the insoluble phospholipid "gum" to agglomerate into particles which may be separated. While water separates many of the phosphatides in degumming, portions of the phospholipids are non-hydratable phosphatides (NHPs) present as calcium or magnesium salts. Degumming processes address these NHPs by the addition of acid. Following the hydration of phospholipids, the oil is mixed, held and separated by centrifugation. Finally, the oil is dried and stored, shipped or refined. The resulting gums are either processed further for lecithin products or added back into the meal. As noted above, the compositions and methods of the invention can be used before or after any of these steps, or before or after any combination of steps, or before or after all of the steps, in any processing method.

Upon completion of an enzyme treatment of the invention, the treated liquid (e.g., oil) is separated with an appropriate means such as a centrifugal separator and the processed oil is obtained. In one aspect, compounds produced by enzyme modification of chlorophyll are partially or completely transferred into the aqueous phase and removed from the oil phase. Upon completion of the enzyme treatment, if necessary, the processed oil can be additionally washed with water or organic or inorganic acid such as, e.g., acetic acid, phosphoric acid, succinic acid, and the like, or with salt solutions.

In one exemplary process for ultra-filtration degumming, an enzyme used in a method of the invention is bound to a filter or the enzyme is added to an oil prior to filtration. Enzymes used in compositions or methods of the invention can be immobilized to any substrate, e.g., filters, fibers, columns, beads, colloids, gels, hydrogels, meshes and the like.

Compositions and methods of the invention can be used to improve oil extraction, oil degumming and caustic neutralization (e.g., vegetable oils). In one aspect, a composition or method of the invention and at least one plant cell wall degrader (e.g., a cellulase, a hemicellulase or the like, to soften walls and increase yield at extraction) is used in a process of the invention. In an exemplary method, to improve oil extraction and oil degumming, a phospholipase, e.g., a phospholipase C, or another hydrolase (e.g., a cellulase, a hemicellulase, an esterase, a protease and/or a phosphatase) is used. For example, in one aspect, during a crushing step associated with oil production (including but not limited to soybean, canola, sunflower, rice bran oil) a phospholipase or other enzyme can be used. By using enzymes prior to or in place of solvent extraction, it is possible to increase oil yield and reduce the amount of hydratable and non-hydratable phospholipids in the crude oil. The overall reduction of phospholipids in the crude oil will result in improved yields during refining with the potential for eliminating the requirement for a separate degumming step prior to bleaching and deodorization.

Compositions and methods of the invention also can be practiced using processes as described in U.S. Pat. No. 5,414,100. For example, in one aspect, the methods or compositions further comprise chromatographic processes for deacidification of vegetable oils at ambient temperature. These processes can be retrofitted into deacidification operations using miscella refining or solvent extraction, crude vegetable oil is dissolved in a solvent such as isopropyl alcohol and passed through a column of activated alumina (aluminum oxide) at room temperature. The process, which eliminates physical contact between both oil and an alkaline reagent and oil and water, simplifies subsequent bleaching processes by also removing some color pigments. The spent alumina can be reactivated by washing it with a dilute solution of sodium hydroxide or potassium hydroxide.

Compositions and methods of the invention also can be practiced using processes as described in JP57156482, 1982 (application no. JP19810040794 19810320), describing refining vegetable fats or oils as by-products.

Compositions and methods of the invention also can be practiced using processes as described in U.S. Pat. No. 5,315,021. For example, in one aspect, the methods or compositions of the invention can be practiced with processes for removing chlorophyll color impurities from vegetable oils. The processes can comprise dispersing a source of phosphoric acid in vegetable oil to form a mixture having a moisture content of less than 0.1% by weight which mixture is maintained at a temperature in the range of 70° C. to 160° C. until a precipitate containing chlorophyll color impurities is formed. This can be followed separating the precipitated material from the oil to remove the chlorophyll color impurities with the precipitated material, e.g., during conventional oil processing up to and including the removal of bleaching clay from the oil.

Enzymatic Processing of Oilseeds

The compositions and methods of the invention can be used for enzymatic processing of oilseeds, including soybean, canola (rapeseed), coconut, avocado and olive paste. In one aspect, these processes of the invention can increase the oil yield and to improve the nutritional quality of the obtained meals. In some aspects, enzymatic processing of oilseeds using the enzymes and methods of the invention will provide economical and environmental benefits, as well as alternative technologies for oil extraction and processing food for human and animal consumption. In alternative aspects, the processes of the invention further comprise use of phospholipases, proteases, phosphatases, phytases, xylanases, amylases (e.g., α-amylases), glucanases (e.g., β-glucanases), polygalacturonases, galactolipases, cellulases, hemicellulases, pectinases and other plant cell wall degrading enzymes, as well as mixed enzyme preparations and cell lysates. In alternative aspects, the processes of the invention can be practiced in conjunction with other processes, e.g., enzymatic treatments, e.g., with carbohydrases, including cellulase, hemicellulase and other side degrading activities, or, chemical processes, e.g., hexane extraction of soybean oil. The enzymatic treatment can increase the oil extractability by 8-10% when the enzymatic treatment is carried out prior to the solvent extraction.

In alternative aspects, the processes of the invention can be practiced with aqueous extraction processes. The aqueous extraction methods can be environmentally cleaner alternative technologies for oil extraction. The processes of the invention can also use enzymes that hydrolyze the structural polysaccharides forming the cell wall of oilseeds, or that hydrolyze the proteins which form the cell and lipid body membranes, e.g., utilizing digestions comprising cellulase, hemicellulase, and/or protopectinase for extraction of oil from soybean cells. In one aspect, methods are practiced with an enzyme of the invention as described by Kasai (2003) J. Agric. Food Chem. 51:6217-6222, who reported that the most effective enzyme to digest the cell wall was cellulase.

In one aspect, proteases are used in combination with the methods of the invention. The combined effect of operational variables and enzyme activity of protease and cellulase on oil and protein extraction yields combined with other process parameters, such as enzyme concentration, time of hydrolysis, particle size and solid-to-liquid ratio has been evaluated. In one aspect, methods of the invention are practiced with protocols as described by Rosenthal (2001) Enzyme and Microb. Tech. 28:499-509, who reported that use of protease can result in significantly higher yields of oil and protein over the control when heat treated flour is used.

In one aspect, complete protein, pectin, and hemicellulose extraction are used in combination with the methods of the invention. The plant cell consists of a series of polysaccharides often associated with or replaced by proteins or phenolic compounds. Most of these carbohydrates are only partially digested or poorly utilized by the digestive enzymes. The disruption of these structures through processing or degrading enzymes can improve their nutrient availability. In one aspect, methods of the invention are practiced with protocols as described by Ouhida (2002) J. Agric. Food Chem. 50:1933-1938, who reported that a significant degradation of the soybean cell wall cellulose (up to 20%) has been achieved after complete protein, pectin, and hemicellulose extraction.

In one aspect, the methods of the invention further comprise incorporation of various enzymatic treatments in the treatment of seeds, e.g., canola seeds, these treatments comprising use of proteases, cellulases, and hemicellulases (in various combinations with each other and with one or more enzymes of the invention). For example, the methods can comprise enzymatic treatments of canola seeds at 20 to 40 moisture during the incubation with enzymes prior to a conventional process; as described, e.g., by Sosulski (1990) Proc. Can. Inst. Food Sci. Technol. 3:656. The methods of the invention can further comprise incorporation of proteases, α-amylases, polygalacturonases (in various combinations with each other and with one or more enzymes of the invention) to hydrolyze cellular material in coconut meal and release the coconut oil, which can be recovered by centrifugation, as described, e.g., by McGlone (1986) J. of Food Sci. 51:695-697. The methods of the invention can further comprise incorporation of pectinases, α-amylases, proteases, cellulases in different combinations (with each other and with one or more enzymes of the invention) to result in significant yield improvement (~70% in the best case) during enzymatic extraction of avocado oil, as described, e.g., by Buenrostro (1986) Biotech. Letters 8(7):505-506. In processes of the invention for olive oil extraction, olive paste is treated with cellulase, hemicellulase, poligalacturonase, pectin-methyltransferase, protease and their combinations (with each other and with one or more enzymes of the invention), as described, e.g., by Montedoro (1976) Acta Vitamin. Enzymol. (Milano) 30:13.

In one aspect, the methods of the invention further comprise incorporation of various enzymatic treatments in the treatment of seeds, e.g., canola seeds, these treatments comprising use of proteases, cellulases, and hemicellulases (in various combinations with each other and with one or more enzymes of the invention). For example, the methods can comprise enzymatic treatments of canola seeds at 20 to 40 moisture during the incubation with enzymes prior to a conventional process; as described, e.g., by Sosulski (1990) Proc. Can. Inst. Food Sci. Technol. 3:656. The methods of the invention can further comprise incorporation of proteases, α-amylases, polygalacturonases (in various combinations with each other and with one or more enzymes of the invention) to hydrolyze cellular material in coconut meal and release the coconut oil, which can be recovered by centrifugation, as described, e.g., by McGlone (1986) J. of Food Sci. 51:695-697. The methods of the invention can further comprise incorporation of pectinases, α-amylases, proteases, cellulases in different combinations (with each other and with one or more enzymes of the invention) to result in significant yield improvement (~70% in the best case) during enzymatic extraction of avocado oil, as described, e.g., by Buenrostro (1986) Biotech. Letters 8(7):505-506. In processes of the invention for olive oil extraction, olive paste is treated with cellulase, hemicellulase, poligalacturonase, pectin-methyltransferase, protease and their combinations (with each other and with one or more enzymes of the invention), as described, e.g., by Montedoro (1976) Acta Vitamin. Enzymol. (Milano) 30:13.

In one aspect, the compositions and methods of the invention can be practiced with methods as described in U.S. Pat. No. 6,376,689. For example, in one aspect, the compositions and methods of the invention can comprise a single-step acid degumming/decolorizing process that removes chlorophyll-type compounds from vegetable oils from seeds, especially frost damaged seeds which have large amounts of chlorophyll-type compounds. In one aspect, the methods of the invention further comprise a mixture of aqueous sulfuric and phosphoric acids that is blended with the oil to remove chlorophyll-type compounds from the oil. The purified oil can have less than about 5 ppm chlorophyll-type compounds, less than about 50 ppm phosphorus or less than about 1.0 weight percent free fatty acids.

Purification of Phytosterols from Vegetable Oils

The compositions (e.g., esterases) and methods of the invention can also be used in conjunction with methods and processes for the purification of phytosterols and triterpenes, or plant sterols, from vegetable oils. Phytosterols that can be purified using methods of the invention include β-sitosterol, campesterol, stigmasterol, stigmastanol, β-sitostanol, sitostanol, desmosterol, chalinasterol, poriferasterol, clionasterol and brassicasterol. Plant sterols are important agricultural products for health and nutritional industries. Thus, compositions (e.g., esterases) and methods of the invention can be used to make emulsifiers for cosmetic manufacturers and steroidal intermediates and precursors for the production of hormone pharmaceuticals. The compositions (e.g., esterases) and methods of the invention can be used to make (e.g., purify) analogs of phytosterols and their esters for use as cholesterol-lowering agents with cardiologic health benefits. The compositions (e.g., esterases) and methods of the invention can be used to purify plant sterols to reduce serum cholesterol levels by inhibiting cholesterol absorption in the intestinal lumen. The compositions (e.g., esterases) and methods of the invention can be used to purify plant sterols that have immunomodulating properties at extremely low concentrations, including enhanced cellular response of T lymphocytes and cytotoxic ability of natural killer cells against a cancer cell line. The compositions (e.g., esterases) and methods of the invention can be used to purify plant sterols for the treatment of pulmonary tuberculosis, rheumatoid arthritis, management of HIV-infested patients and inhibition of immune stress, e.g., in marathon runners.

The compositions (e.g., esterases) and methods of the invention can be used to purify sterol components present in the sterol fractions of commodity vegetable oils (e.g., coconut, canola, cocoa butter, corn, cottonseed, linseed, olive, palm, peanut, rice bran, safflower, sesame, soybean, sunflower oils), such as sitosterol (40.2-92.3%), campesterol (2.6-38.6%), stigmasterol (0-31%) and 5-avenasterol (1.5-29%).

Vegetable Oil Refining Apparatus

The invention provides product of manufacture comprising a degumming system for the enzymatic treatment of chlorophyll-containing or chlorophyll-contaminated compositions comprising (a) a vegetable oil refining apparatus; and (b) a polypeptide having an chlorophyllase activity operably integrated into the vegetable oil refining apparatus, wherein the activity of the polypeptide comprises catalysis of a chlorophyll-modifying reaction, and the vegetable oil refining apparatus can react a chlorophyll-containing or chlorophyll-contaminated composition with the polypeptide to under conditions wherein the polypeptide can catalyze a chlorophyll-modifying reaction.

The products of manufacture of the invention can comprise any vegetable oil refining apparatus or combination thereof, e.g., an oil leaving expellor (e.g., from Pennwalt Corp.), or a gravitational gum separation device.

The invention provides product of manufacture comprising immobilized enzymes, e.g., an immobilized chlorophyllase, e.g., an esterase of the invention. In one aspect of the product of manufacture, the chlorophyllase comprises a silica-immobilized chlorophyllase. The silica comprises a silica gel or equivalent. The silica comprises a TriSyl Silica or a SORB-SIL R™ silica.

In one aspect, the products of manufacture of the invention comprise apparatus for adjusting pH, e.g., increasing pH ("caustic treatment"), and then, alternatively, neutralizing pH.

The invention will be further described with reference to the following examples; however, it is to be understood that the invention is not limited to such examples.

EXAMPLES

Example 1

Exemplary Esterase Activity Assay

The following example demonstrates an exemplary esterase (chlorophyllase activity) assay for isolating and characterizing enzymes of the invention and the nucleic acids that encode them, and to determine if a polypeptide is within the scope of the invention.

Esterases were screened for activity on chlorophyll from spinach to produce chlorophyllide. In this exemplary esterase (chlorophyllase activity) assay the esterase screening format comprises:

Plates screened in duplicate.
Positive (CHLase) & negative controls on each plate.
1 mM CHL, 20% cell lysate, 20% acetone, pH 7.5, 0.01% HBT.
24 hr incubation time at 30° C. in the dark.
100 mL reaction volume.
Analysis by LC-VIS; injection of 1 mL sample.

Figure 2:
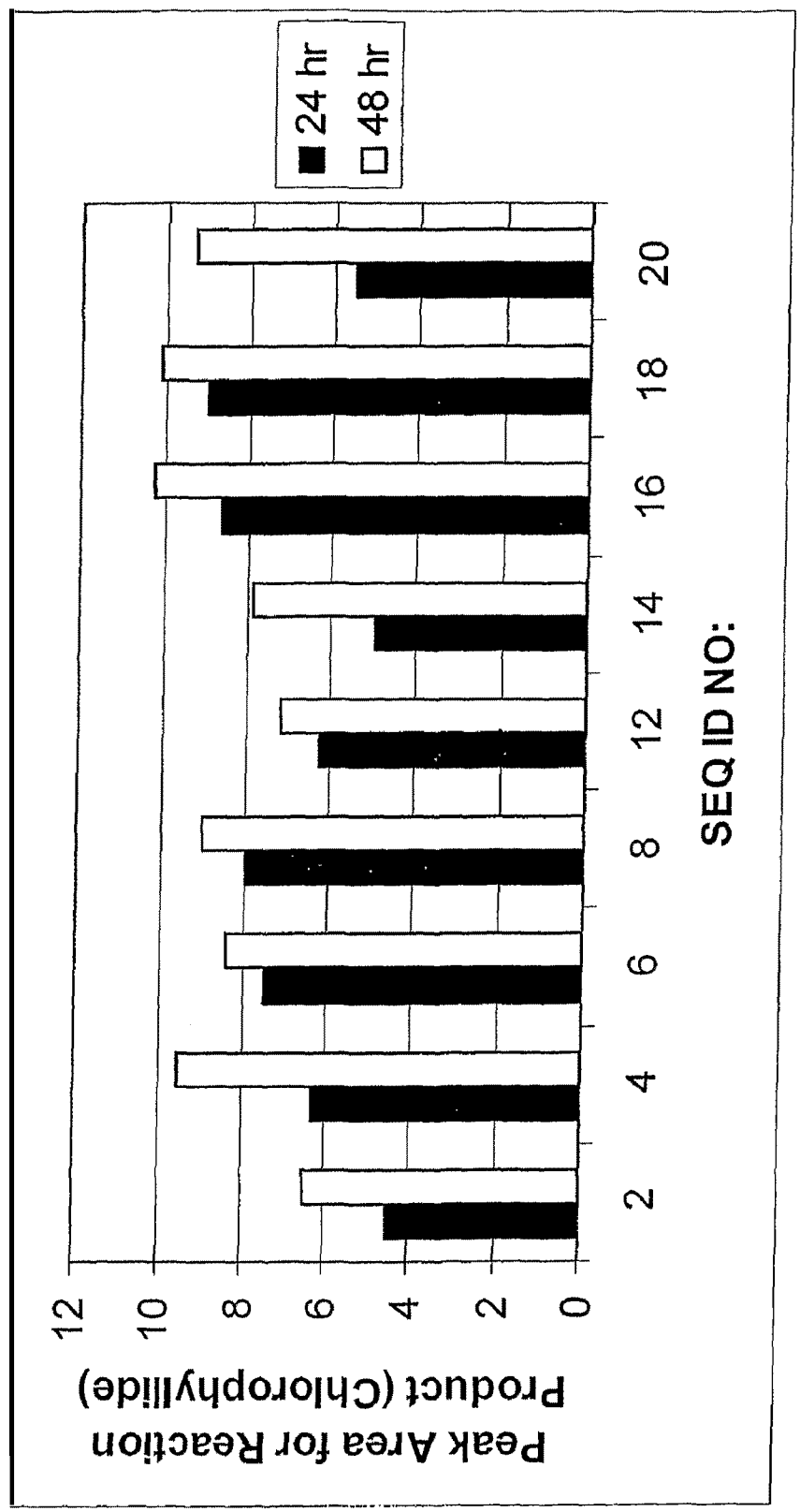
FIG. 2 and FIG. 3 illustrate data showing the results of an esterase (chlorophyllase activity) activity assay using exemplary enzymes of the invention, as described in detail in Example 1, below.
Figure 3:
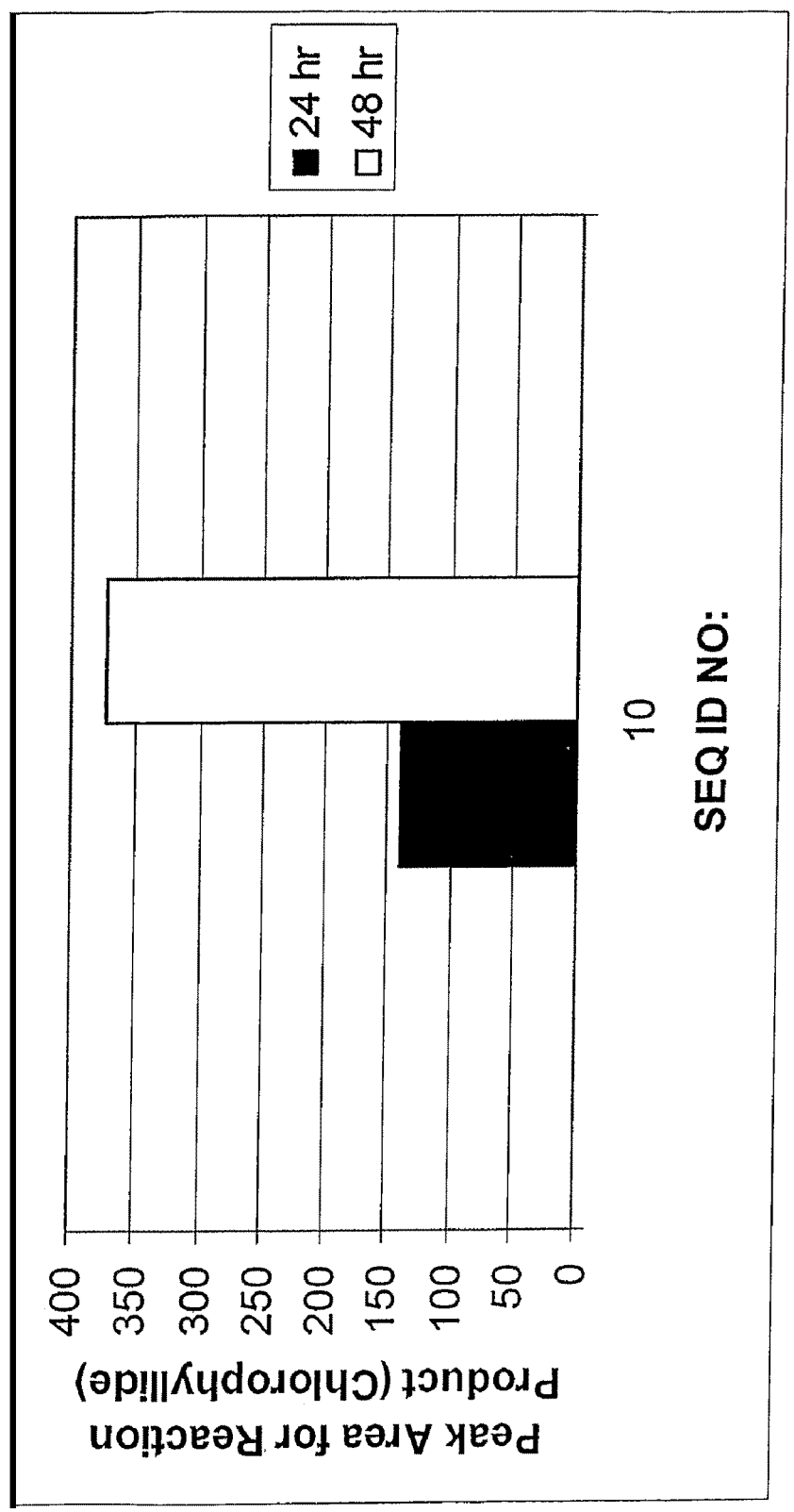
Figure 4:
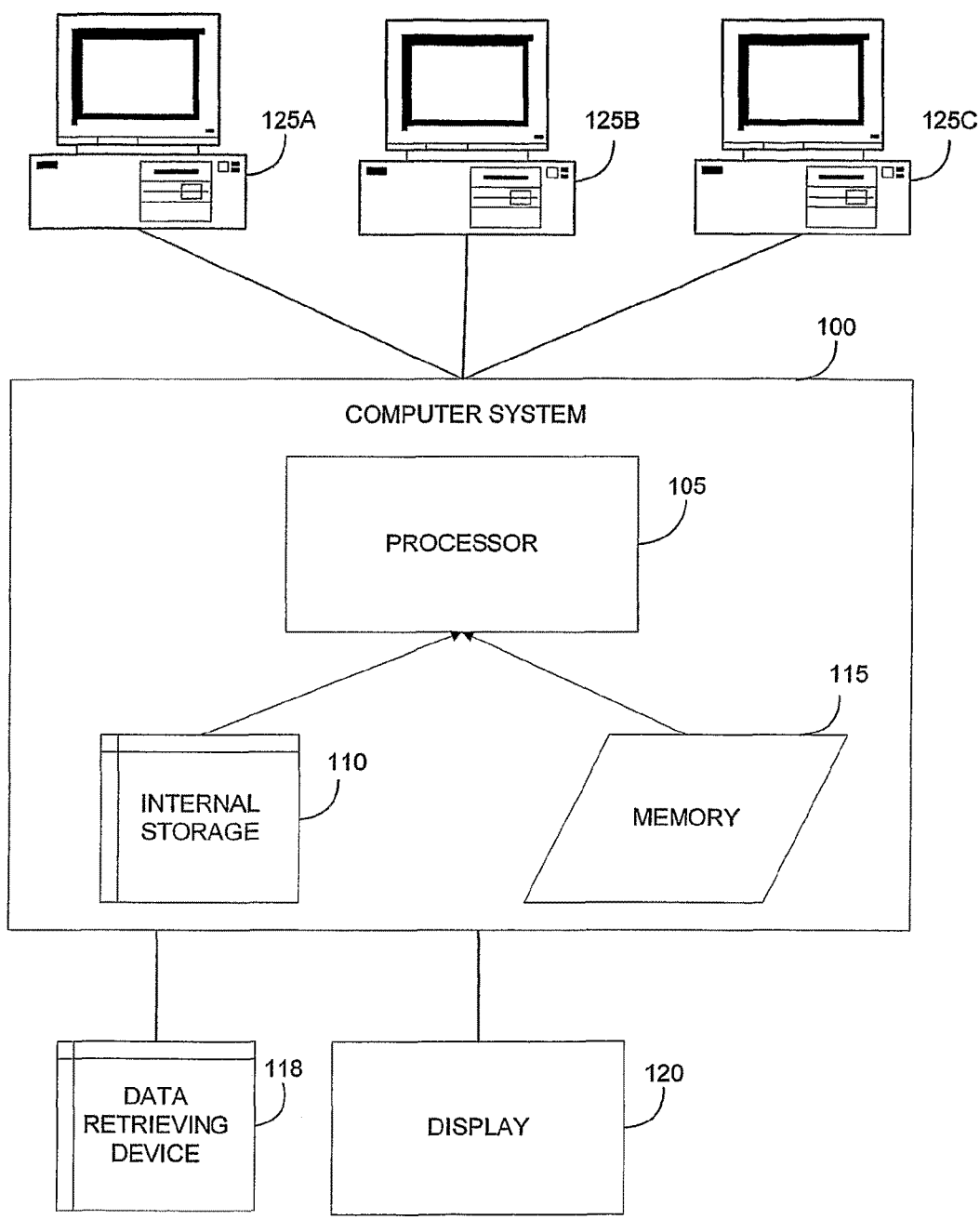
FIG. 4 is a block diagram of an exemplary computer system of the invention, as described in detail, below.

This esterase screening method used HPLC to analyze reaction products. FIG. 2 and FIG. 3 illustrate data showing the results of the esterase (chlorophyllase activity) activity assay using the indicated exemplary enzymes of the invention.

For the HPLC:
Column: Cromolith SpeedROD RP-18e 50-4, 6 mm (Cat# UM1082/086)
Flow: 1.0 mL/min; Injection: 1.0 mL.

| T (min) | A | B | C |
|---|---|---|---|
| 0 | 10% | 80% | 10% |
| 2.3 | 10% | 80% | 10% |
| 2.31 | 0% | 50% | 50% |
| 4 | 0% | 50% | 50% |
| 4.1 | 10% | 80% | 10% |
| 7 | 10% | 80% | 10% |

A: H2O
B: MEOH + 1 mM NH4OAc
C: MTBE

| DAD signal | L (nm) | Bw | Reference 1 | Bw |
|---|---|---|---|---|
| 1 | 660 | 20 | 710 nm | 10 |

| Compound | Rt |
|---|---|
| CHLa | 4.20 |
| CHLb | 4.15 |
| PHPa | 4.30 |
| PHPb | 4.25 |
| CHPa | 0.85 |
| CHPb | 0.80 |
| PHBa | 1.00 |
| PHBb | 0.95 |

The data illustrated in FIG. 2 illustrates increased levels of reaction product between 24 hr and 48 hr time points, were the levels of reaction product indicate chlorophyllase activity for SEQ ID NO:2, SEQ ID NO:4, SEQ ID NO:6, SEQ ID NO:8, SEQ ID NO:12, SEQ ID NO:14, SEQ ID NO:16, SEQ ID NO:18 and SEQ ID NO:20. The data illustrated in FIG. 3 illustrates increased levels of reaction product between 24 hr and 48 hr time points, were the levels of reaction product indicate chlorophyllase activity for SEQ ID NO:10.

A number of embodiments of the invention have been described. Nevertheless, it will be understood that various modifications may be made without departing from the spirit and scope of the invention. Accordingly, other embodiments are within the scope of the following claims.

What is claimed is:

1. A method for enzymatic treatment of a chlorophyll- or chlorophyll derivative-containing oil comprising the following steps:
   a) providing a chlorophyll or chlorophyll derivative containing oil
   b) providing at least one polypeptide having a chlorophyllase activity or a chlorophyll catabolic enzyme activity; and
   c) reacting the composition of step a) with the polypeptide of step b) under conditions wherein the polypeptide can catalyze a chlorophyll-modifying reaction,
   wherein the polypeptide:
   (i) has at least 95%, 96%, 97%, 98%, 99%, or more, or has 100% sequence identity to SEQ ID NO:10 and the polypeptide retains chlorophyllase or chlorophyllase catabolic activity; or
   (ii) is encoded by a nucleic acid sequence having at least 95%, 96%, 97%, 98%, 99%, or more, or has 100% sequence identity to SEQ ID NO:9; and the polypeptide retains chlorophyllase or chlorophyllase catabolic activity; or
   (iii) is the polypeptide of (i) or (ii) but lacking its homologous signal sequence or prepro sequence; or
   (iv) is the polypeptide of (i), (ii), or (iii), further comprising a heterologous sequence; or
   (v) is the polypeptide of (i), (ii), (iii), or (iv), further comprising a targeting sequence, an N-terminal identification peptide or a stability or simplified purification peptide sequence.

2. The method of claim 1, wherein the chlorophyll or chlorophyll derivative is a pheophytin.

3. The method of any claim 1 or 2, wherein the polypeptide is immobilized,
   wherein optionally the polypeptide is immobilized on an array, a cell, a metal, a resin, a polymer, a ceramic, a glass, a microelectrode, a graphitic particle, a bead, a gel, a plate, an array or a capillary tube,
   and optionally the polypeptide is immobilized on an inorganic support or organic support, and optionally the support comprises alumina, celite, Dowex-1-chloride, glass beads, silica, silica gel, alginate hydrogel or alginate bead or equivalent, or optionally the inorganic support or organic support comprises alumina, celite, Dowex-1-chloride, glass beads, silica gel, alginate hydrogel or alginate bead or equivalent, or optionally the silica comprises a silica gel or equivalent, and optionally the silica comprises a TriSyl Silica or a SORBSIL R silica.

4. The method of claim 1, wherein the chlorophyll- or chlorophyll-derivative- containing oil
   (a) is derived from a plant, an animal or an algae, or a mixture thereof,
   (b) comprises a plant material, plant oil or plant extract,
   (c) comprises a vegetable oil or a seed oil,
   (d) comprises a palm oil or a canola oil,
   (e) comprises a crude oil or a refined oil,
   (f) comprises an undiluted crude oil preparation, or
   (g) comprises an algae preparation.

5. The method of claim 1, wherein at least one step of the treatment is performed in a reaction vessel, and optionally the reaction vessel comprises a gravitational gum separation device or a holding tank.

6. The method of claim 1, wherein at least one step of the treatment is performed in a cell extract or in a whole cell.

7. The method of claim 1, wherein the polypeptide is used with a lipoxygenase.

8. The method of claim 1, to generate a chlorophyllide or a pheophorbide by enzymatic degradation of a chlorophyll or a chlorophyll derivative, which is removed by
   (a) adsorbing the chlorophyllide or pheophorbide onto an absorbant, silica gel or equivalent, or
   (b) step (a), further comprising a heating step prior to adsorbing the chlorophyllide or pheophorbide onto an absorbant, silica gel or equivalent.

9. The method of claim 1, wherein the treatment further comprises modifying pH to promote aqueous separation of a chlorophyllide or pheophorbide generated by the enzyme treatment.

10. The method of claim 1, wherein the treatment further comprises removal of the product modified chlorophyll or the modified pheophytin in an aqueous extraction.

11. The method of claim 1, wherein the treatment further comprises a caustic neutralization step.

12. The method of claim 1, wherein the treatment further comprises an adsorbent-free or reduced adsorbent silica refining step to remove
   (a) a chlorophyllide generated by enzymatic degradation of chlorophyll in the oil, or
   (b) a pheophorbide generated by enzymatic degradation of pheophytin in the oil.

13. The method of claim 1, wherein polypeptide is used with a phospholipase and optionally the phospholipase is a phospholipase C.

14. The method of claim 1, wherein the treatment is included in a degumming process.

15. The method of claim 1, wherein the treatment further comprises the removal of residual chlorophyll or equivalent compounds not modified by the polypeptide, or pesticides or polycyclic aromatic hydrocarbons, using bleaching clay or other adsorbent, such as silica or equivalent compounds.

16. The method of claim 1, wherein the polypeptide comprises SEQ ID NO:10, or a polypeptide encoded by SEQ ID NO:9.

* * * * *

SEQUENCE LISTING

<160> NUMBER OF SEQ ID NOS: 27

<210> SEQ ID NO 1
<211> LENGTH: 915
<212> TYPE: DNA
<213> ORGANISM: Unknown
<220> FEATURE:
<223> OTHER INFORMATION: Obtained from environmental sample

<400> SEQUENCE: 1

```
atgtcgcgtg tctgtcttcc actcacactc acactcgcac tcacactctc tgccagagca      60
gcggagccga ccacggtgaa gctctggccc ggcaaagcgc ccggcgagac gaaggacatc     120
ggcccggaga agtatctcga aaccaagaag gggcagcttg acatcaagcg gctcaccaac     180
gtgagcgaac cgaccatcac gatctattcg ccgccaaagg agaaggcgaa cgacacagtg     240
gtgattgtcg cgcccggcgg cgggtacaac atcctcgcca tcgaacacga agggaccgat     300
gtctgcgagt ggctgaactc gctgggcgtg accgcggtgc tgctcaagta tcgcgtgccg     360
cggcgcccca tgcagtcgcc ggacaacctc gcgatgattc aggacgcgca gcgcgccatc     420
agtcttgttc gcagtatgca gaaagagttg ggcattcacc caacacgtgt gggaatgctc     480
ggcttttcgg ccggggggaa cctcaccgct tgcaccgcgt tggccgaaaa gcggatgtac     540
gagaacatcg acaaggtgga cgaggtattc aactgcacgc cgaacttcgc catcctcgtg     600
taccccgcgt atctcgtcga gaaggatgga acgctgcgcg ccgagttcaa agtgaagatc     660
gattcgccgc cgatgttctt cgtgcattcg tccgacgaca acgtgagcag tgaaaacagc     720
gtggcgcttt acctggcact caagaagaac aaggtgccgg cggaaatgca cctctacgcc     780
agcggcgggc acggctacgg aatgcgcaag gttccgcatc cgtgcgcaag ctggcccgac     840
cgcgccgcgg agtggatgaa agcacaccgg ctgcttgaga aggccaagcc cgagccgat     900 gggaagaagg agtaa                                                      915
```

```
<210> SEQ ID NO 2
<211> LENGTH: 304
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(20)

<400> SEQUENCE: 2

Met Ser Arg Val Cys Leu Pro Leu Thr Leu Thr Leu Ala Leu Thr Leu
1               5                   10                  15

Ser Ala Arg Ala Ala Glu Pro Thr Thr Val Lys Leu Trp Pro Gly Lys
            20                  25                  30

Ala Pro Gly Glu Thr Lys Asp Ile Gly Pro Glu Lys Tyr Leu Glu Thr
        35                  40                  45

Lys Lys Gly Gln Leu Asp Ile Lys Arg Leu Thr Asn Val Ser Glu Pro
50                  55                  60

Thr Ile Thr Ile Tyr Ser Pro Pro Lys Glu Lys Ala Asn Asp Thr Val
65                  70                  75                  80

Val Ile Val Ala Pro Gly Gly Tyr Asn Ile Leu Ala Ile Glu His
                85                  90                  95

Glu Gly Thr Asp Val Cys Glu Trp Leu Asn Ser Leu Gly Val Thr Ala
            100                 105                 110

Val Leu Leu Lys Tyr Arg Val Pro Arg Arg Pro Met Gln Ser Pro Asp
        115                 120                 125

Asn Leu Ala Met Ile Gln Asp Ala Gln Arg Ala Ile Ser Leu Val Arg
130                 135                 140

Ser Met Gln Lys Glu Leu Gly Ile His Pro Thr Arg Val Gly Met Leu
145                 150                 155                 160

Gly Phe Ser Ala Gly Gly Asn Leu Thr Ala Cys Thr Ala Leu Ala Glu
                165                 170                 175

Lys Arg Met Tyr Glu Asn Ile Asp Lys Val Asp Glu Val Phe Asn Cys
            180                 185                 190

Thr Pro Asn Phe Ala Ile Leu Val Tyr Pro Ala Tyr Leu Val Glu Lys
        195                 200                 205

Asp Gly Thr Leu Arg Ala Glu Phe Lys Val Lys Ile Asp Ser Pro Pro
210                 215                 220

Met Phe Phe Val His Ser Ser Asp Asn Val Ser Ser Glu Asn Ser
225                 230                 235                 240

Val Ala Leu Tyr Leu Ala Leu Lys Lys Asn Lys Val Pro Ala Glu Met
                245                 250                 255

His Leu Tyr Ala Ser Gly Gly His Gly Tyr Gly Met Arg Lys Val Pro
            260                 265                 270

His Pro Cys Ala Ser Trp Pro Asp Arg Ala Ala Glu Trp Met Lys Ala
        275                 280                 285

His Arg Leu Leu Glu Lys Ala Lys Pro Glu Pro Asp Gly Lys Glu
290                 295                 300

<210> SEQ ID NO 3
<211> LENGTH: 927
<212> TYPE: DNA
<213> ORGANISM: Unknown
<220> FEATURE:
<223> OTHER INFORMATION: Obtained from environmental sample
```

<400> SEQUENCE: 3

```
atgtcacttg atccacaaac gaaatttgta ttagcccaat tggctgctgc cgatgctcct    60
ccaatggaga ctttgtcacc ggaaatggct agacaggcat tcatattgcc gcaaggtgca   120
gtggaggaag tagggaaggt agaaaatcga acgattcctg gtcctgcaac ggacatccct   180
gtccgtgttt attaccctaa agaactccag cctgaaaatc ccgcgctagt tttctatcat   240
ggcggcggct gggtaattgg caatttggac tctcatgacg atatttgccg tgctttaacc   300
aacctcgcca actgcgtgac catttccgtc gactaccgcc tggctccaga gaataaattt   360
cctgctgcgg ttgaggatgc ttatgctgct gcacaatatg tgtatgacca tgcagaagat   420
ttcaaagtcg acaagacccg tattgccgtt ggcggtgaca gtgccggtgg aaatcttgcc   480
gctgtcgtga cgaatctggc aaaagacaaa aactcacctt ctatttgttt ccaacttctg   540
atttatccaa gcaccaatgc aggtggtgag ccaacagcat caatggttga atgcccat   600
ggctatttct tagaaaaagg cacgatggat tggttccgtg actgctacct gaacagtgaa   660
gaagacaaac agaatccgct agtctcaccg atgctttatg atgatttcca aggactgcct   720
ccagcaattg tgattactgc cgagtacgat ccattgcgag atgaaggcga agcatatgcc   780
aaaaagctgg gcgaagcagg ggttgctgtc caaaccatcc gctttgacgg tacgattcat   840
ggctttgtca gcatgtcggc tgtcattagc caagggaagg cggcattgga aaaagcagga   900
gaggctttaa ctaaagcctt tcaataa                                       927
```

<210> SEQ ID NO 4
<211> LENGTH: 308
<212> TYPE: PRT
<213> ORGANISM: Unknown
<220> FEATURE:
<223> OTHER INFORMATION: Obtained from environmental sample

<400> SEQUENCE: 4

```
Met Ser Leu Asp Pro Gln Thr Lys Phe Val Leu Ala Gln Leu Ala Ala
1               5                   10                  15

Ala Asp Ala Pro Pro Met Glu Thr Leu Ser Pro Glu Met Ala Arg Gln
            20                  25                  30

Ala Phe Ile Leu Pro Gln Gly Ala Val Glu Glu Val Gly Lys Val Glu
        35                  40                  45

Asn Arg Thr Ile Pro Gly Pro Ala Thr Asp Ile Pro Val Arg Val Tyr
    50                  55                  60

Tyr Pro Lys Glu Leu Gln Pro Glu Asn Pro Ala Leu Val Phe Tyr His
65                  70                  75                  80

Gly Gly Gly Trp Val Ile Gly Asn Leu Asp Ser His Asp Asp Ile Cys
                85                  90                  95

Arg Ala Leu Thr Asn Leu Ala Asn Cys Val Thr Ile Ser Val Asp Tyr
            100                 105                 110

Arg Leu Ala Pro Glu Asn Lys Phe Pro Ala Ala Val Glu Asp Ala Tyr
        115                 120                 125

Ala Ala Ala Gln Tyr Val Tyr Asp His Ala Glu Asp Phe Lys Val Asp
    130                 135                 140

Lys Thr Arg Ile Ala Val Gly Gly Asp Ser Ala Gly Gly Asn Leu Ala
145                 150                 155                 160

Ala Val Val Thr Asn Leu Ala Lys Asp Lys Asn Ser Pro Ser Ile Cys
                165                 170                 175
```

```
Phe Gln Leu Leu Ile Tyr Pro Ser Thr Asn Ala Gly Gly Glu Pro Thr
                180                 185                 190

Ala Ser Met Val Glu Asn Ala His Gly Tyr Phe Leu Glu Lys Gly Thr
            195                 200                 205

Met Asp Trp Phe Arg Asp Cys Tyr Leu Asn Ser Glu Glu Asp Lys Gln
        210                 215                 220

Asn Pro Leu Val Ser Pro Met Leu Tyr Asp Asp Phe Gln Gly Leu Pro
225                 230                 235                 240

Pro Ala Ile Val Ile Thr Ala Glu Tyr Asp Pro Leu Arg Asp Glu Gly
                245                 250                 255

Glu Ala Tyr Ala Lys Lys Leu Gly Glu Ala Gly Val Ala Val Gln Thr
            260                 265                 270

Ile Arg Phe Asp Gly Thr Ile His Gly Phe Val Ser Met Ser Ala Val
        275                 280                 285

Ile Ser Gln Gly Lys Ala Ala Leu Glu Lys Ala Gly Glu Ala Leu Thr
    290                 295                 300

Lys Ala Phe Gln
305

<210> SEQ ID NO 5
<211> LENGTH: 672
<212> TYPE: DNA
<213> ORGANISM: Unknown
<220> FEATURE:
<223> OTHER INFORMATION: Obtained from environmental sample

<400> SEQUENCE: 5
atgagaagaa ttgttttcct ttatattctg gcgttgctct gcgtatcctg tgcgaaccgg     60
aatccttctg tctcggaccc cgctccgtca ccgaccttgg gggagcaatc gtcagcgagt    120
ttaccgaaga tcgtagcatt cggcgacagc ctaactgctg gctttggtct ttcccagaat    180
gaaagttatc agcgcttttt gcaggaacga ctgagacagg acggttatga ttacgaagtg    240
atcaatgccg gagtttcagg cgataccagc gcgggcggtg tgcgtaggat cgactgggtt    300
ctggatgaga gcgtacgaat tctaattctt gaattgggtg ctaatgattt tcttcgtggc    360
catccagtag ctcagactaa gaaaaacctc gccgttatca tcgaacgtgc tcaggaaaaa    420
aacgtcaggg ttctgctagc agggatgttt gcaccgacga atactggatg ggagtaccag    480
gggcagatcc agcaaatgtt taacgatctt tcgcgagaaa aagccgtacc actaattcca    540
ttctttctcg agggagtagc cggcattcca actctgaatc tagctgatgg cattcatccc    600
aatgcggctg gcacaaagat cgttgctgag aatgtgtaca agtatctaaa accgatgctc    660
ccatctgatt aa                                                        672

<210> SEQ ID NO 6
<211> LENGTH: 223
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(25)
<220> FEATURE:
<221> NAME/KEY: DOMAIN
<222> LOCATION: (44)...(212)
<223> OTHER INFORMATION: GDSL-like Lipase/Acylhydrolase
```

<400> SEQUENCE: 6

```
Met Arg Arg Ile Val Phe Leu Tyr Ile Leu Ala Leu Leu Cys Val Ser
1               5                   10                  15
Cys Ala Asn Arg Asn Pro Ser Val Ser Asp Pro Ala Pro Ser Pro Thr
                20                  25                  30
Leu Gly Glu Gln Ser Ser Ala Ser Leu Pro Lys Ile Val Ala Phe Gly
            35                  40                  45
Asp Ser Leu Thr Ala Gly Phe Gly Leu Ser Gln Asn Glu Ser Tyr Pro
        50                  55                  60
Ala Leu Leu Gln Glu Arg Leu Arg Gln Asp Gly Tyr Asp Tyr Glu Val
65                  70                  75                  80
Ile Asn Ala Gly Val Ser Gly Asp Thr Ser Ala Gly Gly Val Arg Arg
                85                  90                  95
Ile Asp Trp Val Leu Asp Glu Ser Val Arg Ile Leu Ile Leu Glu Leu
            100                 105                 110
Gly Ala Asn Asp Phe Leu Arg Gly His Pro Val Ala Gln Thr Lys Lys
        115                 120                 125
Asn Leu Ala Val Ile Ile Glu Arg Ala Gln Glu Lys Asn Val Arg Val
130                 135                 140
Leu Leu Ala Gly Met Phe Ala Pro Thr Asn Thr Gly Trp Glu Tyr Gln
145                 150                 155                 160
Gly Gln Ile Gln Met Phe Asn Asp Leu Ser Arg Glu Lys Ala Val
                165                 170                 175
Pro Leu Ile Pro Phe Phe Leu Glu Gly Val Ala Gly Ile Pro Thr Leu
            180                 185                 190
Asn Leu Ala Asp Gly Ile His Pro Asn Ala Ala Gly Thr Lys Ile Val
        195                 200                 205
Ala Glu Asn Val Tyr Lys Tyr Leu Lys Pro Met Leu Pro Ser Asp
210                 215                 220
```

<210> SEQ ID NO 7
<211> LENGTH: 783
<212> TYPE: DNA
<213> ORGANISM: Unknown
<220> FEATURE:
<223> OTHER INFORMATION: Obtained from environmental sample

<400> SEQUENCE: 7

```
atgacacgaa aaaaaatcgg cttggcttta tccggcggcg cggcgcgtgg cttcgcacat      60
ctcggagttt tgaaagtttt cgccgaacac ggcattcccg tcgatttcgt cgccggaacg     120
agcgccggtt cgtttgcggg cgcggctttc gcttccggtt taagcgtggc ggaaatcatc     180
gaaatgtcaa ggaaaatcag ttggtttcgg atgaccggat tttcgtactc gccgaaaggc     240
ttgctgtcga acgcgccgat gggagcgttt atcaatcagc attttccgcg caaaaaattt     300
gaagaactgc cgataccgtt cgcggcaatt acgtgcgatc tcgaaaccgg cgaggaaatc     360
gtgcttaaag aaaccggcga cgtggcgact ccgtccgtg cgagctgcgc gctgcccggc     420
gtcttcgtgc aatcgaata cggcggacgg cgattgatag acggcggcgt cgtgtcgaac     480
gtgccgacga gagccgtcaa aaagctcggc gcggaaatca ttattgcggt tgacgttctg     540
gcgtgcggca aacttactg gggttcgcct ccactttgc tcggcatctt tttccaatcg     600
gcgatgatgc ttctccgcgc cgcttcaaaa tctcatcatt accgcgcgag cgtcgtcatc     660
acgccgcaaa tcgctcatct cgcccggac gaaatcagca aaatggacga atttatcaaa     720
```

-continued

```
gcgggcgaac aagccgcgct tgaaaaagtt gacgaaatca aggctttgct cgccgaacaa    780
taa                                                                   783
```

<210> SEQ ID NO 8
<211> LENGTH: 260
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (8)...(167)
<223> OTHER INFORMATION: Patatin-like phospholipase

<400> SEQUENCE: 8

```
Met Thr Arg Lys Lys Ile Gly Leu Ala Leu Ser Gly Gly Ala Ala Arg
1               5                   10                  15

Gly Phe Ala His Leu Gly Val Leu Lys Val Phe Ala Glu His Gly Ile
            20                  25                  30

Pro Val Asp Phe Val Ala Gly Thr Ser Ala Gly Ser Phe Ala Gly Ala
        35                  40                  45

Ala Phe Ala Ser Gly Leu Ser Val Ala Glu Ile Ile Glu Met Ser Arg
    50                  55                  60

Lys Ile Ser Trp Phe Arg Met Thr Gly Phe Ser Tyr Ser Pro Lys Gly
65                  70                  75                  80

Leu Leu Ser Asn Ala Pro Met Gly Ala Phe Ile Asn Gln His Phe Pro
                85                  90                  95

Arg Lys Lys Phe Glu Glu Leu Pro Ile Pro Phe Ala Ala Ile Thr Cys
            100                 105                 110

Asp Leu Glu Thr Gly Glu Glu Ile Val Leu Lys Glu Thr Gly Asp Val
        115                 120                 125

Ala Thr Ala Val Arg Ala Ser Cys Ala Leu Pro Gly Val Phe Val Pro
    130                 135                 140

Ile Glu Tyr Gly Gly Arg Arg Leu Ile Asp Gly Gly Val Val Ser Asn
145                 150                 155                 160

Val Pro Thr Arg Ala Val Lys Lys Leu Gly Ala Glu Ile Ile Ile Ala
                165                 170                 175

Val Asp Val Leu Ala Cys Gly Thr Thr Tyr Trp Gly Ser Pro Ser Thr
            180                 185                 190

Leu Leu Gly Ile Phe Phe Gln Ser Ala Met Met Leu Leu Arg Ala Ala
        195                 200                 205

Ser Lys Ser His His Tyr Arg Ala Ser Val Val Ile Thr Pro Gln Ile
    210                 215                 220

Ala His Leu Arg Pro Asp Glu Ile Ser Lys Met Asp Glu Phe Ile Lys
225                 230                 235                 240

Ala Gly Glu Gln Ala Ala Leu Glu Lys Val Asp Glu Ile Lys Ala Leu
                245                 250                 255

Leu Ala Glu Gln
            260
```

<210> SEQ ID NO 9
<211> LENGTH: 849
<212> TYPE: DNA
<213> ORGANISM: Unknown
<220> FEATURE:
<223> OTHER INFORMATION: Obtained from environmental sample

<400> SEQUENCE: 9

```
atgttcaaca aagcacttcc tgcagcggcc gcggtcgccg gtctgttcct ttccacctcg    60
gccatggcgc tgctgccgga tacgcccgga accccctccc cgtcggtgtc cagcttcgaa   120
aggtccggtc cctacagcac caccagccgc agcgaaggcc ccaactgccg gatctatcga   180
ccgagcaacc tgggccagaa cggcgtccgc caccggtca tcctctgggg caacggcacc   240
ggtgccagcc cgaccaccta ccgcggcctg ctcgagcact gggccagcca cggcttcgtg   300
gtcgccgccg ccgagaccte caacgccggc tccgggcgcg agatgctcaa ctgcctgagc   360
tacctgcaga ccgaagccgg cgcagcagc ggcacctacg tcggccggct caatctcggc   420
cgcgtcggca cgtccggcca ctcgcagggc ggtggcggct cgatcatggc cgggcgcgac   480
acccggatca aaaccaccgc gcccatgcag ccctacaccc tgggcctggg ccatgtgagt   540
tcctcgcaga gccagcagaa cggccgatg ttcctgatgt ccggcagcct ggacaccctg   600
gccggcccga ccctgaacca ggcgccggtc tatcgccggg ccaacgtgcc ggtgttctgg   660
ggcaccctgc gcggcgccag ccacttcgtg ccggtcggca gtgccggcgg ttaccgtggc   720
ccgtccaccg cctggttccg ctaccagctg atggacgata cctcggcgcg cagccagttc   780
gtcggcacca actgcggcct gtgccgcgac ttctcctgga ccgacatcca gcgcaagggc   840
gcgctgtaa                                                          849
```

<210> SEQ ID NO 10
<211> LENGTH: 282
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(23)

<400> SEQUENCE: 10

```
Met Phe Asn Lys Ala Leu Pro Ala Ala Ala Val Ala Gly Leu Phe
1               5                   10                  15

Leu Ser Thr Ser Ala Met Ala Leu Leu Pro Asp Thr Pro Gly Thr Pro
                20                  25                  30

Phe Pro Ser Val Ser Ser Phe Glu Arg Ser Gly Pro Tyr Ser Thr Thr
            35                  40                  45

Ser Arg Ser Glu Gly Pro Asn Cys Arg Ile Tyr Arg Pro Ser Asn Leu
        50                  55                  60

Gly Gln Asn Gly Val Arg His Pro Val Ile Leu Trp Gly Asn Gly Thr
65                  70                  75                  80

Gly Ala Ser Pro Thr Thr Tyr Arg Gly Leu Leu Glu His Trp Ala Ser
                85                  90                  95

His Gly Phe Val Val Ala Ala Ala Glu Thr Ser Asn Ala Gly Ser Gly
            100                 105                 110

Arg Glu Met Leu Asn Cys Leu Ser Tyr Leu Gln Thr Glu Ala Gly Arg
        115                 120                 125

Ser Ser Gly Thr Tyr Val Gly Arg Leu Asn Leu Gly Arg Val Gly Thr
    130                 135                 140

Ser Gly His Ser Gln Gly Gly Gly Ser Ile Met Ala Gly Arg Asp
145                 150                 155                 160

Thr Arg Ile Lys Thr Thr Ala Pro Met Gln Pro Tyr Thr Leu Gly Leu
                165                 170                 175
```

```
Gly His Val Ser Ser Gln Ser Gln Gln Asn Gly Pro Met Phe Leu
            180                 185                 190

Met Ser Gly Ser Leu Asp Thr Leu Ala Gly Pro Thr Leu Asn Gln Ala
        195                 200                 205

Pro Val Tyr Arg Arg Ala Asn Val Pro Val Phe Trp Gly Thr Leu Arg
    210                 215                 220

Gly Ala Ser His Phe Val Pro Val Gly Ser Ala Gly Gly Tyr Arg Gly
225                 230                 235                 240

Pro Ser Thr Ala Trp Phe Arg Tyr Gln Leu Met Asp Asp Thr Ser Ala
            245                 250                 255

Arg Ser Gln Phe Val Gly Thr Asn Cys Gly Leu Cys Arg Asp Phe Ser
        260                 265                 270

Trp Thr Asp Ile Gln Arg Lys Gly Ala Leu
            275                 280

<210> SEQ ID NO 11
<211> LENGTH: 672
<212> TYPE: DNA
<213> ORGANISM: Unknown
<220> FEATURE:
<223> OTHER INFORMATION: Obtained from environmental sample

<400> SEQUENCE: 11
gtgtccgccc ccgaagccgc gagcgtggag catgcggacc ccggcggggt cgccaccctg      60
gcggaacgcc ccgcggcgcg tccgcgcatc gtcttcctgg cgacagcct gaccgccggg     120 tacggactgg cgcgggagca gtccgtgccc gcgctactcc agcggcggct cgaccgggag     180
gggtatgagt acgaagtcgt caatgcgggc gtctcgggcg acacgtccgc cggcgggctg     240
agccggctcg actggtcgct cgacggcgag gtcgccctgc tggtggtgga gctcggcgcc     300
aacgacgggc tgcgcggcct gcccgtgtcc gcgatgaagc gcaacctgga cgccatcatc     360
acgcgcgccc gcgcgcgggg catcaccgtg gtgctcgccg gcatggaagc gccgccgaac     420
tacggcgcgg cctacacgac cgagttccgg caggcgtttc acgatctcgc ccgtacccac     480
gacgtgccgt tcgtgccgtt ctttctcgaa ggggtagccg gcctgccgca cctcaacatc     540
gccgacggca tccatcccaa cgccgagggc gcgcgcgtgg tcgaggccaa cgtctggcag     600
gtgctggaac cgttactcga cgagcctggc cgggcggccg cctcgcgcgc gcagcccgcg     660
gatggccgct ga                                                        672

<210> SEQ ID NO 12
<211> LENGTH: 223
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (30)...(198)
<223> OTHER INFORMATION: GDSL-like Lipase/Acylhydrolase

<400> SEQUENCE: 12

Met Ser Ala Pro Glu Ala Ala Ser Val Glu His Ala Asp Pro Gly Gly
1               5                   10                  15

Val Ala Thr Leu Ala Glu Arg Pro Ala Ala Arg Pro Arg Ile Val Phe
            20                  25                  30

Leu Gly Asp Ser Leu Thr Ala Gly Tyr Gly Leu Ala Arg Glu Gln Ser
        35                  40                  45
```

Val Pro Ala Leu Leu Gln Arg Arg Leu Asp Arg Glu Gly Tyr Glu Tyr
    50                  55                  60

Glu Val Val Asn Ala Gly Val Ser Gly Asp Thr Ser Ala Gly Gly Leu
65                  70                  75                  80

Ser Arg Leu Asp Trp Ser Leu Asp Gly Glu Val Ala Leu Leu Val Val
                85                  90                  95

Glu Leu Gly Ala Asn Asp Gly Leu Arg Gly Leu Pro Val Ser Ala Met
            100                 105                 110

Lys Arg Asn Leu Asp Ala Ile Ile Thr Arg Ala Arg Ala Arg Gly Ile
                115                 120                 125

Thr Val Val Leu Ala Gly Met Glu Ala Pro Pro Asn Tyr Gly Ala Ala
    130                 135                 140

Tyr Thr Thr Glu Phe Arg Gln Ala Phe His Asp Leu Ala Arg Thr His
145                 150                 155                 160

Asp Val Pro Phe Val Pro Phe Phe Leu Glu Gly Val Ala Gly Leu Pro
                165                 170                 175

His Leu Asn Ile Ala Asp Gly Ile His Pro Asn Ala Glu Gly Ala Arg
            180                 185                 190

Val Val Glu Ala Asn Val Trp Gln Val Leu Glu Pro Leu Leu Asp Glu
                195                 200                 205

Pro Gly Arg Ala Ala Ala Ser Arg Ala Gln Pro Ala Asp Gly Arg
    210                 215                 220

<210> SEQ ID NO 13
<211> LENGTH: 900
<212> TYPE: DNA
<213> ORGANISM: Unknown
<220> FEATURE:
<223> OTHER INFORMATION: Obtained from environmental sample

<400> SEQUENCE: 13
atgaaggcaa gctgccgcga catcgaaatc gaatacgaaa cattcggcca tccggacgac      60
ccggccatcg tgctgatcat gggactcggt ggccagctca tcctgtggcc ggaagcgttc     120
tgccgcatgc tggccgacgc tggtcactac gtggtgcgct cgacaaccg cgacatcggc      180 ctgtcgacga tctcgatca ccttccccgc cccaacctgc cgctcgccgc gctccgccag      240
gcgctgcgcc tgccagttcg cgccagttac acgctcgacg acatggcgga cgacgtcgcg     300
ggcctgcttg atgcactgaa catcaagcag gcgcacgtcg tcggcgtgtc gatgggcggc     360
atgatcgccc agctgctggc cgcacggcac gcgacccgcg tgcgcagcct gaccttgctg     420
atgaccacca gcggcgcgcg caacgttccg ggcccctcac tcggcatgcg catggaaatg     480
atccgtcgac cgcgcgacac ctcgcgcgag gggctgatcc gccatggtat gcgtacctgg     540
cggatcatcg gcagcccgac gtacccgaag ccggaagccg aactgcgccg catcgtcgcc     600
gagggctttg accgcgcgtt tcacccggcc ggtttcatgc ccagctgca cgccgttctc      660 gcggcaccga gccgcgcacc cctgctgccg cgcatcaaac agccggccga cgtcattcac     720
ggcgacgccg acctgctggt accagtggca gcggcacgtg atctggtgcg ccgcctgccg     780
aacgccacgc tcgacatcgt gccgggcatg gggcatgact cccgaccga gatcatgccg      840 cgtatcgcgc gccgcattgt cgaaaccgcg gcacgcgacc cgcagcggct cgccgcctag     900

<210> SEQ ID NO 14
<211> LENGTH: 299
<212> TYPE: PRT
<213> ORGANISM: Unknown

<220> FEATURE:
<223> OTHER INFORMATION: Obtained from environmental sample
<220> FEATURE:
<221> NAME/KEY: DOMAIN
<222> LOCATION: (49)...(288)
<223> OTHER INFORMATION: alpha/beta hydrolase fold

<400> SEQUENCE: 14

```
Met Lys Ala Ser Cys Arg Asp Ile Glu Ile Glu Tyr Glu Thr Phe Gly
1               5                   10                  15

His Pro Asp Asp Pro Ala Ile Val Leu Ile Met Gly Leu Gly Gly Gln
            20                  25                  30

Leu Ile Leu Trp Pro Glu Ala Phe Cys Arg Met Leu Ala Asp Ala Gly
        35                  40                  45

His Tyr Val Val Arg Phe Asp Asn Arg Asp Ile Gly Leu Ser Thr His
    50                  55                  60

Leu Asp His Leu Pro Arg Pro Asn Leu Pro Leu Ala Ala Leu Arg Gln
65                  70                  75                  80

Ala Leu Arg Leu Pro Val Arg Ala Ser Tyr Thr Leu Asp Asp Met Ala
                85                  90                  95

Asp Asp Val Ala Gly Leu Leu Asp Ala Leu Asn Ile Lys Gln Ala His
            100                 105                 110

Val Val Gly Val Ser Met Gly Gly Met Ile Ala Gln Leu Leu Ala Ala
        115                 120                 125

Arg His Ala Thr Arg Val Arg Ser Leu Thr Leu Leu Met Thr Thr Ser
    130                 135                 140

Gly Ala Arg Asn Val Pro Gly Pro Ser Leu Gly Met Arg Met Glu Met
145                 150                 155                 160

Ile Arg Arg Pro Arg Asp Thr Ser Arg Glu Gly Leu Ile Arg His Gly
                165                 170                 175

Met Arg Thr Trp Arg Ile Ile Gly Ser Pro Thr Tyr Pro Lys Pro Glu
            180                 185                 190

Ala Glu Leu Arg Arg Ile Val Ala Glu Gly Phe Asp Arg Ala Phe His
        195                 200                 205

Pro Ala Gly Phe Met Arg Gln Leu His Ala Val Leu Ala Ala Pro Ser
    210                 215                 220

Arg Ala Pro Leu Leu Pro Arg Ile Lys Gln Pro Ala Asp Val Ile His
225                 230                 235                 240

Gly Asp Ala Asp Leu Leu Val Pro Val Ala Ala Arg Asp Leu Val
                245                 250                 255

Arg Arg Leu Pro Asn Ala Thr Leu Asp Ile Val Pro Gly Met Gly His
            260                 265                 270

Asp Phe Pro Thr Glu Ile Met Pro Arg Ile Ala Arg Ile Val Glu
        275                 280                 285

Thr Ala Ala Arg Asp Pro Gln Arg Leu Ala Ala
    290                 295
```

<210> SEQ ID NO 15
<211> LENGTH: 759
<212> TYPE: DNA
<213> ORGANISM: Unknown
<220> FEATURE:
<223> OTHER INFORMATION: Obtained from environmental sample

<400> SEQUENCE: 15
atgggcaaac aaatgcctta tagagtgatt tttccagtaa actaccaaac ttccaaaaaa    60
cgctatccag tgatttacct tctgcacggc ctttcgggca attacaaaaa ctggaccgag   120

-continued

```
aaaaccaaat tgacaaaata tgcaaccgaa tacaacttct tgattatcac agttgaaggc     180
gagaacggtt ggtattctga cagtaaaatc aaacctaaca ggctttacga aagctacata     240
atccaggaac tgatacctga agttgataaa aagtttcgca caatagcaga tcgcaatcac     300
agagctatcg caggtctttc gatgggtggt tacggtgcga taagtttgg cttgaaatat     360 cctgaaaaat tcgctttgat tgggtccttt agcggcgctc ttgcggcaac ttcaatcaag     420
gaaggcacag cgcttgagtg gattacaaaa accatcaatg atgctttcgg tcctgaagga     480
agcgaatcca gaaagaaaa cgatattttc cagattgcgc gcgacctgaa tgatgaacaa     540
ataaagaaac ttccctttat ttactttgat tgcggaaccg aagattttct gttcaaagac     600
aatcaggatt tcatgaaact acttgttgaa aagagaatca acacgaata tagacaaaag     660 cccggcaccc atacgtggga atactgggat agccaaataa aagaattctt gggtttagcc     720
aacaaattta tagaaaaaac tgctttatgg cgatactaa                           759
```

<210> SEQ ID NO 16
<211> LENGTH: 252
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (1)...(240)
<223> OTHER INFORMATION: Putative esterase

<400> SEQUENCE: 16

```
Met Gly Lys Gln Met Pro Tyr Arg Val Ile Phe Pro Val Asn Tyr Gln
1               5                   10                  15

Thr Ser Lys Lys Arg Tyr Pro Val Ile Tyr Leu Leu His Gly Leu Ser
            20                  25                  30

Gly Asn Tyr Lys Asn Trp Thr Glu Lys Thr Lys Leu Thr Lys Tyr Ala
        35                  40                  45

Thr Glu Tyr Asn Phe Leu Ile Ile Thr Val Glu Gly Glu Asn Gly Trp
    50                  55                  60

Tyr Ser Asp Ser Lys Ile Lys Pro Asn Arg Leu Tyr Glu Ser Tyr Ile
65                  70                  75                  80

Ile Gln Glu Leu Ile Pro Glu Val Asp Lys Lys Phe Arg Thr Ile Ala
                85                  90                  95

Asp Arg Asn His Arg Ala Ile Ala Gly Leu Ser Met Gly Gly Tyr Gly
            100                 105                 110

Ala Ile Lys Phe Gly Leu Lys Tyr Pro Glu Lys Phe Ala Leu Ile Gly
        115                 120                 125

Ser Phe Ser Gly Ala Leu Ala Ala Thr Ser Ile Lys Glu Gly Thr Ala
    130                 135                 140

Leu Glu Trp Ile Thr Lys Thr Ile Asn Asp Ala Phe Gly Pro Glu Gly
145                 150                 155                 160

Ser Glu Ser Arg Lys Glu Asn Asp Ile Phe Gln Ile Ala Arg Asp Leu
                165                 170                 175

Asn Asp Glu Gln Ile Lys Lys Leu Pro Phe Ile Tyr Phe Asp Cys Gly
            180                 185                 190

Thr Glu Asp Phe Leu Phe Lys Asp Asn Gln Asp Phe Met Lys Leu Leu
        195                 200                 205
```

Val Glu Lys Arg Ile Lys His Glu Tyr Arg Gln Lys Pro Gly Thr His
210                 215                 220

Thr Trp Glu Tyr Trp Asp Ser Gln Ile Lys Glu Phe Leu Gly Leu Ala
225                 230                 235                 240

Asn Lys Phe Ile Glu Lys Thr Ala Leu Trp Arg Tyr
                245                 250

<210> SEQ ID NO 17
<211> LENGTH: 753
<212> TYPE: DNA
<213> ORGANISM: Unknown
<220> FEATURE:
<223> OTHER INFORMATION: Obtained from environmental sample

<400> SEQUENCE: 17

```
atgaaaaagt ataaaacagg cctggtttta agtggtggcg aacacgtgg ttttgcgcat      60
ctgggagtga tagcagctct ttacgataag ggaattaaac ccgacataat ttcgggtaca    120
agtgctggtg ccattgttgg cgcttttatt gctgccggga aaaatccaca cgacgttgtg    180
gagatttta aaagggatc gttttcaat tacacaaaac tacagatacc ccgcgacggt      240
ttgatgaaac tggatggact gaaggaattg tttcaaaagg aaattcatgt aaaaaacctc    300
gaagagcttg aaatcccct ttttattgcc atttcgaatt taaataaagg aaccgtggaa    360
tacagaaata gcggtctttt gggtgaaact gtgcttgcct catcttcgat ccccatactt    420
tttgctccgg ttttaatcgg cgacgatttg tatgttgacg ggggattaat ggataacatt    480
ccggttgaac ccatcaaact cgattgtgaa caaatcattg tttcaaatat cagtccgatt    540
aatcccgttg aaaaaattaa aaatctgatt cacattgcta ctcgtacttt ttatatgagt    600
gtaaacgcca acatgaaaca ggttaaaaaa tattccaccc attatattga accggacgga    660
atagatactt acgaaatttt aagccgcacc cacgccgatg agttgtatga acttggatat    720
aattcgacaa ttaaaatcct gaattcgcac taa                                753
```

<210> SEQ ID NO 18
<211> LENGTH: 250
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (8)...(166)
<223> OTHER INFORMATION: Patatin-like phospholipase

<400> SEQUENCE: 18

Met Lys Lys Tyr Lys Thr Gly Leu Val Leu Ser Gly Gly Thr Arg
1               5                   10                  15

Gly Phe Ala His Leu Gly Val Ile Ala Ala Leu Tyr Asp Lys Gly Ile
                20                  25                  30

Lys Pro Asp Ile Ile Ser Gly Thr Ser Ala Gly Ala Ile Val Gly Ala
            35                  40                  45

Phe Ile Ala Ala Gly Lys Asn Pro His Asp Val Val Glu Ile Phe Lys
    50                  55                  60

Lys Gly Ser Phe Phe Asn Tyr Thr Lys Leu Gln Ile Pro Arg Asp Gly
65                  70                  75                  80

Leu Met Lys Leu Asp Gly Leu Lys Glu Leu Phe Gln Lys Glu Ile His
                85                  90                  95

Val Lys Asn Leu Glu Glu Leu Glu Ile Pro Leu Phe Ile Ala Ile Ser
            100                 105                 110

```
Asn Leu Asn Lys Gly Thr Val Glu Tyr Arg Asn Ser Gly Leu Leu Gly
            115                 120                 125

Glu Thr Val Leu Ala Ser Ser Ile Pro Ile Leu Phe Ala Pro Val
    130                 135                 140

Leu Ile Gly Asp Asp Leu Tyr Val Asp Gly Gly Leu Met Asp Asn Ile
145                 150                 155                 160

Pro Val Glu Pro Ile Lys Leu Asp Cys Glu Gln Ile Ile Val Ser Asn
                165                 170                 175

Ile Ser Pro Ile Asn Pro Val Glu Lys Ile Lys Asn Leu Ile His Ile
            180                 185                 190

Ala Thr Arg Thr Phe Tyr Met Ser Val Asn Ala Asn Met Lys Gln Val
        195                 200                 205

Lys Lys Tyr Ser Thr His Tyr Ile Glu Pro Asp Gly Ile Asp Thr Tyr
    210                 215                 220

Glu Ile Leu Ser Arg Thr His Ala Asp Glu Leu Tyr Glu Leu Gly Tyr
225                 230                 235                 240

Asn Ser Thr Ile Lys Ile Leu Asn Ser His
            245                 250
```

<210> SEQ ID NO 19
<211> LENGTH: 1071
<212> TYPE: DNA
<213> ORGANISM: Unknown
<220> FEATURE:
<223> OTHER INFORMATION: Obtained from environmental sample

<400> SEQUENCE: 19

```
atgggtgcga ataatccggt cacaaaattt gtaatggata aggggcaggg cactgcagca        60
cgtttgctgg attgcctgcc gagctttgca caagaacgtc tggtaaaagc attggattat       120
ccttatgact atcctgattt ggatccttat ataaaatgct tgatggcgat tcagattaaa       180
cagggagagc acagttttat tagtgcagat gcggtgcagt cacgtcaact gtttgatgaa       240
cgcatgaaag ctattcaggc gaaaccgacg ccggtcaagg cagtcgagga tctgcgtttg       300
ccattgcaaa atggcactat ctttgcccga cattatcatc cggcaccaca gaaaaaattg       360
ccgatggtca ttttctatca tggtggtgca tttatagtgg gtggtctgga tacgcatgat       420
gagttctgcc gtttattggc ggtgcatgcc aaggtgcagg tactcagcgt ggcttatccg       480
ctaacgcccg aatacagtcc tttgcagatg gtacaggtct gtgaagatgc tctggcttgg       540
gtacatcaaa acatcaagca gttgaaaatc tataaaaacc agattgtagt ggcaggggat       600
agtgcaggtg gaaatctggc ggcagtggtt gcgcagcgga gtgccgataa aatctatgca       660
cctcgcgcac agttattgct ttacccggct gtcgatttta aaagccgcca tccttctttt       720
tatgcataca atcagggcct ggtactttca gctcaggata ttgatctggt gaccaagcta       780
tatgctgaaa cacatcaggt cgaactggat gatccgctga tttcaccgac ctatggtgaa       840
ctgaagaatc tgccgcctgc ctatgtgatt accgcccgtc atgatgtgtt gcatgatgag       900
ggttcaatct atgcgctgaa gttacgtgag aatggggtgc gagtgtatta tcaggagtat       960
acggatcagg cccacggttt tatcaatctg accccaattc ataaacgttc gaaaaagcag      1020
gtcattgaac tcagcaagaa tttccgtaaa ttcctggata aaaagatctg a               1071
```

<210> SEQ ID NO 20
<211> LENGTH: 356
<212> TYPE: PRT
<213> ORGANISM: Unknown

<220> FEATURE:
<223> OTHER INFORMATION: Obtained from environmental sample

<400> SEQUENCE: 20

```
Met Gly Ala Asn Asn Pro Val Thr Lys Phe Val Met Asp Lys Gly Gln
1               5                   10                  15

Gly Thr Ala Ala Arg Leu Leu Asp Cys Leu Pro Ser Phe Ala Gln Glu
            20                  25                  30

Arg Leu Val Lys Ala Leu Asp Tyr Pro Tyr Asp Tyr Pro Asp Leu Asp
        35                  40                  45

Pro Tyr Ile Lys Cys Leu Met Ala Ile Gln Ile Lys Gln Gly Glu His
    50                  55                  60

Ser Phe Ile Ser Ala Asp Ala Val Gln Ser Arg Gln Leu Phe Asp Glu
65                  70                  75                  80

Arg Met Lys Ala Ile Gln Ala Lys Pro Thr Pro Val Lys Ala Val Glu
                85                  90                  95

Asp Leu Arg Leu Pro Leu Gln Asn Gly Thr Ile Phe Ala Arg His Tyr
            100                 105                 110

His Pro Ala Pro Gln Lys Lys Leu Pro Met Val Ile Phe Tyr His Gly
        115                 120                 125

Gly Ala Phe Ile Val Gly Gly Leu Asp Thr His Asp Glu Phe Cys Arg
    130                 135                 140

Leu Leu Ala Val His Ala Lys Val Gln Val Leu Ser Val Ala Tyr Pro
145                 150                 155                 160

Leu Thr Pro Glu Tyr Ser Pro Leu Gln Met Val Gln Val Cys Glu Asp
                165                 170                 175

Ala Leu Ala Trp Val His Gln Asn Ile Lys Gln Leu Lys Ile Tyr Lys
            180                 185                 190

Asn Gln Ile Val Val Ala Gly Asp Ser Ala Gly Gly Asn Leu Ala Ala
        195                 200                 205

Val Val Ala Gln Arg Ser Ala Asp Lys Ile Tyr Ala Pro Arg Ala Gln
    210                 215                 220

Leu Leu Leu Tyr Pro Ala Val Asp Phe Lys Ser Arg His Pro Ser Phe
225                 230                 235                 240

Tyr Ala Tyr Asn Gln Gly Leu Val Leu Ser Ala Gln Asp Ile Asp Leu
                245                 250                 255

Val Thr Lys Leu Tyr Ala Glu Thr His Gln Val Glu Leu Asp Asp Pro
            260                 265                 270

Leu Ile Ser Pro Thr Tyr Gly Glu Leu Lys Asn Leu Pro Pro Ala Tyr
        275                 280                 285

Val Ile Thr Ala Arg His Asp Val Leu His Asp Glu Gly Ser Ile Tyr
    290                 295                 300

Ala Leu Lys Leu Arg Glu Asn Gly Val Arg Val Tyr Tyr Gln Glu Tyr
305                 310                 315                 320

Thr Asp Gln Ala His Gly Phe Ile Asn Leu Thr Pro Ile His Lys Arg
                325                 330                 335

Ser Lys Lys Gln Val Ile Glu Leu Ser Lys Asn Phe Arg Lys Phe Leu
            340                 345                 350

Asp Lys Lys Ile
        355
```

<210> SEQ ID NO 21
<211> LENGTH: 1127
<212> TYPE: DNA
<213> ORGANISM: Arabidopsis thaliana -continued

```
<400> SEQUENCE: 21
aaaaaaagta aagaaaagaa aaactaataa agaacaaaaa aaatgtcctc ttcttcatca      60
agaaacgcct ttgaagatgg caaatacaaa tcaaatctct taaccttgga ctcatcatct     120
cgttgctgca aaataacacc gtcttctaga gcttcaccgt ctccgccaaa gcagctgttg     180
gtggctacgc cggtggagga aggagattat ccggtggtga tgctcctcca tggttacctt     240
ctctacaact cctttctattc tcagcttatg ttgcatgtct cttctcatgg cttcatcctc    300
atcgctcctc agttatatag tatcgccgga ccagacacaa tggatgagat taaatcaacg     360
gcggagatta tggattggtt atcagtagga cttaatcact ttcttccagc gcaagtaaca     420
ccaaacctat ccaaatttgc cctctccggc catagccgcg gtggcaaaac cgcgtttgcg     480
gtcgccttaa agaaatttgg gtactcctcg aatctaaaga tctcgacatt gatcggtata     540
gatccagtcg atggaacagg gaaagggaaa caaaccccctc ctccggtgtt ggcttacctt    600
ccaaactcat ttgacctaga caaaacgcct atacttgtga tcggttcggg gcttggtgaa     660
accgctcgga acccattatt cccaccgtgt gcacctcccg gagtgaatca ccgagagttc     720
tttcgggaat gtcaaggtcc agcatggcat ttcgttgcga aggattatgg gcatttggac     780
atgcttgatg atgatacaaa agggattaga gggaagagtt cttattgttt gtgtaagaat     840
ggtgaagaga ggagaccaat gaggagattc gttggtggac ttgttgtatc attttttgaag   900
gcttatttgg aaggagatga tcgtgaatta gttaagatca agatgggtg tcacgaggat     960
gttcccgttg aaattcaaga gtttgaggtt atcatgtaaa cataagttttt tctttagggg   1020
ctggttttc tattgtcaat atcatcagct tttgttgctt atggttttac aaacttatat    1080
tgtacaactc tttaagtcac ctctttgctt atgatattaa cccgatc                 1127

<210> SEQ ID NO 22
<211> LENGTH: 318
<212> TYPE: PRT
<213> ORGANISM: Arabidopsis thaliana

<400> SEQUENCE: 22

Met Ser Ser Ser Ser Arg Asn Ala Phe Glu Asp Gly Lys Tyr Lys
1               5                   10                  15

Ser Asn Leu Leu Thr Leu Asp Ser Ser Arg Cys Cys Lys Ile Thr
                20                  25                  30

Pro Ser Ser Arg Ala Ser Pro Ser Pro Lys Gln Leu Leu Val Ala
            35                  40                  45

Thr Pro Val Glu Glu Gly Asp Tyr Pro Val Val Met Leu Leu His Gly
        50                  55                  60

Tyr Leu Leu Tyr Asn Ser Phe Tyr Ser Gln Leu Met Leu His Val Ser
65                  70                  75                  80

Ser His Gly Phe Ile Leu Ile Ala Pro Gln Leu Tyr Ser Ile Ala Gly
                85                  90                  95

Pro Asp Thr Met Asp Glu Ile Lys Ser Thr Ala Glu Ile Met Asp Trp
            100                 105                 110

Leu Ser Val Gly Leu Asn His Phe Leu Pro Ala Gln Val Thr Pro Asn
        115                 120                 125

Leu Ser Lys Phe Ala Leu Ser Gly His Ser Arg Gly Gly Lys Thr Ala
    130                 135                 140

Phe Ala Val Ala Leu Lys Lys Phe Gly Tyr Ser Ser Asn Leu Lys Ile
145                 150                 155                 160
```

-continued

```
Ser Thr Leu Ile Gly Ile Asp Pro Val Asp Gly Thr Gly Lys Gly Lys
            165                 170                 175

Gln Thr Pro Pro Pro Val Leu Ala Tyr Leu Pro Asn Ser Phe Asp Leu
        180                 185                 190

Asp Lys Thr Pro Ile Leu Val Ile Gly Ser Gly Leu Gly Glu Thr Ala
    195                 200                 205

Arg Asn Pro Leu Phe Pro Pro Cys Ala Pro Pro Gly Val Asn His Arg
210                 215                 220

Glu Phe Phe Arg Glu Cys Gln Gly Pro Ala Trp His Phe Val Ala Lys
225                 230                 235                 240

Asp Tyr Gly His Leu Asp Met Leu Asp Asp Thr Lys Gly Ile Arg
            245                 250                 255

Gly Lys Ser Ser Tyr Cys Leu Cys Lys Asn Gly Glu Glu Arg Arg Pro
            260                 265                 270

Met Arg Arg Phe Val Gly Gly Leu Val Val Ser Phe Leu Lys Ala Tyr
        275                 280                 285

Leu Glu Gly Asp Asp Arg Glu Leu Val Lys Ile Lys Asp Gly Cys His
        290                 295                 300

Glu Asp Val Pro Val Glu Ile Gln Glu Phe Glu Val Ile Met
305                 310                 315
```

<210> SEQ ID NO 23
<211> LENGTH: 1157
<212> TYPE: DNA
<213> ORGANISM: Ginkgo biloba

<400> SEQUENCE: 23

| | | | | | |
|---|---|---|---|---|---|
| ttgaaaaaca | aaaacgaaga | agatgaactc | agtacttgca | cacagccatc | ggccatggtt | 60 |
| ttagtgaagg | atgtgttcag | cgaaggtcct | ttacctgttc | aaatcctcgc | aattccacaa | 120 |
| gccaactcat | ctccatgctc | aaaattagca | gacaaaaacg | gaactgcaac | cacgccttct | 180 |
| ccttgtcggc | ctcctaaacc | cctgctgatc | gctcttcctt | cccaacatgg | agattatcct | 240 |
| ctcatcctct | ttttccacgg | ctatgtactc | ctcaattcct | tctattctca | actcttgcgc | 300 |
| catgttgctt | cccatggata | catcgccata | gctcctcaga | tgtacagtgt | aattggccca | 360 |
| aatacgactc | cagaaatagc | cgatgcagcg | gccattacag | actggttacg | agatggactc | 420 |
| tcggataatc | ttccgcaagc | tttaaacaat | catgtgaggc | ccaattttga | gaaatttgtg | 480 |
| ctagcgggc | actcgcgcgg | gggtaaagtg | gcatttgcac | ttgccctagg | tcgagtctcg | 540 |
| cagccatctt | taaagtactc | ggcccttgta | ggtcttgatc | cagtcgatgg | aatgggaaaa | 600 |
| gatcaacaaa | ccagtcatcc | tattctgtca | tacagagagc | attcctttga | tttgggtatg | 660 |
| ccaacattag | tggtaggttc | gggcctgggt | ccgtgcaaaa | gaaaccctct | cttccctccc | 720 |
| tgtgctcccc | aaggtgttaa | ccaccatgat | ttcttctacg | aatgtgtcgc | tcctgcctat | 780 |
| cattttgttg | cctctgatta | tgggcatctt | gatttcttag | acgacgacac | caaaggaata | 840 |
| agaggaaagg | ctacttattg | cctctgtaag | aatggggaag | caagagagcc | aatgcggaag | 900 |
| tttagcggtg | gaattgtggt | tgcatttctt | caagcatttc | ttggtgataa | tcgtggagcc | 960 |
| ctgaatgata | ttatggttta | tccttcacat | gctccagtca | agattgagcc | tccagagtct | 1020 |
| ttggttacag | aagatgtaaa | atccccagaa | gtcgaattat | acgccgggc | agtttgcaga | 1080 |
| tgatgtacca | tggtattatg | cattaaagga | atgtatttgt | tattaaaaaa | atattaagaa | 1140 |
| gtaaaaaaaa | aaaaaaa | | | | | 1157 |

```
<210> SEQ ID NO 24
<211> LENGTH: 342
<212> TYPE: PRT
<213> ORGANISM: Ginkgo biloba

<400> SEQUENCE: 24

Met Val Leu Val Lys Asp Val Phe Ser Glu Gly Pro Leu Pro Val Gln
1               5                   10                  15

Ile Leu Ala Ile Pro Gln Ala Asn Ser Ser Pro Cys Ser Lys Leu Ala
            20                  25                  30

Asp Lys Asn Gly Thr Ala Thr Thr Pro Ser Pro Cys Arg Pro Pro Lys
        35                  40                  45

Pro Leu Leu Ile Ala Leu Pro Ser Gln His Gly Asp Tyr Pro Leu Ile
    50                  55                  60

Leu Phe Phe His Gly Tyr Val Leu Leu Asn Ser Phe Tyr Ser Gln Leu
65                  70                  75                  80

Leu Arg His Val Ala Ser His Gly Tyr Ile Ala Ile Ala Pro Gln Met
                85                  90                  95

Tyr Ser Val Ile Gly Pro Asn Thr Thr Pro Glu Ile Ala Asp Ala Ala
            100                 105                 110

Ala Ile Thr Asp Trp Leu Arg Asp Gly Leu Ser Asp Asn Leu Pro Gln
        115                 120                 125

Ala Leu Asn Asn His Val Arg Pro Asn Phe Glu Lys Phe Val Leu Ala
    130                 135                 140

Gly His Ser Arg Gly Gly Lys Val Ala Phe Ala Leu Ala Leu Gly Arg
145                 150                 155                 160

Val Ser Gln Pro Ser Leu Lys Tyr Ser Ala Leu Val Gly Leu Asp Pro
                165                 170                 175

Val Asp Gly Met Gly Lys Asp Gln Gln Thr Ser His Pro Ile Leu Ser
            180                 185                 190

Tyr Arg Glu His Ser Phe Asp Leu Gly Met Pro Thr Leu Val Val Gly
        195                 200                 205

Ser Gly Leu Gly Pro Cys Lys Arg Asn Pro Leu Phe Pro Pro Cys Ala
    210                 215                 220

Pro Gln Gly Val Asn His His Asp Phe Phe Tyr Glu Cys Val Ala Pro
225                 230                 235                 240

Ala Tyr His Phe Val Ala Ser Asp Tyr Gly His Leu Asp Phe Leu Asp
                245                 250                 255

Asp Asp Thr Lys Gly Ile Arg Gly Lys Ala Thr Tyr Cys Leu Cys Lys
            260                 265                 270

Asn Gly Glu Ala Arg Glu Pro Met Arg Lys Phe Ser Gly Gly Ile Val
        275                 280                 285

Val Ala Phe Leu Gln Ala Phe Leu Gly Asp Asn Arg Gly Ala Leu Asn
    290                 295                 300

Asp Ile Met Val Tyr Pro Ser His Ala Pro Val Lys Ile Glu Pro Pro
305                 310                 315                 320

Glu Ser Leu Val Thr Glu Asp Val Lys Ser Pro Glu Val Glu Leu Leu
                325                 330                 335

Arg Arg Ala Val Cys Arg
            340

<210> SEQ ID NO 25
<211> LENGTH: 884
<212> TYPE: DNA
<213> ORGANISM: Brassica oleracea
```

<400> SEQUENCE: 25

```
acacaaaaaa atatataaca caaagaaata gaagaaggaa aaaatgtccc cctcctttct     60
tttctttact ttgttttga taaaggaaat gtcctcttca tcatcagcaa actcctttga    120
ggacggcaaa tacaaaacag atcttttaac agtaggctta tcatcttgct gctggaaaaa   180
gccctcctct tctccgactc cgcagtctcc gccgaagagg cttttggtgg caacgccggt   240
ggaggaagga gaatatccgg tggtgatgct cctccatggt taccttctct acaactcatt   300
ttattcccag cttatgttgc atgtctcttc ccatggcttc attgtcatcg ctccgcagtt   360
atatagcatt gccggaccag acaccatgga tgagataaaa tcaacggcag agattattga   420
ttggttatcg gtcggactaa accactttct tccaccacaa gtaacaccaa acctatccaa   480
gttcgcactc tccggccata gccgtggtgg aagaccgca tttgccttgg ccttaaagaa    540
atttggatac tcgtccgacc taaagatctc ggcattgata ggtatagatg ttggaactgt   600
tttttggaca aatggctatg ccaatattc cggtgaattt ttcgagcaat ttgattgtcg    660
aaatgaccgg attgtggaat cgtaggattc attgttatga gcactatggt atagtgtaat   720
catatatcaa aaacgaagtt cgtttgaatg agaaatgaaa gtctaaaata gattatttgt   780
aaaatatcta tattagaatt atgaggtaag aaacctcttg tgtttaaaat ggagaagtta   840
taacaaagtt ataaaaaact ttgtaaacaa tttggtgtgt tagc                    884
```

<210> SEQ ID NO 26
<211> LENGTH: 213
<212> TYPE: PRT
<213> ORGANISM: Brassica oleracea

<400> SEQUENCE: 26

```
Met Ser Pro Ser Phe Leu Phe Phe Thr Leu Phe Leu Ile Lys Glu Met
1               5                   10                  15
Ser Ser Ser Ser Ser Ala Asn Ser Phe Glu Asp Gly Lys Tyr Lys Thr
                20                  25                  30
Asp Leu Leu Thr Val Gly Leu Ser Ser Cys Cys Trp Lys Lys Pro Ser
            35                  40                  45
Ser Ser Pro Thr Pro Gln Ser Pro Pro Lys Arg Leu Leu Val Ala Thr
        50                  55                  60
Pro Val Glu Glu Gly Glu Tyr Pro Val Met Leu Leu His Gly Tyr
65                  70                  75                  80
Leu Leu Tyr Asn Ser Phe Tyr Ser Gln Leu Met Leu His Val Ser Ser
                85                  90                  95
His Gly Phe Ile Val Ile Ala Pro Gln Leu Tyr Ser Ile Ala Gly Pro
                100                 105                 110
Asp Thr Met Asp Glu Ile Lys Ser Thr Ala Glu Ile Ile Asp Trp Leu
            115                 120                 125
Ser Val Gly Leu Asn His Phe Leu Pro Pro Gln Val Thr Pro Asn Leu
        130                 135                 140
Ser Lys Phe Ala Leu Ser Gly His Ser Arg Gly Gly Lys Thr Ala Phe
145                 150                 155                 160
Ala Leu Ala Leu Lys Lys Phe Gly Tyr Ser Ser Asp Leu Lys Ile Ser
                165                 170                 175
Ala Leu Ile Gly Ile Asp Val Gly Thr Val Phe Trp Thr Asn Gly Tyr
                180                 185                 190
```

```
Gly Gln Tyr Ser Gly Glu Phe Phe Glu Gln Phe Asp Cys Arg Asn Asp
            195                 200                 205

Arg Ile Val Glu Ser
    210

<210> SEQ ID NO 27
<211> LENGTH: 329
<212> TYPE: PRT
<213> ORGANISM: Citrus sinensis

<400> SEQUENCE: 27

Met Ala Ala Met Val Asp Ala Lys Pro Ala Ser Val Gln Gly Thr
1               5                   10                  15

Pro Leu Leu Ala Thr Ala Thr Leu Pro Val Phe Thr Arg Gly Ile Tyr
                20                  25                  30

Ser Thr Lys Arg Ile Thr Leu Glu Thr Ser Ser Pro Ser Pro Pro
            35                  40                  45

Pro Pro Lys Pro Leu Ile Ile Val Thr Pro Ala Gly Lys Gly Thr Phe
    50                  55                  60

Asn Val Ile Leu Phe Leu His Gly Thr Ser Leu Ser Asn Lys Ser Tyr
65                  70                  75                  80

Ser Lys Ile Phe Asp His Ile Ala Ser His Gly Phe Ile Val Val Ala
                85                  90                  95

Pro Gln Leu Tyr Thr Ser Ile Pro Pro Ser Ala Thr Asn Glu Leu
                100                 105                 110

Asn Ser Ala Ala Glu Val Ala Glu Trp Leu Pro Gln Gly Leu Gln Gln
            115                 120                 125

Asn Leu Pro Glu Asn Thr Glu Ala Asn Val Ser Leu Val Ala Val Met
130                 135                 140

Gly His Ser Arg Gly Gly Gln Thr Ala Phe Ala Leu Ser Leu Arg Tyr
145                 150                 155                 160

Gly Phe Gly Ala Val Ile Gly Leu Asp Pro Val Ala Gly Thr Ser Lys
                165                 170                 175

Thr Thr Gly Leu Asp Pro Ser Ile Leu Ser Phe Asp Ser Phe Asp Phe
                180                 185                 190

Ser Ile Pro Val Thr Val Ile Gly Thr Gly Leu Gly Gly Val Ala Arg
            195                 200                 205

Cys Ile Thr Ala Cys Ala Pro Glu Gly Ala Asn His Glu Glu Phe Phe
210                 215                 220

Asn Arg Cys Lys Asn Ser Ser Arg Ala His Phe Val Ala Thr Asp Tyr
225                 230                 235                 240

Gly His Met Asp Ile Leu Asp Asp Asn Pro Ser Asp Val Lys Ser Trp
                245                 250                 255

Ala Leu Ser Lys Tyr Phe Cys Lys Asn Gly Asn Glu Ser Arg Asp Pro
                260                 265                 270

Met Arg Arg Cys Val Ser Gly Ile Val Val Ala Phe Leu Lys Asp Phe
            275                 280                 285

Phe Tyr Gly Asp Ala Glu Asp Phe Arg Gln Ile Leu Lys Asp Pro Ser
    290                 295                 300

Phe Ala Pro Ile Lys Leu Asp Ser Val Glu Tyr Ile Asp Ala Ser Ser
305                 310                 315                 320

Met Leu Thr Thr Thr His Val Lys Val
                325
```